US011478218B2

(12) United States Patent
Rothberg

(10) Patent No.: US 11,478,218 B2
(45) Date of Patent: Oct. 25, 2022

(54) METHODS AND APPARATUS FOR COLLECTION OF ULTRASOUND DATA

(71) Applicant: BFLY Operations, Inc., Guilford, CT (US)

(72) Inventor: Alex Rothberg, New York, NY (US)

(73) Assignee: BFLY Operations, Inc., Guilford, CT (US)

( * ) Notice: Subject to any disclaimer, the term of this patent is extended or adjusted under 35 U.S.C. 154(b) by 122 days.

(21) Appl. No.: 16/118,256

(22) Filed: Aug. 30, 2018

(65) Prior Publication Data

US 2019/0059851 A1    Feb. 28, 2019

Related U.S. Application Data

(60) Provisional application No. 62/553,047, filed on Aug. 31, 2017.

(51) Int. Cl.
*A61B 8/00* (2006.01)
*A61B 8/08* (2006.01)

(52) U.S. Cl.
CPC .............. *A61B 8/42* (2013.01); *A61B 8/08* (2013.01); *A61B 8/0883* (2013.01); *A61B 8/4245* (2013.01); *A61B 8/5215* (2013.01); *A61B 8/5253* (2013.01); *A61B 8/4472* (2013.01); *A61B 8/461* (2013.01); *A61B 8/565* (2013.01)

(58) Field of Classification Search
None
See application file for complete search history.

(56) References Cited

U.S. PATENT DOCUMENTS

| 5,353,796 | A | 10/1994 | Schroeder et al. |
| 6,440,073 | B1 | 8/2002 | Robinson et al. |
| 9,161,742 | B2 | 10/2015 | Neasham et al. |
| 2004/0019270 | A1 | 1/2004 | Takeuchi |
| 2007/0021738 | A1 | 1/2007 | Hasser et al. |
| 2007/0238999 | A1 | 10/2007 | Specht |
| 2011/0055447 | A1 | 3/2011 | Costa |
| 2011/0196235 | A1* | 8/2011 | Dunbar ................. G16H 40/63 600/437 |
| 2013/0225986 | A1* | 8/2013 | Eggers ................ A61B 8/4405 600/425 |

(Continued)

FOREIGN PATENT DOCUMENTS

| WO | WO 2015/087218 A1 | 6/2015 |
| WO | WO 2017/222970 A1 | 12/2017 |

OTHER PUBLICATIONS

International Search Report and Written Opinion dated Nov. 14, 2018 in connection with International Application No. PCT/US2018/048731.

(Continued)

*Primary Examiner* — Katherine L Fernandez
(74) *Attorney, Agent, or Firm* — Osha Bergman Watanabe & Burton LLP

(57) ABSTRACT

Aspects of the technology described herein relate to instructing an operator to move an ultrasound device along a predetermined path relative to an anatomical area in order to collect first ultrasound data and second ultrasound data, the first ultrasound data capable of being transformed into an ultrasound image of a target anatomical view, and the second ultrasound data not capable of being transformed into the ultrasound image of the target anatomical view.

25 Claims, 22 Drawing Sheets

(56) References Cited

U.S. PATENT DOCUMENTS

| | | | |
|---|---|---|---|
| 2015/0223772 A1* | 8/2015 | Shi ..................... | A61B 8/0825 600/459 |
| 2016/0143627 A1 | 5/2016 | Vignon et al. | |
| 2017/0120080 A1* | 5/2017 | Phillips ................. | A61N 7/022 |
| 2017/0215842 A1* | 8/2017 | Ryu ...................... | A61B 8/465 |
| 2017/0360397 A1 | 12/2017 | Rothberg et al. | |
| 2017/0360401 A1* | 12/2017 | Rothberg ............. | G06K 9/6271 |
| 2018/0153505 A1* | 6/2018 | Cadieu .................. | A61B 34/20 |

OTHER PUBLICATIONS

PCT/US2018/048731, Mar. 12, 2020, International Preliminary Report on Patentability.
International Preliminary Report on Patentability dated Mar. 12, 2020 in connection with International Application No. PCT/US2018/048731.
PCT/US2018/048731, Nov. 14, 2018, International Search Report and Written Opinion.
Extended European Search Report dated Apr. 19, 2021 in connection with European Application No. 18850133.2.

\* cited by examiner

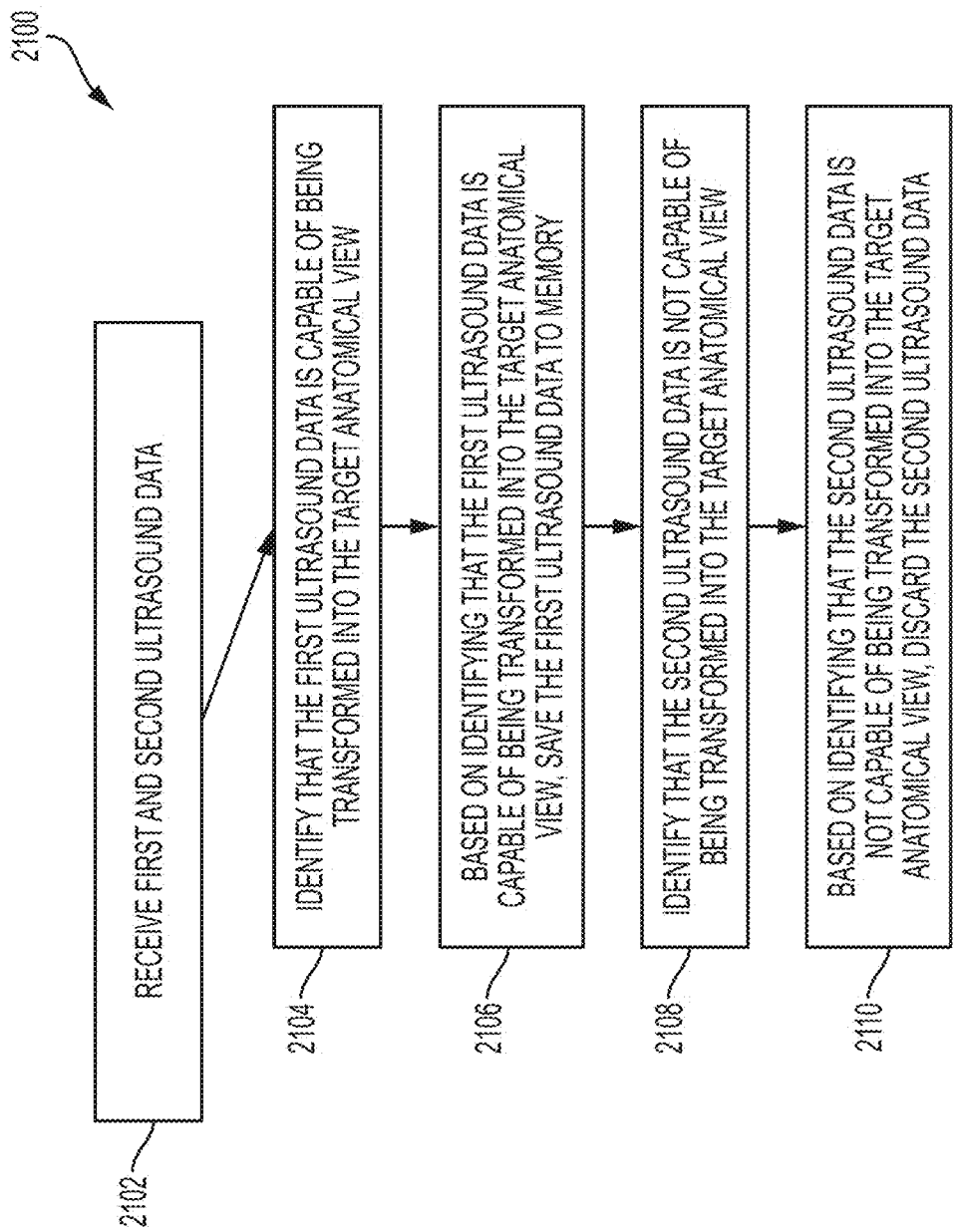

METHODS AND APPARATUS FOR COLLECTION OF ULTRASOUND DATA

CROSS-REFERENCE TO RELATED APPLICATIONS

This Application claims the benefit under 35 USC § 119(e) of U.S. Application Ser. No. 62/553,047, filed Aug. 31, 2017, and entitled "METHODS AND APPARATUS FOR COLLECTION OF ULTRASOUND DATA," which is hereby incorporated herein by reference in its entirety.

FIELD

Generally, the aspects of the technology described herein relate to ultrasound systems. Some aspects relate to techniques for instructing an operator to use an ultrasound device to collect ultrasound data.

BACKGROUND

Conventional ultrasound systems are large, complex, and expensive systems that are typically used in large medical facilities (such as a hospital) and are operated by medical professionals that are experienced with these systems, such as ultrasound technicians. Ultrasound technicians typically undergo years of hands-on training to learn how to properly use the ultrasound imaging system. For example, an ultrasound technician may learn how to appropriately position an ultrasound device on a subject to capture an ultrasound image in various anatomical views.

SUMMARY

According to one aspect, a method includes instructing, by a host device, an operator to move an ultrasound device along a predetermined path relative to an anatomical area in order to collect first ultrasound data and second ultrasound data, the first ultrasound data capable of being transformed into an ultrasound image of a target anatomical view, and the second ultrasound data not capable of being transformed into the ultrasound image of the target anatomical view.

In some embodiments, the method further includes receiving, at the host device, the first and second ultrasound data collected by the ultrasound device, and transmitting, by the host device, the first and second ultrasound data to a server without distinguishing between the first and second ultrasound data. In some embodiments, the server is configured to identify that the first ultrasound data is capable of being transformed into the ultrasound image of the target anatomical view and, based on identifying that the first ultrasound data is capable of being transformed into the ultrasound image of the target anatomical view, save the first ultrasound data to memory. In some embodiments, the server is further configured to identify that the second ultrasound data is not capable of being transformed into the ultrasound image of the target anatomical view and, based on identifying that the second ultrasound data is not capable of being transformed into the ultrasound image of the target anatomical view, discard the second ultrasound data. In some embodiments, the server is configured to use a machine learning technique to identify that the first ultrasound data is capable of being transformed into the ultrasound image of the target anatomical view.

In some embodiments, instructing the operator includes providing at least one of a predetermined video and a predetermined image displaying the predetermined path relative to the anatomical area. In some embodiments, instructing the operator includes providing instructions expressed in words for moving the ultrasound device along the predetermined path relative to the anatomical area.

In some embodiments, moving the ultrasound device along the predetermined path relative to the anatomical area causes the ultrasound device to move across substantially all of a surface of at least one of the abdomen, arm, breast, chest, foot, genitalia, hand, head, leg, neck, pelvis, thorax, and torso. In some embodiments, the predetermined path includes a serpentine path across substantially all of the anatomical area. In some embodiments, the predetermined path includes a path across substantially all of the anatomical area, and the anatomical area is greater than 25 cm$^2$ in area.

In some embodiments, the predetermined path includes a pivot of the ultrasound device. In some embodiments, the predetermined path includes a rotation of the ultrasound device about its longitudinal axis.

In some embodiments, the method further includes determining the predetermined path based on determining that a measure of ease of describing the predetermined path exceeds a threshold. In some embodiments, the measure of ease of describing the predetermined path includes a measure of ease of describing the predetermined path visually. In some embodiments, the measure of ease of describing the predetermined path includes a measure of ease of describing the predetermined path with words.

According to another aspect, at least one non-transitory computer-readable storage medium stores processor-executable instructions that, when executed by at least one processor, cause the at least one processor to instruct an operator to move an ultrasound device along a predetermined path relative to an anatomical area in order to collect first ultrasound data and second ultrasound data, the first ultrasound data capable of being transformed into an ultrasound image of a target anatomical view, and the second ultrasound data not capable of being transformed into the ultrasound image of the target anatomical view.

In some embodiments, the at least one non-transitory computer-readable storage medium further stores processor-executable instructions that, when executed by the at least one processor, cause the at least one processor to receive, at the host device, the first and second ultrasound data collected by the ultrasound device; and transmit the first and second ultrasound data to a server without distinguishing between the first and second ultrasound data. In some embodiments, the server is configured to identify that the first ultrasound data is capable of being transformed into the ultrasound image of the target anatomical view and, based on identifying that the first ultrasound data is capable of being transformed into the ultrasound image of the target anatomical view, save the first ultrasound data to memory. In some embodiments, the server is further configured to identify that the second ultrasound data is not capable of being transformed into the ultrasound image of the target anatomical view and, based on identifying that the second ultrasound data is not capable of being transformed into the ultrasound image of the target anatomical view, discard the second ultrasound data. In some embodiments, the server is configured to use a machine learning technique to identify that the first ultrasound data is capable of being transformed into the ultrasound image of the target anatomical view.

In some embodiments, the at least one non-transitory computer-readable storage medium further stores processor-executable instructions that, when executed by the at least one processor, cause the at least one processor to provide at least one of a predetermined video and a predetermined image displaying the predetermined path relative to the anatomical area. In some embodiments, the at least one non-transitory computer-readable storage medium further stores processor-executable instructions that, when executed by the at least one processor, cause the at least one processor to provide instructions expressed in words for moving the ultrasound device along the predetermined path relative to the anatomical area.

In some embodiments, moving the ultrasound device along the predetermined path relative to the anatomical area causes the ultrasound device to move across substantially all of a surface of at least one of an abdomen, arm, breast, chest, foot, genitalia, hand, head, leg, neck, pelvis, thorax, and torso. In some embodiments, the predetermined path includes a serpentine path across substantially all of the anatomical area. In some embodiments, the predetermined path includes a path across substantially all of the anatomical area, and the anatomical area is greater than 25 cm$^2$ in area.

In some embodiments, the predetermined path includes a pivot of the ultrasound device. In some embodiments, the predetermined path includes a rotation of the ultrasound device about its longitudinal axis.

In some embodiments, the at least one non-transitory computer-readable storage medium further stores processor-executable instructions that, when executed by the at least one processor, cause the at least one processor to determine the predetermined path based on determining that a measure of ease of describing the predetermined path exceeds a threshold. In some embodiments, the measure of ease of describing the predetermined path includes a measure of ease of describing the predetermined path visually. In some embodiments, the measure of ease of describing the predetermined path includes a measure of ease of describing the predetermined path with words.

According to another aspect, a system includes an ultrasound device and a host device configured to instruct an operator to move the ultrasound device along a predetermined path relative to an anatomical area in order to collect first ultrasound data and second ultrasound data, the first ultrasound data capable of being transformed into an ultrasound image of a target anatomical view, and the second ultrasound data not capable of being transformed into the ultrasound image of the target anatomical view.

In some embodiments, the host device is further configured to receive the first and second ultrasound data collected by the ultrasound device and transmit the first and second ultrasound data to a server without distinguishing between the first and second ultrasound data. In some embodiments, the server is configured to identify that the first ultrasound data is capable of being transformed into the ultrasound image of the target anatomical view and, based on identifying that the first ultrasound data is capable of being transformed into the ultrasound image of the target anatomical view, save the first ultrasound data to memory. In some embodiments, the server is further configured to identify that the second ultrasound data is not capable of being transformed into the ultrasound image of the target anatomical view and, based on identifying that the second ultrasound data is not capable of being transformed into the ultrasound image of the target anatomical view, discard the second ultrasound data. In some embodiments, the server is configured to use a machine learning technique to identify that the first ultrasound data is capable of being transformed into the ultrasound image of the target anatomical view.

In some embodiments, the host device is further configured to provide at least one of a predetermined video and a predetermined image displaying the predetermined path relative to the anatomical area. In some embodiments, the host device is further configured to provide instructions expressed in words for moving the ultrasound device along the predetermined path relative to the anatomical area.

In some embodiments, moving the ultrasound device along the predetermined path relative to the anatomical area causes the ultrasound device to move across substantially all of a surface of at least one of an abdomen, arm, breast, chest, foot, genitalia, hand, head, leg, neck, pelvis, thorax, and torso. In some embodiments, the predetermined path includes a serpentine path across substantially all of the anatomical area. In some embodiments, the predetermined path includes a path across substantially all of the anatomical area, and the anatomical area is greater than 25 cm$^2$ in area.

In some embodiments, the predetermined path includes a pivot of the ultrasound device. In some embodiments, the predetermined path includes a rotation of the ultrasound device about its longitudinal axis.

According to another aspect, a method includes instructing, by a host device, an operator to move an ultrasound device along a path relative to an anatomical area in order to collect first ultrasound data and second ultrasound data, the first ultrasound data capable of being transformed into an ultrasound image of a target anatomical view, and the second ultrasound data not capable of being transformed into the ultrasound image of the target anatomical view, where the host device does not provide feedback to the operator regarding collection of the first ultrasound data while the operator moves the ultrasound device along the path.

In some embodiments, the method further includes receiving, at the host device, the first and second ultrasound data collected by the ultrasound device, and transmitting, by the host device, the first and second ultrasound data to a server without distinguishing between the first and second ultrasound data. In some embodiments, the server is configured to identify that the first ultrasound data is capable of being transformed into the ultrasound image of the target anatomical view and, based on identifying that the first ultrasound data is capable of being transformed into the ultrasound image of the target anatomical view, save the first ultrasound data to memory. In some embodiments, the server is further configured to identify that the second ultrasound data is not capable of being transformed into the ultrasound image of the target anatomical view and, based on identifying that the second ultrasound data is not capable of being transformed into the ultrasound image of the target anatomical view, discard the second ultrasound data. In some embodiments, the server is configured to use a machine learning technique to identify that the first ultrasound data is capable of being transformed into the ultrasound image of the target anatomical view.

In some embodiments, moving the ultrasound device along the path relative to the anatomical area causes the ultrasound device to move across substantially all of a surface of at least one of an abdomen, arm, breast, chest, foot, genitalia, hand, head, leg, neck, pelvis, thorax, and torso. In some embodiments, the predetermined path includes a path across substantially all of the anatomical area, and the anatomical area is greater than 25 cm$^2$ in area.

In some embodiments, the path includes a pivot of the ultrasound device. In some embodiments, the path includes a rotation of the ultrasound device about its longitudinal axis.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

FIG. 21 shows an example process for processing ultrasound data in accordance with certain embodiments disclosed herein.

DETAILED DESCRIPTION

Figure 1:
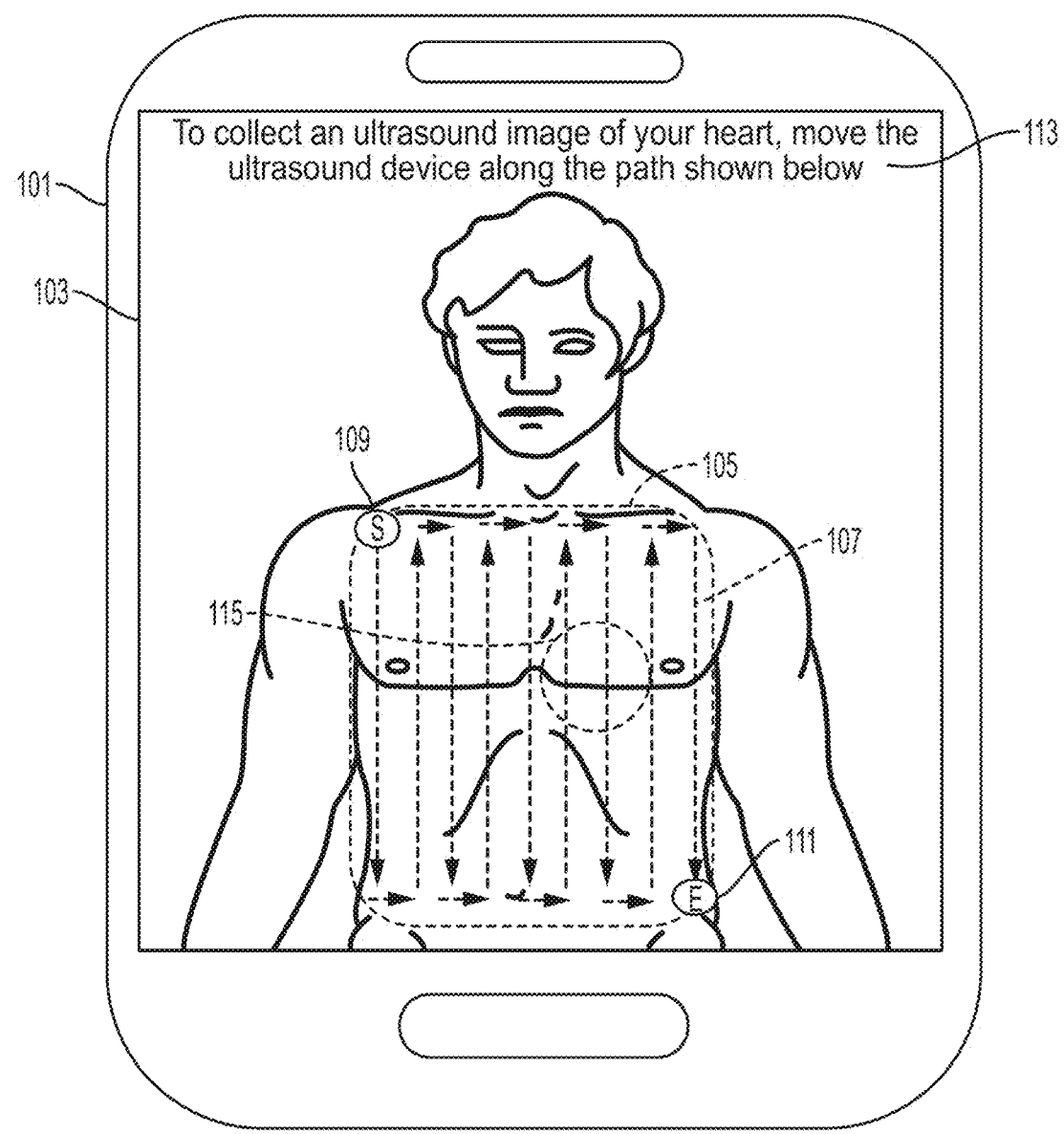
FIG. 1 shows an example of instructions for moving an ultrasound device along a predetermined path to collect ultrasound data capable of being transformed into an ultrasound image of a target anatomical view in accordance with certain embodiments disclosed herein.

Ultrasound examinations often include the acquisition of ultrasound images that contain a view of a particular anatomical structure (e.g., an organ) of a subject. Acquisition of these ultrasound images typically requires considerable skill. For example, an ultrasound technician operating an ultrasound device may need to know where the anatomical structure to be imaged is located on the subject and further how to properly position the ultrasound device on the subject to capture a medically relevant ultrasound image of the anatomical structure. Holding the ultrasound device a few inches too high or too low on the subject may make the difference between capturing a medically relevant ultrasound image and capturing a medically irrelevant ultrasound image. As a result, non-expert operators of an ultrasound device may have considerable trouble capturing medically relevant ultrasound images of a subject. Common mistakes by these non-expert operators include: capturing ultrasound images of the incorrect anatomical structure and capturing foreshortened (or truncated) ultrasound images of the correct anatomical structure.

Conventional ultrasound systems are large, complex, and expensive systems that are typically only purchased by large medical facilities with significant financial resources. Recently, cheaper and less complex ultrasound imaging devices have been introduced. Such imaging devices may include ultrasonic transducers monolithically integrated onto a single semiconductor die to form a monolithic ultrasound device. Aspects of such ultrasound-on-a chip devices are described in U.S. patent application Ser. No. 15/415,434 titled "UNIVERSAL ULTRASOUND DEVICE AND RELATED APPARATUS AND METHODS," filed on Jan. 25, 2017 (and assigned to the assignee of the instant application) and published as U.S. Pat. Pub. No. 2017-0360397 A1, which is incorporated by reference herein in its entirety. The reduced cost and increased portability of these new ultrasound devices may make them significantly more accessible to the general public than conventional ultrasound devices.

The inventors have recognized and appreciated that although the reduced cost and increased portability of ultrasound imaging devices makes them more accessible to the general populace, people who could make use of such devices have little to no training for how to use them. For example, a small clinic without a trained ultrasound technician on staff may purchase an ultrasound device to help diagnose patients. In this example, a nurse at the small clinic may be familiar with ultrasound technology and human physiology, but may know neither which anatomical views of a patient need to be imaged in order to identify medically-relevant information about the patient nor how to obtain such anatomical views using the ultrasound device. In another example, an ultrasound device may be issued to a patient by a physician for at-home use to monitor the patient's heart. In all likelihood, the patient understands neither human physiology nor how to image his or her own heart with the ultrasound device.

Accordingly, the inventors have developed assistive ultrasound imaging technology for instructing an operator of an ultrasound device how to move the ultrasound device relative to an anatomical area of a subject in order to capture a medically relevant ultrasound image. Providing instructions to the operator for positioning the ultrasound device in order to collect ultrasound data capable of being transformed into an ultrasound image containing a target anatomical view (for simplicity, referred to herein as "target ultrasound data") may be difficult. For example, if the target ultrasound data can be collected by placing the ultrasound device at a specific location within the anatomical area (for simplicity, referred to herein as the "target location," and assuming other requirements such as the tilt and the rotational orientation of the ultrasound device are fulfilled), one option for instructing the operator to collect the target ultrasound data may be to provide an explicit description of the target location and instructing the operator to place the ultrasound device at the target location. However, this may be difficult if there is not an easy way to describe the target location, either with visually or with words, which may be the case for multiple reasons: (1) the target location may not have a specific name or verbal description; (2) the target location may not be oriented, in an orientation that can be described easily, relative to another location that does have a specific name/verbal description; (3) the target location may not have visual distinguishing features; and/or (4) the target location may not be oriented, in an orientation that can be easily shown visually, relative to another location that does have visual distinguishing features. Additionally, if the target location is difficult to describe, following instructions to place the ultrasound device at the target location may be difficult for the operator.

The inventors have recognized that it may be possible to enable the operator to collect, with the ultrasound device, the target ultrasound data without providing an explicit description of the target location. (For simplicity, as used herein, references to an operator collecting ultrasound data mean that the operator uses an ultrasound device to collect the ultrasound data). The inventors have recognized that it is possible to provide a description of a path that does not explicitly mention the target location, but which includes the target location, as well as other locations (for simplicity, referred to herein as "non-target locations") where ultrasound data not capable of being transformed into an ultrasound image of the target anatomical view (for simplicity, referred to herein as "non-target ultrasound data") is collected. Such a path may be predetermined in that the path may be generated based on the target ultrasound data to be collected prior to the operator beginning to collect ultrasound data. Moving the ultrasound device along the predetermined path should, if done correctly, result in collection of the target ultrasound data. While moving the ultrasound device along such a path causes the ultrasound device to collect non-target ultrasound data in addition to the target ultrasound data, the inventors have recognized that describing such a path may be easier than describing the target location. Furthermore, because the description of such a path may be less complex than the description of the target location, following instructions to move the ultrasound device along such a path may be easier for an operator than following instructions to place the ultrasound device at the target location. For example, instructing the operator to move the ultrasound device along a path that covers substantially all of an anatomical area may be easier than instructing the operator to place the ultrasound device at a specific target location within the anatomical area. Furthermore, it may be easier for the operator to follow instructions to move the ultrasound device in a path across substantially all of the anatomical area than to follow instructions to specifically place the ultrasound device at the target location. As a particular example, consider a target location that can most easily be described as "two and a quarter inches above and one and three-quarters inches to the right of the navel." An easier way to instruct the operator to collect the target ultrasound data from this target location may be to instruct the operator to move the ultrasound device in a path across substantially all of the abdomen, a path which would include the target location as well as non-target locations. The inventors have therefore recognized that it can be beneficial to instruct the operator to move the ultrasound device along a path whereby the ultrasound device collects target and non-target ultrasound data, as such an instruction may be easier to describe and follow than a specific description of the target location. In other words, purposefully instructing the operator to collect non-target ultrasound data may, unexpectedly and non-intuitively, help the operator to collect the target ultrasound data.

Another option for instructing the operator to collect target ultrasound data may be to provide real-time instructions to the operator for placing the ultrasound device. A host device may receive ultrasound data from the ultrasound device, analyze the ultrasound data in real time to determine whether the data represents the target ultrasound data, and if the data does not represent the target ultrasound data, provide real-time instructions to the operator to move the ultrasound device until the operator has placed the ultrasound device at the target location. However, for a host device to provide real-time instructions, the host device may need to have sufficient memory to store specific algorithms for analyzing the collected ultrasound data, determining whether it represents the target ultrasound data, and providing instructions based on the collected ultrasound data for moving the ultrasound device from its present location to the target location. Additionally, the host device may need to execute computations using these algorithms in real time, which can consume power and require a certain level of processing speed. In contrast, it may be possible to describe a predetermined path that includes the target location, as described above, rather than guiding the operator to move the ultrasound device to the target location in real time. A host device may have lower requirements in terms of memory, processing speed, and power consumption, in order to provide predetermined instructions. For example, the host device may only need to have the capability to display an image of the predetermined path, or play a video of the predetermined path, or play spoken instructions for moving the ultrasound device along the predetermined path.

Accordingly, certain disclosed embodiments relate to new techniques for instructing the operator to capture ultrasound data capable of being transformed into an ultrasound image that contains the target anatomical view. The instructions may be provided via a software application (hereinafter "App") installed on a host device of the operator (such as: a mobile device, a smartphone or smart-device, tablet, etc.). For example, the operator may install the App on a host device and connect the host device to an ultrasound device (e.g., using a wireless connection such as BLUETOOTH or a wired connection such as a Lightning cable). The software application may then instruct the operator to move the ultrasound device along a predetermined path relative an anatomical area of the subject. The instructions may instruct the operator to move the ultrasound device along a predetermined path relative to the anatomical area such that moving the ultrasound device along the predetermined path relative to the anatomical area causes the ultrasound device to collect both ultrasound data that can be transformed into an ultrasound image of the target anatomical view ("target ultrasound data") as well as ultrasound data that cannot be transformed into an ultrasound image of the target anatomical view ("non-target ultrasound data"). As discussed above, it can be beneficial to instruct the operator to move the ultrasound device along a path whereby the ultrasound device collects target and non-target ultrasound data, as such an instruction may be easier to describe and follow than instructions containing a specific description of the location where the target ultrasound data can be collected.

The above discussion applies equally to instructing an operator to tilt the ultrasound device and/or rotate the ultrasound device along a predetermined path, such that target ultrasound data can be collected while the ultrasound device moves along the predetermined path.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

As referred to herein, moving an ultrasound device along a "path" should be understood to mean moving any portion of the ultrasound device through space. Examples of paths may include translational movement of the entire ultrasound device, rotation of the ultrasound device around a longitudinal axis of the ultrasound device, and pivoting of the ultrasound device around a location to which a portion of the ultrasound device remains substantially fixed.

As referred to herein, collecting an ultrasound image should be understood to mean collecting ultrasound data capable of being transformed into the ultrasound image.

As referred to herein, "transforming" ultrasound data into an ultrasound image should be understood to mean any process or group of processes that uses ultrasound acoustical signals to determine values (e.g., grayscale intensity values, red-green-blue values, etc.) of pixels in an image.

FIG. 1 shows an example of instructions for moving an ultrasound device along a predetermined path to collect ultrasound data capable of being transformed into an ultrasound image of a target anatomical view ("target ultrasound data") in accordance with certain embodiments disclosed herein. FIG. 1 shows a host device 101 that includes a display 103. The display 103 displays an image of an anatomical area 105 (in the example of FIG. 1, the front surface of the torso). The display 103 also displays an image of a predetermined path 107 superimposed on the image of the anatomical area 105. The predetermined path 107 includes translational movement of the ultrasound device. The image of the predetermined path 107 includes an indication of a starting point 109 and an indication of an ending point 111 on the predetermined path 107. The display 103 also displays text 113 instructing the operator to collect an ultrasound image of the target anatomical view (in the example of FIG. 1, the heart) by moving an ultrasound device along the predetermined path 107. The instructions illustrated by FIG. 1 include the image of the anatomical area 105, the image of the predetermined path 107 (including the starting point 109 and the ending point 111), and the text 113.

In the example of FIG. 1, the predetermined path 107 is a path, and in particular a serpentine path, that covers substantially all of the anatomical area 105. The shape of the predetermined path 107 may be helpful in that the operator need not necessarily lift the ultrasound device while moving the ultrasound device along the predetermined path 107. Additionally, the shape of the predetermined path 107 may be helpful in that the major legs of the predetermined path 107 (in the example of FIG. 1, the upwards and downwards legs of the predetermined path 107) may be substantially of the same length, which may help the operator move the ultrasound device in a consistent manner. It can be appreciated that in order to collect data capable of being transformed into an ultrasound image of the target anatomical view, which in the example of FIG. 1 is the heart, it may only be necessary to place the ultrasound device near a region 115 where the heart is located (assuming other requirements such as the tilt and the rotational orientation of the ultrasound device are fulfilled). However, providing instructions to place the ultrasound device near the region 115 may be difficult, as precisely and efficiently describing the region 115 visually or with words may be difficult. On the other hand, the instructions of FIG. 1 to move the ultrasound device along the predetermined path 107, which instruct the operator to move the ultrasound device across substantially all of the anatomical area 105, may be easier to describe and follow than specific instructions to place the ultrasound device at the region 115. Furthermore, moving the ultrasound device along the predetermined path 107 should result in the ultrasound device collecting the target ultrasound data when the ultrasound device moves over the region 115 along the predetermined path 107 (assuming other requirements such as the ultrasound device's tilt and rotational orientation are fulfilled). As a side effect of moving the ultrasound device along the predetermined path 107, non-target ultrasound data may be collected when the ultrasound device moves over other regions along the predetermined path 107. In some embodiments, the host device 101 may be a mobile smartphone, a tablet, a laptop, a smart watch, a virtual reality (VR) headset, an augmented reality (AR) headset, or a smart wearable device. In some embodiments, the indication of the starting point 109 and the indication of the ending point 111 may not be displayed on the display 103. In some embodiments, the text 113 may display different text with the same general meaning as the text 113 shown in FIG. 1. In some embodiments, the text 113 may not be displayed, but instead may be played by the host device 101 as audio. In some embodiments, the text 113 may be absent.

It should be appreciated that the image of the predetermined path 107 may not be intended to be followed exactly. Rather, the image of the predetermined path 107 may be intended to simply illustrate a serpentine path that covers substantially all of the anatomical area 105. For example, gaps between various legs of the image of the predetermined path 107 may be displayed due to resolution constraints of the display 103, and the instructions may not intend for the operator to skip these gaps when moving the ultrasound device across substantially all of the anatomical area 105.

It should be appreciated that the example in FIG. 1 is non-limiting, and the predetermined path 107 can take other forms. For example, the starting point 109 and the ending point 111 may be at other locations than those shown in FIG. 1. Additionally, for example, while the predetermined path 107 is shown in FIG. 1 as proceeding initially downwards and rightwards, the predetermined path 107 may proceed initially upwards and/or leftwards. Additionally, for example, while the predetermined path 107 is shown in FIG. 1 as proceeding substantially upwards and downwards across the anatomical area 105, the predetermined path 107 may proceed substantially rightwards and leftwards across the anatomical area 105. It should also be appreciated that the anatomical area 105 need not be the torso, but can be any anatomical area of the body, such as the abdomen, arm, breast, chest, foot, genitalia, hand, head, leg, neck, pelvis, and thorax. It should also be appreciated that the target anatomical view need not be a view of the heart, but may be a view of other structures and organs in the body.

Figure 2:
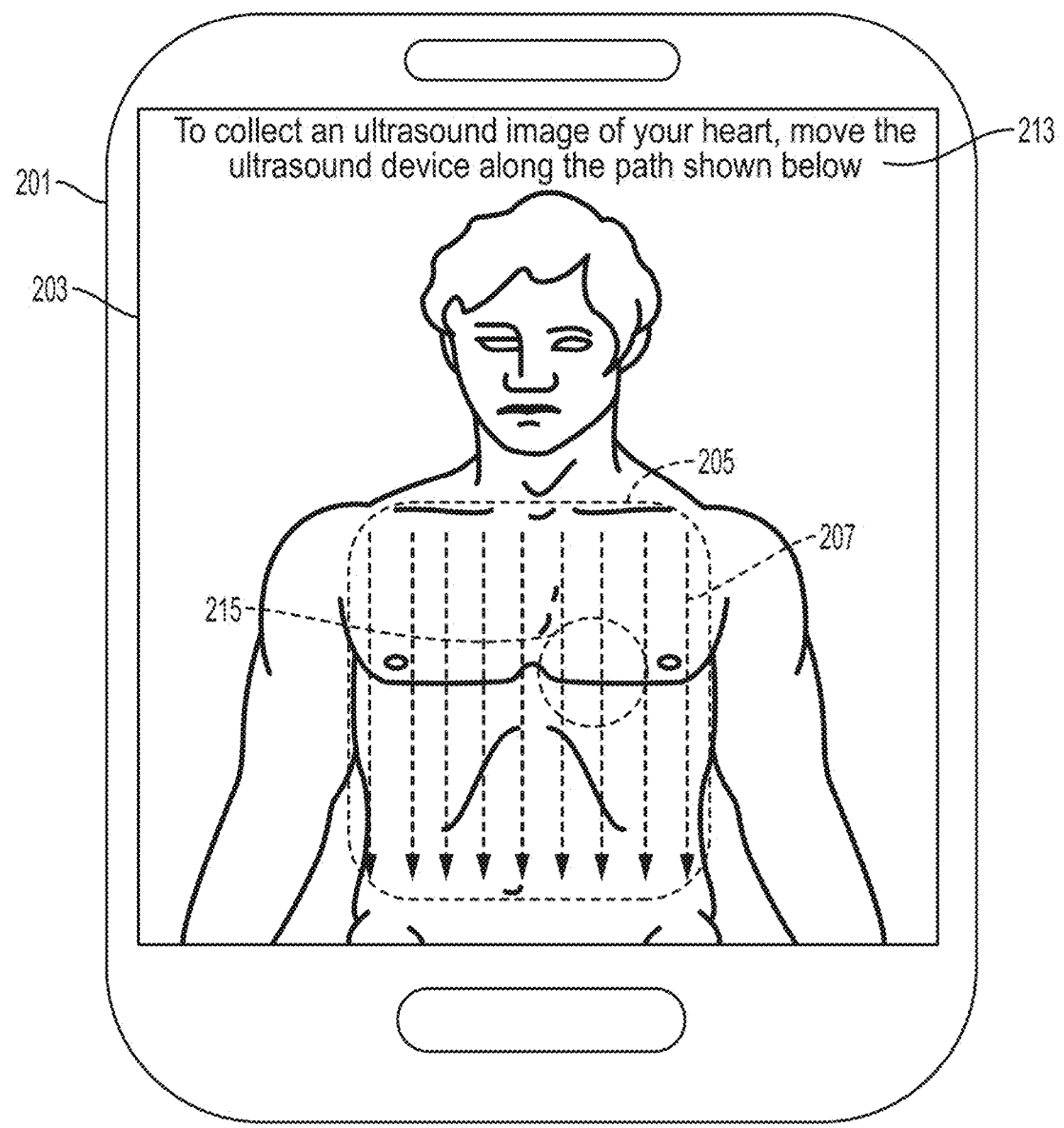
FIG. 2 shows another example of instructions for moving an ultrasound device along a predetermined path to collect ultrasound data capable of being transformed into an ultrasound image of a target anatomical view in accordance with certain embodiments disclosed herein.

FIG. 2 shows another example of instructions for moving an ultrasound device along a predetermined path to collect ultrasound data capable of being transformed into an ultrasound image of a target anatomical view ("target ultrasound data") in accordance with certain embodiments disclosed herein. FIG. 2 shows a host device 201 that includes a display 203. The display 203 displays an image of an anatomical area 205 (in the example of FIG. 2, the front surface of the torso). The display 203 also displays an image of a predetermined path 207 superimposed on the image of the anatomical area 205. The predetermined path 207 includes translational movement of the ultrasound device. The display 203 also displays text 213 instructing the user to collect an ultrasound image of the target anatomical view (in the example of FIG. 2, the heart) by moving an ultrasound device along the predetermined path 207. The instructions illustrated by FIG. 2 include the image of the anatomical area 205, the image of the predetermined path 207, and the text 213.

In the example of FIG. 2, the predetermined path 207 is a path that covers substantially all of the anatomical area 205. The predetermined path 207 includes parallel legs all proceeding in the same direction along the anatomical area 205. The shape of the predetermined path 207 may be helpful in that the operator may be able to move the ultrasound device along the anatomical area 205 in a single direction (in the example of FIG. 2, downwards). Additionally, the shape of the predetermined path 207 may be helpful in that the legs of the predetermined path 207 may be substantially of the same length, which may help the operator move the ultrasound device in a consistent manner. It can be appreciated that in order to collect data capable of being transformed into an ultrasound image of the target anatomical view, which in the example of FIG. 2 is the heart, it may only be necessary to place the ultrasound device near a region 215 where the heart is located (assuming other requirements such as the tilt and the rotational orientation of the ultrasound device are fulfilled). However, providing instructions to place the ultrasound device near the region 215 may be difficult, as precisely and efficiently describing the region 215 visually or with words may be difficult. On the other hand, the instructions of FIG. 2 to move the ultrasound device along the predetermined path 207, which instruct the operator to move the ultrasound device across substantially all of the anatomical area 205, may be easier to describe and follow than specific instructions to place the ultrasound device at the region 215. Furthermore, moving the ultrasound device along the predetermined path 207 should result in the ultrasound device collecting the target ultrasound data when the ultrasound device moves over the region 215 along the predetermined path 207 (assuming other requirements such as the ultrasound device's tilt and rotational orientation are fulfilled). As a side effect of moving the ultrasound device along the predetermined path 207, non-target ultrasound data may be collected when the ultrasound device moves over other regions along the predetermined path 207.

In some embodiments, the host device 201 may be a mobile smartphone, a tablet, a laptop, a smart watch, a virtual reality (VR) headset, an augmented reality (AR) headset, or a smart wearable device. In some embodiments, the text 213 may display different text with the same general meaning as the text 213 shown in FIG. 2. In some embodiments, the text 213 may not be displayed, but instead may be played by the host device 201 as audio. In some embodiments, the text 213 may be absent.

It should be appreciated that the image of the predetermined path 207 may not be intended to be followed exactly. Rather, the image of the predetermined path 207 may be intended to simply illustrate a path including parallel legs all proceeding in the same direction that cover substantially all of the anatomical area 205. For example, gaps between various legs of the image of the predetermined path 207 may be displayed due to resolution constraints of the display 203, and the instructions may not intend for the operator to skip these gaps when moving the ultrasound device across substantially all of the anatomical area 205.

It should be appreciated that the example in FIG. 2 is non-limiting, and the predetermined path 207 can take other forms. For example, while the parallel legs of the predetermined path 207 are shown in FIG. 2 as proceeding downwards, the parallel legs of the predetermined path 207 may instead proceed downwards, leftwards, or rightwards. It should also be appreciated that the anatomical area 205 need not be the torso, but can be any anatomical area of the body, such as the abdomen, arm, breast, chest, foot, genitalia, hand, head, leg, neck, pelvis, and thorax. It should also be appreciated that the target anatomical view need not be a view of the heart, but may be a view of other structures and organs in the body.

Figure 3:
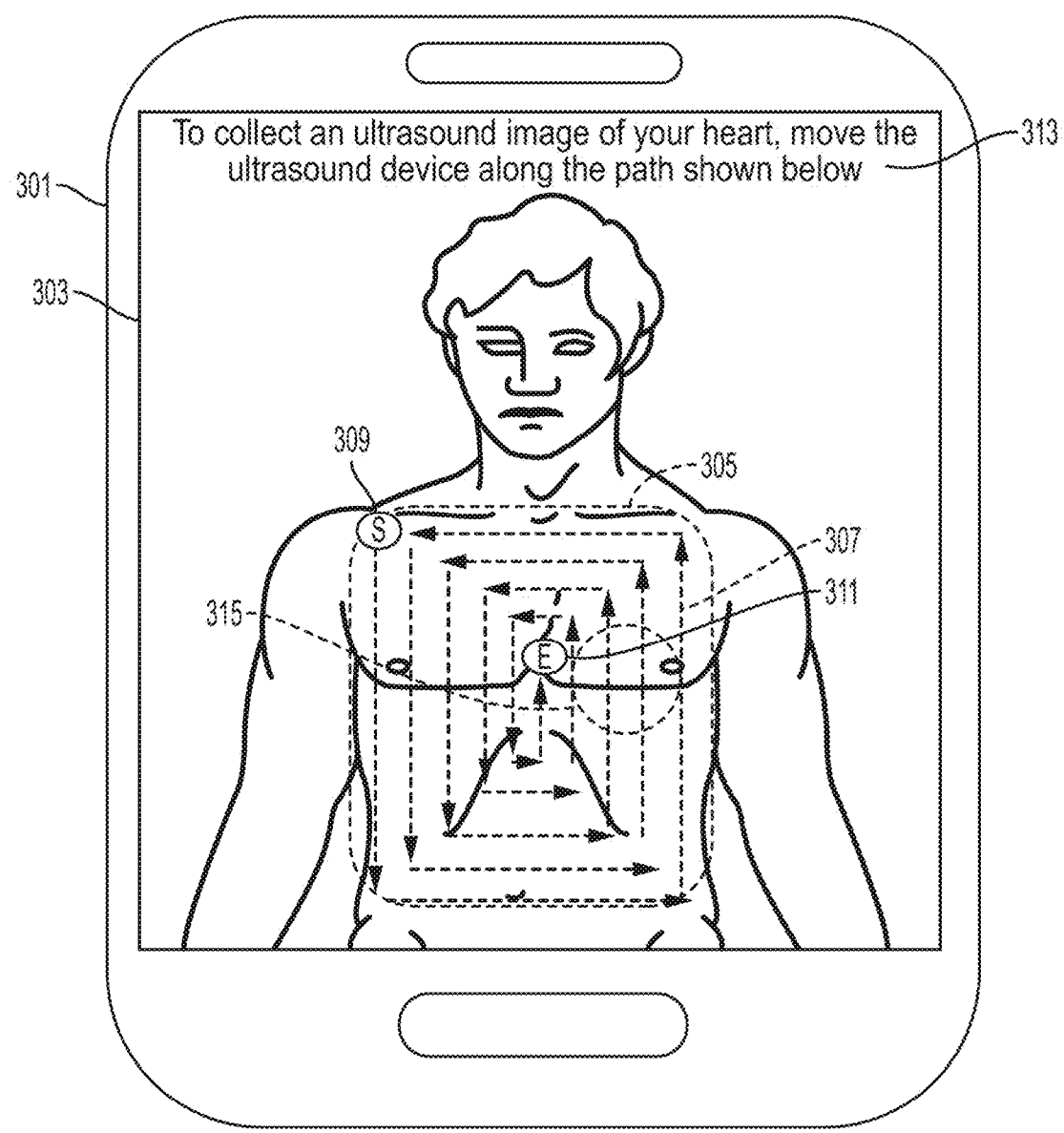
FIG. 3 shows another example of instructions for moving an ultrasound device along a predetermined path to collect ultrasound data capable of being transformed into an ultrasound image of a target anatomical view in accordance with certain embodiments disclosed herein.

FIG. 3 shows another example of instructions for moving an ultrasound device along a predetermined path to collect ultrasound data capable of being transformed into an ultrasound image of a target anatomical view ("target ultrasound data") in accordance with certain embodiments disclosed herein. FIG. 3 shows a host device 301 that includes a display 303. The display 303 displays an image of an anatomical area 305 (in the example of FIG. 3, the front surface of the torso). The display 303 also displays an image of a predetermined path 307 superimposed on the image of the anatomical area 305. The predetermined path 307 includes translational movement of the ultrasound device. The image of the predetermined path 307 includes an indication of a starting point 309 and an indication of an ending point 311 on the predetermined path 307. The display 303 also displays text 313 instructing the operator to collect an ultrasound image of the target anatomical view (in the example of FIG. 3, the heart) by moving an ultrasound device along the predetermined path 307. The instructions illustrated by FIG. 3 include the image of the anatomical area 305, the image of the predetermined path 307 (including the starting point 309 and the ending point 311), and the text 313.

In the example of FIG. 3, the predetermined path 307 is a path, and in particular a spiral path, that covers substantially all of the anatomical area 305. The shape of the predetermined path 307 may be helpful in that the operator need not necessarily lift the ultrasound device while moving the ultrasound device along the predetermined path 307. Additionally, the shape of the predetermined path 307 may be helpful in that the legs of the predetermined path 307 may become progressively shorter, which may be helpful in avoiding fatigue for the operator while the operator moves the ultrasound device along the predetermined path 307. It can be appreciated that in order to collect data capable of being transformed into an ultrasound image of the target anatomical view, which in the example of FIG. 3 is the heart, it may only be necessary to place the ultrasound device near a region 315 where the heart is located (assuming other requirements such as the tilt and the rotational orientation of the ultrasound device are fulfilled). However, providing instructions to place the ultrasound device near the region 315 may be difficult, as precisely and efficiently describing the region 315 visually or with words may be difficult. On the other hand, the instructions of FIG. 3 to move the ultrasound device along the predetermined path 307, which instruct the operator to move the ultrasound device across substantially all of the anatomical area 305, may be easier to describe and follow than specific instructions to place the ultrasound device at the region 315. Furthermore, moving the ultrasound device along the predetermined path 307 should result in the ultrasound device collecting the target ultrasound data when the ultrasound device moves over the region 315 along the predetermined path 307 (assuming other requirements such as the ultrasound device's tilt and rotational orientation are fulfilled). As a side effect of moving the ultrasound device along the predetermined path 307, non-target ultrasound data may be collected when the ultrasound device moves over other regions along the predetermined path 307.

In some embodiments, the host device 301 may be a mobile smartphone, a tablet, a laptop, a smart watch, a virtual reality (VR) headset, an augmented reality (AR) headset, or a smart wearable device. In some embodiments, the indication of the starting point 309 and the indication of the ending point 311 may not be displayed on the display 303, but instead the operator may choose where to begin and end moving the ultrasound device along the predetermined path 307. In some embodiments, the text 313 may display different text with the same general meaning as the text 313 shown in FIG. 3. In some embodiments, the text 313 may not be displayed, but instead may be played by the host device 301 as audio. In some embodiments, the text 313 may be absent.

It should be appreciated that the image of the predetermined path 307 may not be intended to be followed exactly. Rather, the image of the predetermined path 307 may be intended to simply illustrate a spiral path that covers substantially all of the anatomical area 305. For example, gaps between various legs of the image of the predetermined path 307 may be displayed due to resolution constraints of the display 303, and the instructions may not intend for the operator to skip these gaps when moving the ultrasound device across substantially all of the anatomical area 305.

It should be appreciated that the example in FIG. 3 is non-limiting, and the predetermined path 307 can take other forms. For example, the starting point 309 and the ending point 311 may be at other locations than those shown in FIG. 3. Additionally, for example, while the predetermined path 307 is shown in FIG. 3 as proceeding initially downwards and rightwards, the predetermined path 307 may proceed initially upwards and/or leftwards. It should also be appreciated that the anatomical area 305 need not be the torso, but can be any anatomical area of the body, such as the abdomen, arm, breast, chest, foot, genitalia, hand, head, leg, neck, pelvis, and thorax. It should also be appreciated that the target anatomical view need not be a view of the heart, but may be a view of other structures and organs in the body.

Figure 4:
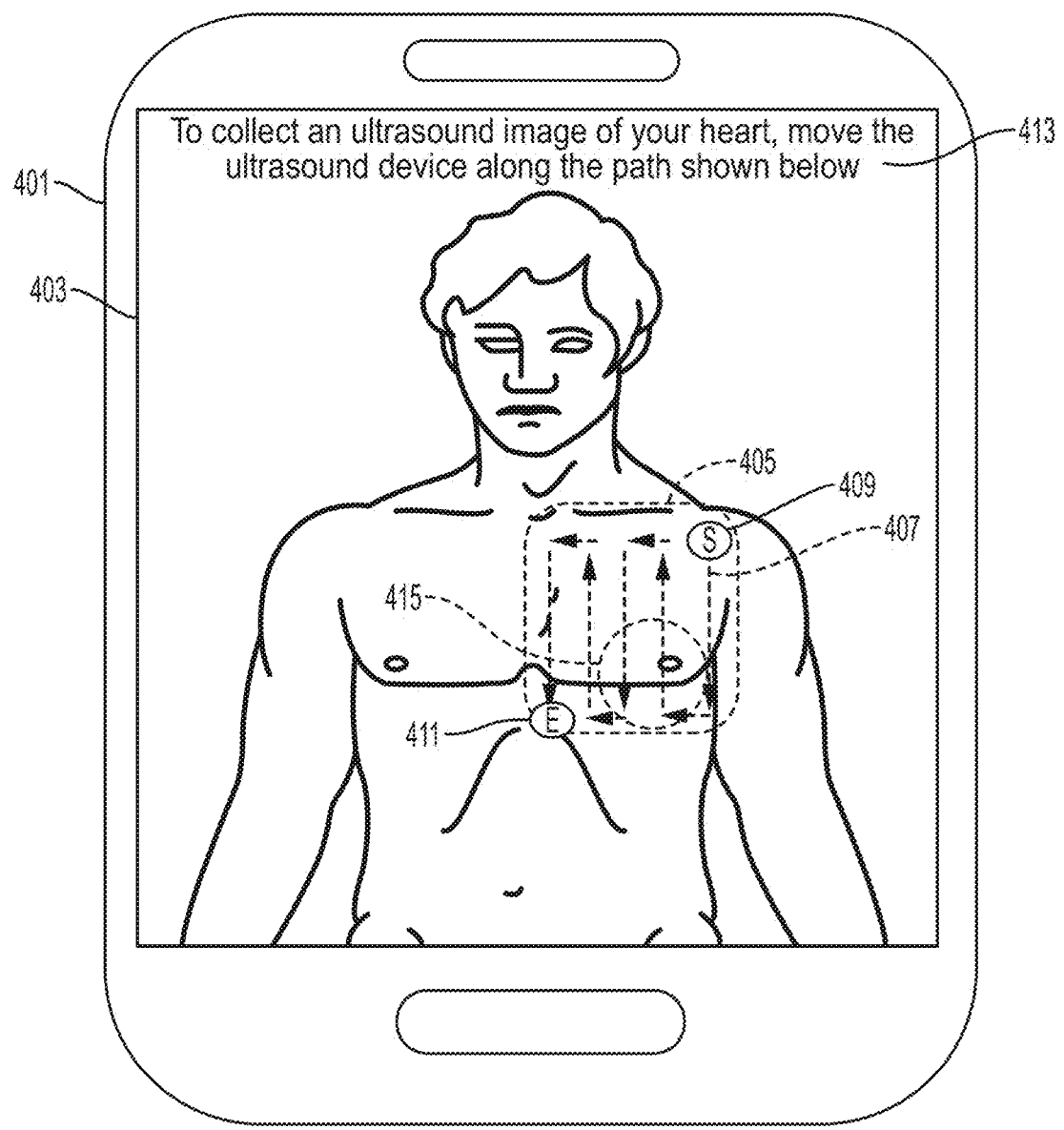
FIG. 4 shows another example of instructions for moving an ultrasound device along a predetermined path to collect ultrasound data capable of being transformed into an ultrasound image of a target anatomical view in accordance with certain embodiments disclosed herein.

FIG. 4 shows an example of instructions for moving an ultrasound device along a predetermined path to collect ultrasound data capable of being transformed into an ultrasound image of a target anatomical view ("target ultrasound data") in accordance with certain embodiments disclosed herein. FIG. 4 shows a host device 401 that includes a display 403. The display 403 displays an image of an anatomical area 405 (in the example of FIG. 4, the front surface of the upper-left torso). The display 403 also displays an image of a predetermined path 407 superimposed on the image of the anatomical area 405. The predetermined path 407 includes translational movement of the ultrasound device. The image of the predetermined path 407 includes an indication of a starting point 409 and an indication of an ending point 411 on the predetermined path 407. The display 403 also displays text 413 instructing the operator to collect an ultrasound image of the target anatomical view (in the example of FIG. 4, the heart) by moving an ultrasound device along the predetermined path 407. The instructions illustrated by FIG. 4 include the image of the anatomical area 405, the image of the predetermined path 407 (including the starting point 409 and the ending point 411), and the text 413.

In the example of FIG. 4, the predetermined path 407 is a path, and in particular a serpentine path, that covers substantially all of the anatomical area 405. It can be appreciated that in order to collect data capable of being transformed into an ultrasound image of the target anatomical view, which in the example of FIG. 4 is the heart, it may only be necessary to place the ultrasound device near a region 415 where the heart is located (assuming other requirements such as the tilt and the rotational orientation of the ultrasound device are fulfilled). However, providing instructions to place the ultrasound device near the region 415 may be difficult, as precisely and efficiently describing the region 415 visually or with words may be difficult. On the other hand, the instructions of FIG. 4 to move the ultrasound device along the predetermined path 407, which instruct the operator to move the ultrasound device across substantially all of the anatomical area 405, may be easier to describe and follow than specific instructions to place the ultrasound device at the region 415. Furthermore, moving the ultrasound device along the predetermined path 407 should result in the ultrasound device collecting the target ultrasound data when the ultrasound device moves over the region 415 along the predetermined path 407 (assuming other requirements such as the ultrasound device's tilt and rotational orientation are fulfilled). As a side effect of moving the ultrasound device along the predetermined path 407, non-target ultrasound data may be collected when the ultrasound device moves over other regions along the predetermined path 407.

It should be appreciated that in contrast to the predetermined path 107 shown in FIG. 1, which covers substantially all of the torso, the predetermined path 407 shown in FIG. 4 only covers the upper-left portion of the torso. By covering a smaller area, the predetermined path 407 may be helpful in avoiding fatigue for the operator while moving the ultrasound device along the predetermined path 407. It should be appreciated that a predetermined path need not substantially cover all of a well-defined anatomical area (e.g., a surface of the abdomen, arm, breast, chest, foot, genitalia, hand, head, leg, neck, pelvis, thorax, or torso), but may cover a portion thereof, or may cross any portion of the human body. In some embodiments, the predetermined path includes a single sweep across a portion of an anatomical area (e.g., a downward sweep down the center of the chest). In some embodiments, the host device 401 may be a mobile smartphone, a tablet, a laptop, a smart watch, a virtual reality (VR) headset, an augmented reality (AR) headset, or a smart wearable device. In some embodiments, the indication of the starting point 409 and the indication of the ending point 411 may not be displayed on the display 403, but instead the operator may choose where to begin and end moving the ultrasound device along the predetermined path 407. In some embodiments, the text 413 may display different text with the same general meaning as the text 413 shown in FIG. 4. In some embodiments, the text 413 may not be displayed, but instead may be played by the host device 401 as audio. In some embodiments, the text 413 may be absent.

It should be appreciated that the image of the predetermined path 407 may not be intended to be followed exactly. Rather, the image of the predetermined path 407 may be intended to simply illustrate a serpentine path that covers substantially all of the anatomical area 405. For example, gaps between various legs of the image of the predetermined path 407 may be displayed due to resolution constraints of the display 403, and the instructions may not intend for the operator to skip these gaps when moving the ultrasound device across substantially all of the anatomical area 405.

It should be appreciated that the example in FIG. 4 is non-limiting, and the predetermined path 407 can take other forms. For example, the starting point 409 and the ending point 411 may be at other locations than those shown in FIG. 4. Additionally, for example, while the predetermined path 407 is shown in FIG. 4 as proceeding initially downwards and rightwards, the predetermined path 407 may proceed initially upwards and/or leftwards. Additionally, for example, while the predetermined path 407 is shown in FIG. 4 as proceeding substantially upwards and downwards across the anatomical area 405, the predetermined path 407 may proceed substantially rightwards and leftwards across the anatomical area 405. It should also be appreciated that the anatomical area 405 need not be the torso, but can be any anatomical area of the body, such as the thorax, abdomen, uterus, limbs, head, and neck. It should also be appreciated that the target anatomical view need not be a view of the heart, but may be a view of other structures and organs in the body.

FIGS. 1-4 show examples of instructions that take the form of an image displayed on a host device. Such images may be predetermined in that they may be generated based on the target ultrasound data to be collected prior to the operator beginning to collect ultrasound data. In some embodiments, the instructions may take the form of a predetermined video. In some embodiments, the predetermined video may show an ultrasound device moving along the predetermined path.

Figure 5:
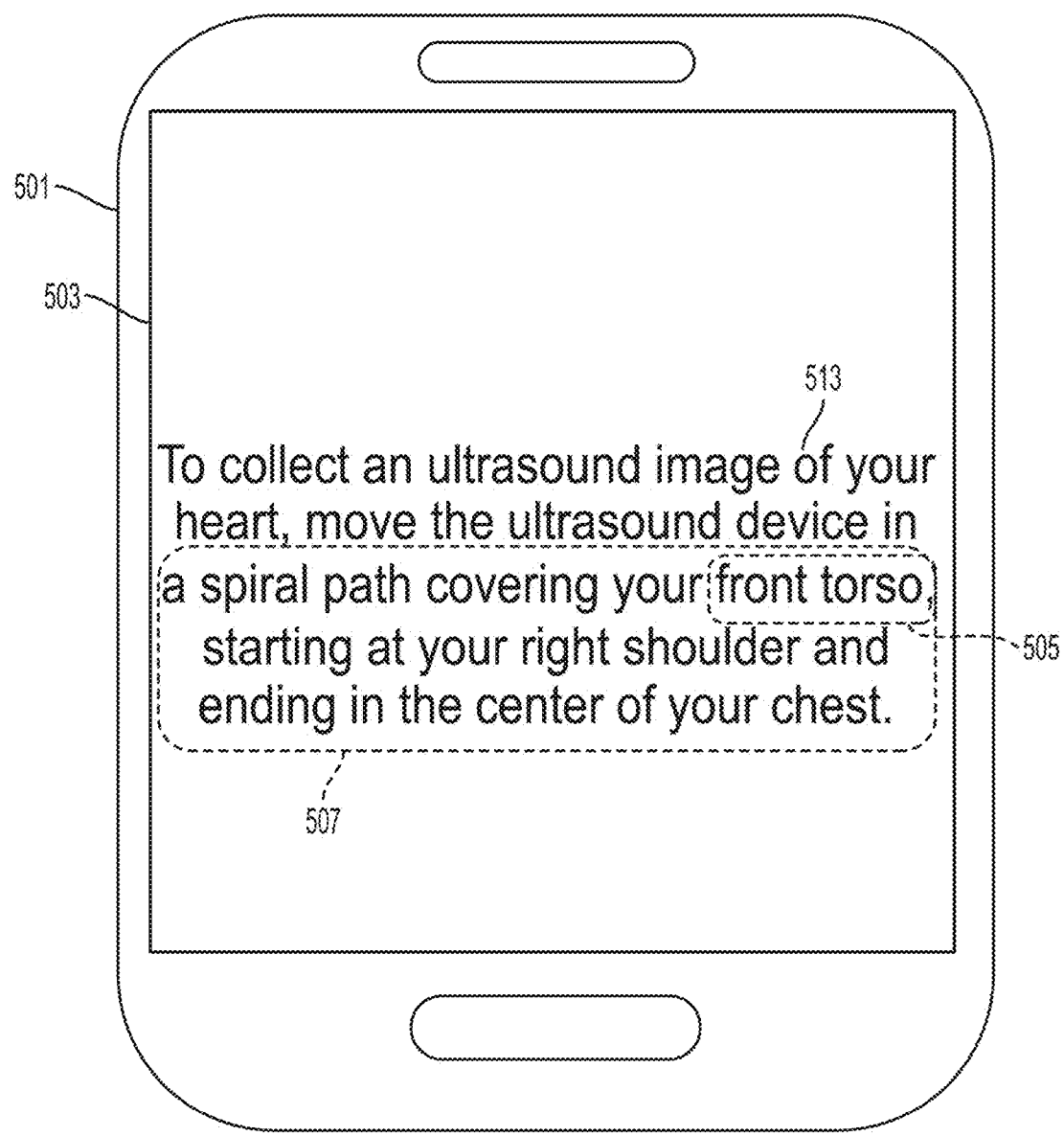
FIG. 5 shows another example of instructions for moving an ultrasound device along a predetermined path to collect ultrasound data capable of being transformed into an ultrasound image of a target anatomical view in accordance with certain embodiments disclosed herein.

FIG. 5 shows another example of instructions for moving an ultrasound device along a predetermined path to collect ultrasound data capable of being transformed into an ultrasound image of a target anatomical view ("target ultrasound data") in accordance with certain embodiments disclosed herein. FIG. 5 shows a host device 501 that includes a display 503. The display 503 displays text 513 instructing the user to collect an ultrasound image of the target anatomical view (in the example of FIG. 5, the heart) by moving an ultrasound device along a predetermined path 507 relative to an anatomical area 505 (in the example of FIG. 5, the front surface of the torso). The predetermined path 507 includes translational movement of the ultrasound device. The instructions illustrated by FIG. 5 include the text 513.

In the example of FIG. 5, the predetermined path 507 is a path that covers substantially all of the anatomical area 505. It can be appreciated that in order to collect data capable of being transformed into an ultrasound image of the target anatomical view, which in the example of FIG. 5 is the heart, it may only be necessary to place the ultrasound device near a specific target region in the anatomical area 505 where the heart is located (assuming other requirements such as the tilt and the rotational orientation of the ultrasound device are fulfilled). However, providing instructions to place the ultrasound device near the region 515 may be difficult, as precisely and efficiently describing the region 515 visually or with words may be difficult. On the other hand, the instructions of FIG. 5 to move the ultrasound device along the predetermined path 507, which instruct the operator to move the ultrasound device across substantially all of the anatomical area 505, may be easier to describe and follow than specific instructions to place the ultrasound device at the region 515. Furthermore, moving the ultrasound device along the predetermined path 507 should result in the ultrasound device collecting the target ultrasound data when the ultrasound device moves over the region 515 along the predetermined path 507 (assuming other requirements such as the ultrasound device's tilt and rotational orientation are fulfilled). As a side effect of moving the ultrasound device along the predetermined path 507, non-target ultrasound data may be collected when the ultrasound device moves over other regions along the predetermined path 507.

In some embodiments, the host device 501 may be a mobile smartphone, a tablet, a laptop, a smart watch, a virtual reality (VR) headset, an augmented reality (AR) headset, or a smart wearable device. In some embodiments, the text 513 may display different text with the same general meaning as the text 513 shown in FIG. 5. In some embodiments, the text 513 may include more detail, such as describing the kind of path (serpentine, spiral, etc.), where to begin the path, where to end the path, which direction the predetermined path 507 should follow, etc.

It should be appreciated that the example in FIG. 5 is non-limiting, and the anatomical area 505 need not be the torso, but can be any anatomical area of the body, such as the abdomen, arm, breast, chest, foot, genitalia, hand, head, leg, neck, pelvis, and thorax. It should also be appreciated that the target anatomical view need not be a view of the heart, but may be a view of other structures and organs in the body.

Figure 6:
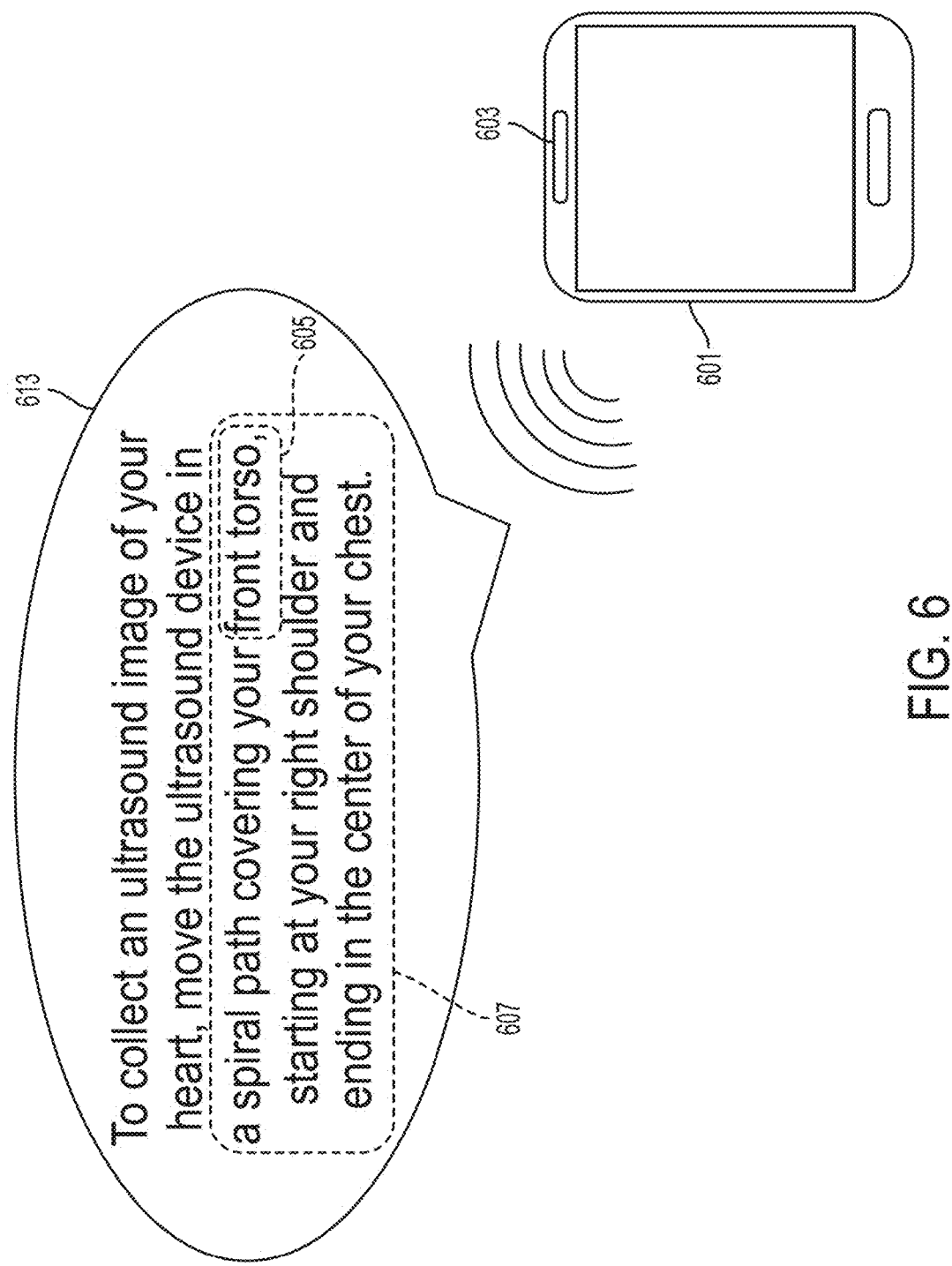
FIG. 6 shows another example of instructions for moving an ultrasound device along a predetermined path to collect ultrasound data capable of being transformed into an ultrasound image of a target anatomical view in accordance with certain embodiments disclosed herein.

FIG. 6 shows another example of instructions for moving an ultrasound device along a predetermined path to collect ultrasound data capable of being transformed into an ultrasound image of a target anatomical view ("target ultrasound data") in accordance with certain embodiments disclosed herein. FIG. 6 shows a host device 601 that includes a speaker 603. The speaker 603 outputs audio 613 instructing the user to collect an ultrasound image of the target anatomical view (in the example of FIG. 6, the heart) by moving an ultrasound device along a predetermined path 607 relative to anatomical area 605 (in the example of FIG. 6, the front surface of the torso). The predetermined path 607 includes translational movement of the ultrasound device. The instructions illustrated by FIG. 6 include the audio 613.

In the example of FIG. 6, the predetermined path 607 is a path that covers substantially all of the anatomical area 605. It can be appreciated that in order to collect data capable of being transformed into an ultrasound image of the target anatomical view, which in the example of FIG. 6 is the heart, it may only be necessary to place the ultrasound device near a specific target region in the anatomical area 605 where the heart is located (assuming other requirements such as the tilt and the rotational orientation of the ultrasound device are fulfilled). However, providing instructions to place the ultrasound device near the specific target region may be difficult, as precisely and efficiently describing the specific target region visually or with words may be difficult. On the other hand, the instructions of FIG. 6 to move the ultrasound device along the predetermined path 607, which instruct the operator to move the ultrasound device across substantially all of the anatomical area 605, may be easier to describe and follow than specific instructions to place the ultrasound device at the specific target region. Furthermore, moving the ultrasound device along the predetermined path 607 should result in the ultrasound device collecting the target ultrasound data when the ultrasound device moves over the specific target region along the predetermined path 607 (assuming other requirements such as the ultrasound device's tilt and rotational orientation are fulfilled). As a side effect of moving the ultrasound device along the predetermined path 607, non-target ultrasound data may be collected when the ultrasound device moves over other regions along the predetermined path 607.

In some embodiments, the host device 601 may be a mobile smartphone, a tablet, a laptop, a smart watch, a virtual reality (VR) headset, an augmented reality (AR) headset, or a smart wearable device. In some embodiments, the audio 613 may include different instructions with the same general meaning as the audio 613 shown in FIG. 6. In some embodiments, the audio 613 may include more detail, such as describing the kind of path (serpentine, spiral, etc.), where to begin the path, where to end the path, which direction the predetermined path 607 should follow, etc.

It should be appreciated that the example in FIG. 6 is non-limiting, and the anatomical area 605 need not be the torso, but can be any anatomical area of the body, such as the abdomen, arm, breast, chest, foot, genitalia, hand, head, leg, neck, pelvis, and thorax. It should also be appreciated that the target anatomical view need not be a view of the heart, but may be a view of other structures and organs in the body.

FIGS. 5-6 show instructions that take the form of instructions expressed in words. Such images may be predetermined in that the instructions may be generated based on the target ultrasound data to be collected prior to the operator beginning to collect ultrasound data. Instructions expressed in words may be easier for certain operators to understand and follow.

FIGS. 1-6 illustrate instructions for moving an ultrasound device across substantially all of an anatomical area. In some embodiments, moving an ultrasound device across substantially all of an anatomical area may mean moving the ultrasound device such that the sensor of the ultrasound device, or an acoustic lens that covers the sensor, contacts substantially all of the surface area of the anatomical area. In some embodiments, the instructions for moving the ultrasound device across substantially all of the anatomical area may include instructions (e.g., visual, textual, and/or audio instructions) to move the ultrasound device such that the sensor contacts substantially all of the surface area of the anatomical area. In some embodiments, when instructing the operator to move the ultrasound device across substantially all of an anatomical area, the anatomical area may be greater in area than 1 cm$^2$, 5 cm$^2$, 10 cm$^2$, 25 cm$^2$, 50 cm$^2$, 100 cm$^2$, 500 cm$^2$, 1000 cm$^2$, 5000 cm$^2$, 1 m$^2$, or any other suitable area. In some embodiments, the instructions may be to move the ultrasound device across substantially all of an anatomical area having a well-defined name. In some embodiments, the instructions may be to move the ultrasound device across substantially all of a surface (e.g., front, left, right, back) of a subject's abdomen, arm, breast, chest, foot, genitalia, hand, head, leg, neck, pelvis, thorax, or torso. In some embodiments, the instructions may be to move the ultrasound device across substantially of a portion of an anatomical area, such as the top, bottom, left, and/or right portion of a surface of a subject's abdomen, arm, breast, chest, foot, genitalia, hand, head, leg, neck, pelvis, thorax, or torso.

In some embodiments, a host device may instruct the user, prior to providing instructions to move an ultrasound device along a predetermined path, such as those shown in FIGS. 1-6, to place the ultrasound device at a particular target tilt (i.e., a particular angle formed by the ultrasound device relative to a plane formed by the subject) and at a particular target rotational orientation about its longitudinal axis relative to the subject. To provide instructions for placing the ultrasound device at the target tilt and the target rotational orientation, the host device may receive motion and/or orientation data from the ultrasound device. The ultrasound device may include a motion and/or orientation sensor configured to generate motion and/or orientation data regarding the ultrasound device. For example, the motion and/or orientation sensor may be configured to generate to generate data regarding acceleration of the ultrasound device, data regarding angular velocity of the ultrasound device, and/or data regarding magnetic force acting on the ultrasound device (which, due to the magnetic field of the earth, may be indicative of orientation relative to the earth). The ultrasound device may include an accelerometer, a gyroscope, and/or a magnetometer, and these devices may be used by the ultrasound device to generate the motion and/or orientation data. The host device may determine, based on the motion and/or orientation data, whether the ultrasound device is at the target tilt and/or target rotational orientation. The host device may determine the current tilt and rotational orientation of the ultrasound device based on the motion and/or orientation data, compare the current tilt and rotational orientation to the target tilt and rotational orientation, and determine whether there are differences between the current tilt and rotational orientation and the target tilt and rotational orientation.

If the host device determines that there are differences between the current tilt and rotational orientation and the target tilt and rotational orientation (i.e., the ultrasound device is not at the target tilt and rotational orientation), the host device may provide an instruction for moving the ultrasound device to the target tilt and rotational orientation based on the motion and/or orientation data. For example, based on the differences between the current tilt and rotational orientation and the default tilt and rotational orientation of the ultrasound device, the host device may determine instructions for eliminating those differences (e.g., tilting or rotating the ultrasound device). To provide the instruction for moving the ultrasound device to the target tilt and rotational orientation, the host device may display the instruction on a display screen of the host device. For example, if the host device is a smartphone coupled to the ultrasound device by a cable, the smartphone may display the instruction on its display screen. The displayed instruction may include any combination of words (e.g., "Rotate the probe clockwise") and directional indicators. The host device may display directional indicators on an image of the ultrasound device and/or the subject. In some embodiments, the host device may receive or capture a real-time video of the ultrasound device and/or the subject and display directional indicators superimposed on the video of the ultrasound device and/or the subject in real-time, where the direction of the directional indicators indicates the direction in which the ultrasound device should be moved relative to the subject. This may be considered an augmented reality display. In some embodiments, the host device may generate audio containing the instructions from speakers (e.g., speakers included in the host device).

Figure 7:
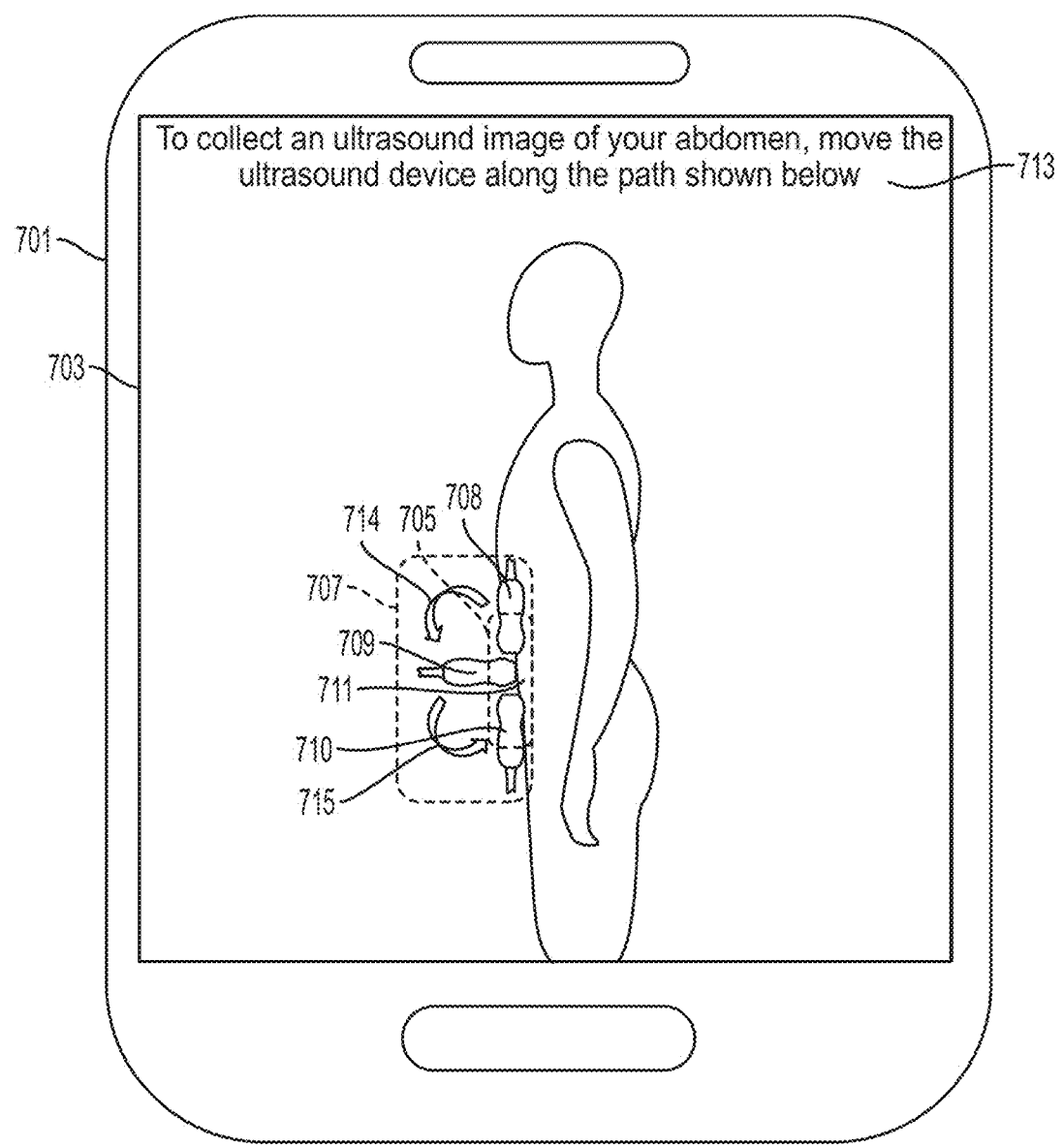
FIG. 7 shows another example of instructions for moving an ultrasound device along a predetermined path to collect ultrasound data capable of being transformed into an ultrasound image of a target anatomical view in accordance with certain embodiments disclosed herein.

FIG. 7 shows another example of instructions for moving an ultrasound device along a predetermined path to collect ultrasound data capable of being transformed into an ultrasound image of a target anatomical view ("target ultrasound data") in accordance with certain embodiments disclosed herein. FIG. 7 shows a host device 701 that includes a display 703. The display 703 displays an image of an anatomical area 705 (in the example of FIG. 7, the front surface of the abdomen). The display 703 also displays an image of a predetermined path 707 adjacent to the image of the anatomical area 705. The predetermined path 707 includes pivoting an ultrasound device about a location 711 within the anatomical area 705, where the sensor of the ultrasound device (or portions thereof) remains substantially in contact with the location 711 during the pivoting. The image of the predetermined path 707 includes three images of positions 708-710 of the ultrasound device relative to the anatomical area 705 that are assumed by the ultrasound device when moving along the predetermined path 707, and arrows 714 and 715 showing a direction of the ultrasound device moving from position 708 to position 709 and from position 709 to position 710. The display 703 also displays text 713 instructing the user to collect an ultrasound image of the target anatomical view (in the example of FIG. 7, the abdomen) by moving an ultrasound device along the predetermined path 707. The instructions illustrated by FIG. 7 include the image of the anatomical area 705, the image of the predetermined path 707, the images of the positions 708-710, the arrows 714 and 715, and the text 713.

In the example of FIG. 7, the predetermined path 707 is a path along which the ultrasound device pivots substantially through 180 degrees about the location 711 within the anatomical area 705. It can be appreciated that in order to collect data capable of being transformed into an ultrasound image of the target anatomical view, which in the example of FIG. 7 is the abdomen, it may be necessary to place the ultrasound device at the location 711 and at a particular tilt relative to the abdomen. The particular tilt may require that the ultrasound device be positioned at a particular angle relative to a plane formed by the subject at the location 711. However, providing instructions to place the ultrasound device at the particular tilt may be difficult, as precisely and efficiently describing the tilt visually or with words may be difficult. On the other hand, the instructions of FIG. 7 to move the ultrasound device along the predetermined path 707, which instruct the operator to pivot the ultrasound device substantially through 180 degrees about the location 711, may be easier to describe and follow than specific instructions to place the ultrasound device at the particular orientation. Furthermore, moving the ultrasound device along the predetermined path 707 should result in the ultrasound device collecting the target ultrasound data when the ultrasound device is pivoted to the particular tilt relative to the location 711 within the 180 degree pivot described by the predetermined path 707 about the location 711 (assuming other requirements such as the ultrasound device's location and rotational orientation are fulfilled). As a side effect of moving the ultrasound device along the predetermined path 707, non-target ultrasound data may be collected when the ultrasound device pivots through other tilts relative to the location 711 along the predetermined path 707. In some embodiments, in order to instruct the user to initially place the ultrasound device at the location 711, the host device 701 may instruct the user, prior to providing instructions to move the ultrasound device along the predetermined path 707, to place the ultrasound device at the location 711. The location 711 may be an easily described anatomical landmark, such as the navel, a particular nipple, a particular knuckle, a particular knee, a particular elbow, a particular shoulder, a particular toe, a particular ankle, a particular bone, etc. In some embodiments, the host device 701 may instruct the user, prior to providing instructions to move the ultrasound device along the predetermined path 707, to place the ultrasound device at a particular rotational orientation (i.e., a particular rotation about the ultrasound device's longitudinal axis) at the location 711. In some embodiments, the predetermined path 707 may include pivoting the ultrasound device through less than 180 degrees, e.g., 150 degrees, 120 degrees, 90 degrees, 60 degrees, 30 degrees, or any suitable number of degrees. In some embodiments, the host device 701 may instruct the user to pivot the ultrasound device to cover as many possible pivot orientations in three-dimensional space about location 711 as possible.

In some embodiments, the host device 701 may be a mobile smartphone, a tablet, a laptop, a smart watch, a virtual reality (VR) headset, an augmented reality (AR) headset, or a smart wearable device. In some embodiments, the text 713 may display different text with the same general meaning as the text 713 shown in FIG. 7. In some embodiments, the text 713 may not be displayed, but instead may be played by the host device 701 as audio. In some embodiments, the text 713 may be absent. In some embodiments, more or fewer than the three images of the positions 708-710 may be shown. In some embodiments, more or fewer than the two arrows 714 and 715 may be shown.

It should be appreciated that the image of the predetermined path 707 may not be intended to be followed exactly. Rather, the image of the predetermined path 707 may be intended to simply illustrate a path that includes pivoting the ultrasound device through 180 degrees about the location 711. For example, the operator may not necessarily need to exactly follow the sequence shown by the images of the positions 708-710 and the arrows 714 and 715.

It should be appreciated that the example in FIG. 7 is non-limiting, and the predetermined path 707 can take other forms. For example, the predetermined path 707 may proceed in a different direction than shown by the images of the positions 708-710 and the arrows 714 and 715. It should also be appreciated that the anatomical area 705 need not be the abdomen, but can be any anatomical area of the body, such as the arm, breast, chest, foot, genitalia, hand, head, leg, neck, pelvis, thorax, and torso. It should also be appreciated that the target anatomical view need not be a view of the abdomen, but may be a view of other areas, structures, and organs in the body.

Figure 8:
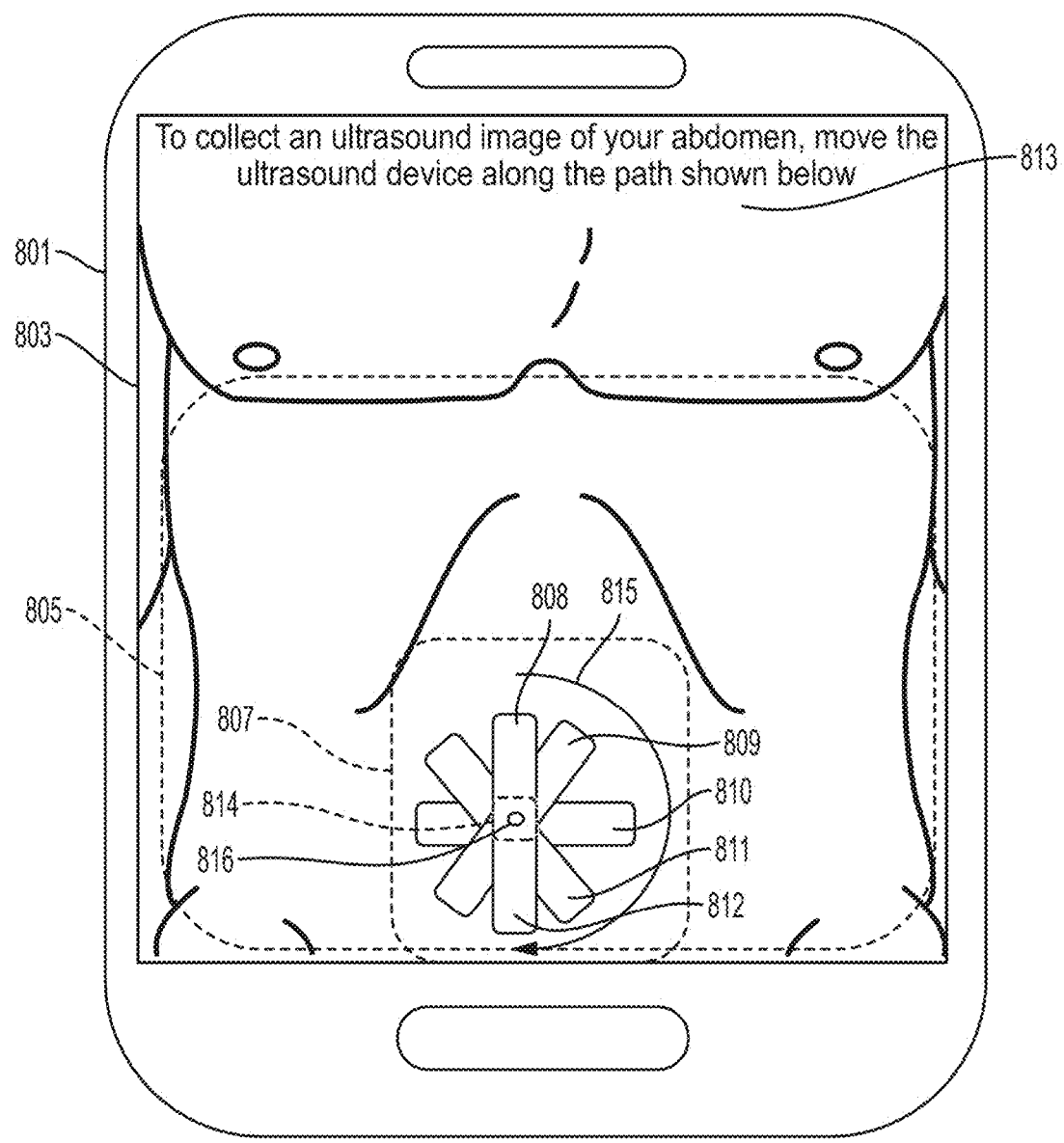
FIG. 8 shows another example of instructions for moving an ultrasound device along a predetermined path to collect ultrasound data capable of being transformed into an ultrasound image of a target anatomical view in accordance with certain embodiments disclosed herein.

FIG. 8 shows another example of instructions for moving an ultrasound device along a predetermined path to collect ultrasound data capable of being transformed into an ultrasound image of a target anatomical view ("target ultrasound data") in accordance with certain embodiments disclosed herein. FIG. 8 shows a host device 801 that includes a display 803. The display 803 displays an image of an anatomical area 805 (in the example of FIG. 8, the front surface of the abdomen). The display 803 also displays an image of a predetermined path 807 superimposed on the image of the anatomical area 805. The predetermined path 807 includes rotating an ultrasound device about its longitudinal axis 816 at a location 814 within the anatomical area 805. The longitudinal axis 816 is shows as a dot indicating that the longitudinal axis 816 goes into and comes out of the plane of the figure. The image of the predetermined path 807 includes five images of positions 808-812 of the ultrasound device relative to the anatomical area 805 that are assumed by the ultrasound device when moving along the predetermined path 807, and an arrow 815 showing a direction of the ultrasound device moving from position 808 to position 809, from position 809 to position 810, from position 810 to position 811, and from position 811 to position 812. The images of the positions 808-812 represent the outline of the sensor of the ultrasound device relative to the anatomical area 805 when the ultrasound device assumes the positions 808-812. The position 808 and the position 812 appear the same in FIG. 8 because in positions 808 and 812, the ultrasound device is in substantially the same position but rotated 180 degrees. The display 803 also displays text 813 instructing the user to collect an ultrasound image of the target anatomical view (in the example of FIG. 8, the abdomen) by moving an ultrasound device along the predetermined path 807. The instructions illustrated by FIG. 8 include the image of the anatomical area 805, the image of the predetermined path 807, the images of the positions 808-812, the arrow 815, and the text 813.

In the example of FIG. 8, the predetermined path 807 is a path along which the ultrasound device rotates substantially through 180 degrees about its longitudinal axis 816. It can be appreciated that in order to collect data capable of being transformed into an ultrasound image of the target anatomical view, which in the example of FIG. 8 is the abdomen, it may be necessary to place the ultrasound device at the location 814 and at a particular rotational orientation about its longitudinal axis 816 relative to the anatomical area 805. However, providing instructions to place the ultrasound device at the particular rotational orientation may be difficult, as precisely and efficiently describing the rotational orientation visually or with words may be difficult. On the other hand, the instructions of FIG. 8 to move the ultrasound device along the predetermined path 807, which instruct the operator to rotate the ultrasound device substantially through 180 degrees about its longitudinal axis 816, may be easier to describe and follow than specific instructions to place the ultrasound device at the particular orientation. Furthermore, moving the ultrasound device along the predetermined path 807 should result in the ultrasound device collecting the target ultrasound data when the ultrasound device is rotated to the particular rotational orientation about its longitudinal axis 816 within the 180 degree rotation of the predetermined path 807 (assuming other requirements such as the ultrasound device's location and tilt are fulfilled). As a side effect of moving the ultrasound device along the predetermined path 807, non-target ultrasound data may be collected when the ultrasound device rotates through other orientations about the longitudinal axis 816 along the predetermined path 807. In some embodiments, in order to instruct the user to initially place the ultrasound device at the location 814, the host device 801 may instruct the user, prior to providing instructions to move the ultrasound device along the predetermined path 807, to place the ultrasound device at the location 814. The location 814 may be an easily described anatomical landmark, such as the navel, a particular nipple, a particular knuckle, a particular knee, a particular elbow, a particular shoulder, a particular toe, a particular ankle, a particular bone, etc. In some embodiments, the host device 801 may instruct the user, prior to providing instructions to move the ultrasound device along the predetermined path 807, to place the ultrasound device at a particular tilt (i.e., a particular angle formed by the ultrasound device relative to a plane formed by the subject at the location 814).

In some embodiments, the host device 801 may be a mobile smartphone, a tablet, a laptop, a smart watch, a virtual reality (VR) headset, an augmented reality (AR) headset, or a smart wearable device. In some embodiments, the text 813 may display different text with the same general meaning as the text 813 shown in FIG. 8. In some embodiments, the text 813 may not be displayed, but instead may be played by the host device 801 as audio. In some embodiments, the text 813 may be absent. In some embodiments, more or fewer than the five images of the positions 808-812 may be shown. In some embodiments, more than the one arrow 815 may be shown, or the arrow 815 may be absent.

It should be appreciated that the image of the predetermined path 807 may not be intended to be followed exactly. Rather, the image of the predetermined path 807 may be intended to simply illustrate a path that includes rotating the ultrasound device through 180 degrees about its longitudinal axis 816 at the location 815. For example, the operator may not necessarily need to exactly follow the sequence shown by the images of the positions 808-812 and the arrow 815.

It should be appreciated that the example in FIG. 8 is non-limiting, and the predetermined path 807 can take other forms. For example, the predetermined path 807 may proceed in a different direction than shown by the images of the positions 808-812 and the arrow 815. It should also be appreciated that the anatomical area 805 need not be the abdomen, but can be any anatomical area of the body, such as the arm, breast, chest, foot, genitalia, hand, head, leg, neck, pelvis, thorax, and torso. It should also be appreciated that the target anatomical view need not be a view of the abdomen, but may be a view of other areas, structures, and organs in the body. In some embodiments, the predetermined path 807 may include rotating the ultrasound device through less than 180 degrees, e.g., 150 degrees, 120 degrees, 90 degrees, 60 degrees, 30 degrees, or any suitable number of degrees.

Figure 9:
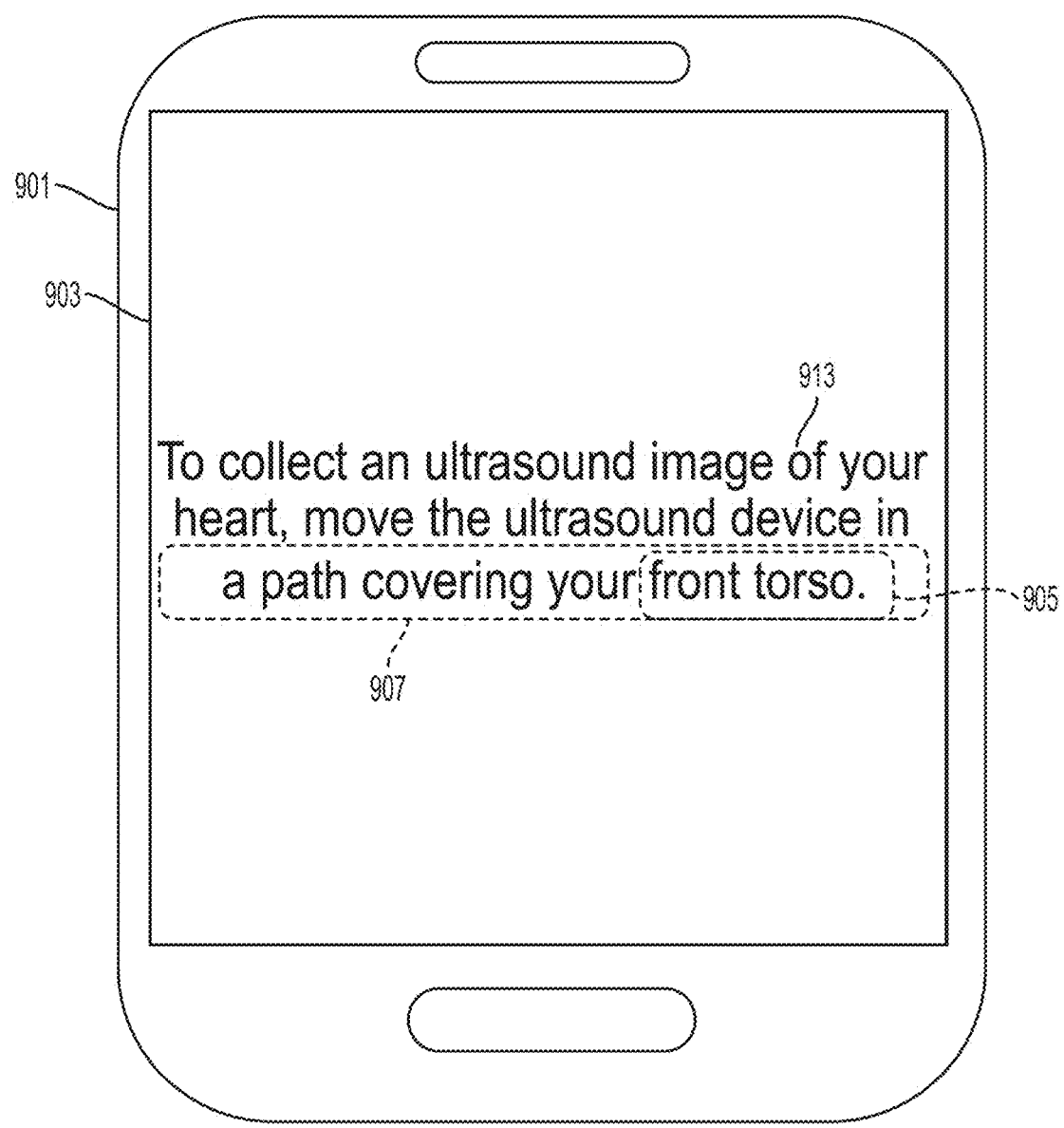
FIG. 9 shows an example of instructions for moving an ultrasound device along a path to collect ultrasound data capable of being transformed into an ultrasound image of a target anatomical view in accordance with certain embodiments disclosed herein.

FIG. 9 shows an example of instructions for moving an ultrasound device along a path to collect ultrasound data capable of being transformed into an ultrasound image of a target anatomical view ("target ultrasound data") in accordance with certain embodiments disclosed herein. FIG. 9 shows a host device 901 that includes a display 903. The display 903 displays text 913 instructing the user to collect an ultrasound image of the target anatomical view (in the example of FIG. 9, the heart) by moving an ultrasound device along a path 907 relative to an anatomical area 905 (in the example of FIG. 9, the front surface of the torso). The path 907 includes translational movement of the ultrasound device. The instructions illustrated by FIG. 9 include the text 913.

In the instructions of FIG. 9, instead of providing instructions to move an ultrasound device along a path of a specific form (e.g., with specific start/end points, specific directions, serpentine/spiral, etc.), the host device provides instructions to the operator to move the ultrasound device without specifying a form for the path, or without specifying some details of the form for the path. For example, the instructions in FIG. 9 omit images such as those shown in FIGS. 1-4 and 7-8 and omit verbal detail such as that shown in FIGS. 5-6 (i.e., "spiral," "starting at your right shoulder and ending in the center of your chest"). The operator may choose the specific form of the path 907 for moving the ultrasound device at the operator's discretion. Following instructions may be easier when the instructions provide the operator with freedom to choose the specific form of the path 907 rather than being instructed to follow a specific form of a path.

Conventional ultrasound systems provide feedback to the operator regarding collection of target ultrasound data while the operator moves an ultrasound device. For example, conventional ultrasound systems may display ultrasound images generated based on data being collected by the ultrasound device. In some embodiments, the host device 901 may not provide feedback to the operator regarding collection of the target ultrasound data while the operator moves the ultrasound device along the path 907. For example, the host device 901 may not display ultrasound images generated based on data collected by the ultrasound device while the ultrasound device moves along the path 907, may not provide an indication whether the ultrasound device is at or not at the target location (i.e., the location where ultrasound data capable of being transformed into an ultrasound image of a target anatomical view can be collected), may not provide an indication whether the ultrasound device is near or not near the target location, and may not provide guidance for moving the ultrasound device to the target location. Because the host device 901 may not provide feedback, the host device 901 may not need to store and run algorithms in real-time for providing feedback. The host devices in FIGS. 1-8 may likewise not provide feedback to the operator regarding collection of the target ultrasound data while the operator moves the ultrasound device.

In the example of FIG. 9, the path 907 is a path that covers substantially all of the anatomical area 905. It can be appreciated that in order to collect data capable of being transformed into an ultrasound image of the target anatomical view, which in the example of FIG. 9 is the heart, it may only be necessary to place the ultrasound device near a specific target region in the anatomical area 905 where the heart is located (assuming other requirements such as the tilt and the rotational orientation of the ultrasound device are fulfilled). However, providing instructions to place the ultrasound device near a particular region may be difficult, as precisely and efficiently describing the region visually or with words may be difficult. On the other hand, the instructions of FIG. 9 to move the ultrasound device along the path 907, which instruct the operator to move the ultrasound device across substantially all of the anatomical area 905, may be easier to describe and follow than specific instructions to place the ultrasound device at the particular region. Furthermore, moving the ultrasound device along the path 907 should result in the ultrasound device collecting the target ultrasound data when the ultrasound device moves over the particular region along the path 907 (assuming other requirements such as the ultrasound device's tilt and rotational orientation are fulfilled). As a side effect of moving the ultrasound device along the path 907, non-target ultrasound data may be collected when the ultrasound device moves over other regions along the path 907.

FIG. 9 illustrates instructions for moving an ultrasound device across substantially all of an anatomical area. In some embodiments, moving an ultrasound device across substantially all of an anatomical area may mean moving the ultrasound device such that the sensor of the ultrasound device, or an acoustic lens that covers the sensor, contacts substantially all of the surface area of the anatomical area. In some embodiments, the instructions for moving the ultrasound device across substantially all of the anatomical area may include instructions to move the ultrasound device such that the sensor contacts substantially all of the surface area of the anatomical area. In some embodiments, when instructing the operator to move the ultrasound device across substantially all of an anatomical area, the anatomical area may be greater in area than 1 cm2, 5 cm2, 10 cm2, 25 cm2, 50 cm2, 100 cm2, 500 cm2, 1000 cm2, 5000 cm2, 1 m2, or any other suitable area. In some embodiments, the instructions may be to move the ultrasound device across substantially all of an anatomical area having a well-defined name. In some embodiments, the instructions may be to move the ultrasound device across substantially all of a surface (e.g., front, left, right, back) of a subject's abdomen, arm, breast, chest, foot, genitalia, hand, head, leg, neck, pelvis, thorax, or torso. In some embodiments, the instructions may be to move the ultrasound device across substantially of a portion of an anatomical area, such as the top, bottom, left, and/or right portion of a surface of a subject's abdomen, arm, breast, chest, foot, genitalia, hand, head, leg, neck, pelvis, thorax, or torso.

In some embodiments, the instructions may be to move the ultrasound device along a path that include pivoting the ultrasound device and/or rotating the ultrasound device about its rotational axis, without specifying a form for the path, or without specifying some details of the form for the path. The operator may choose the specific form of the path for moving the ultrasound device at the operator's discretion. In some embodiments, the instructions may be to pivot the ultrasound device through 180 degrees, 150 degrees, 120 degrees, 90 degrees, 60 degrees, 30 degrees, or any suitable number of degrees. In some embodiments, the instructions may be to pivot the ultrasound device to cover as many possible pivot orientations as possible. In some embodiments, the instructions may be to rotate the ultrasound device through 180 degrees, 150 degrees, 120 degrees, 90 degrees, 60 degrees, 30 degrees, or any suitable number of degrees.

In some embodiments, the host device 901 may be a mobile smartphone, a tablet, a laptop, a smart watch, a virtual reality (VR) headset, an augmented reality (AR) headset, or a smart wearable device. In some embodiments, the text 913 may display different text with the same general meaning as the text 913 shown in FIG. 9.

It should be appreciated that the example in FIG. 9 is non-limiting, and the anatomical area 905 need not be the torso, but can be any anatomical area of the body, such as the abdomen, arm, breast, chest, foot, genitalia, hand, head, leg, neck, pelvis, and thorax. It should also be appreciated that the target anatomical view need not be a view of the heart, but may be a view of other structures and organs in the body.

In some embodiments, the host device may be configured to determine a predetermined path relative to an anatomical area in order to collect ultrasound data capable of being transformed into an ultrasound image of a target anatomical view. In some embodiments, a server may be configured to determine the predetermined path and transmit data representing the predetermined path to the host device for use in instructing the operator.

In some embodiments, the host device or the server may be configured to determine the predetermined path based on determining that a measure of ease of describing the predetermined path exceeds a threshold. In some embodiments, the threshold measure of ease may be a default value, or may be set by an external individual, or may be set by the operator of the ultrasound device. In some embodiments, the measure of ease may be a measure of ease of describing the predetermined path with words. For example, the measure of ease may be inversely related to how many words are necessary to describe the path. As a particular example, the host device may subtract the number of words necessary to describe the path from a predefined number, such as 20, in order to calculate the measure of ease. In some embodiments, a predetermined path including a location that has a specific name or verbal description may have a greater measure of ease than a predetermined path that does not include a location that has a specific name or verbal description. In some embodiments, the host device or server may be configured to access a database containing locations that have specific names or verbal descriptions when generating a predetermined path. In some embodiments, locations that are easier to describe (e.g., "torso") may have higher scores than locations that are harder to describe ("e.g., "upper left side of torso"), and the measure of ease of describing a predetermined path including a location having a higher score may be higher than a measure of ease of a predetermined path including a location having a lower score. In some embodiments, the host device or server may be configured to access a database containing scores for various locations when determining the measure of ease of describing a predetermined path.

In some embodiments, the measure of ease may be a measure of ease of describing the predetermined path visually. For example, a predetermined path covering substantially all of a visually well-defined anatomical area (e.g., a surface of the abdomen, arm, breast, chest, foot, genitalia, hand, head, leg, neck, pelvis, thorax, or torso) may have a larger measure of ease than a predetermined path that does not substantially cover all of a visually well-defined anatomical area. In some embodiments, a predetermined path crossing a location that has visually distinguishing features, or oriented, in an orientation that can be easily shown visually, relative to another location that does have visual distinguishing features, may have a higher measure of ease than a predetermined path not characterized by such. In some embodiments, the host device or server may be configured to access a database containing locations that are well-defined and/or have visually distinguishing features when generating a predetermined path. In some embodiments, locations that are well-defined and/or have more visually distinguishing features (e.g., "navel") may have higher scores than locations that are less well-defined and/or have fewer visually distinguishing features ("e.g., "upper left side of abdomen"), and the measure of ease of describing a predetermined path crossing or oriented, in an orientation that can be easily shown visually, relative to another location that has a higher score may be higher than a measure of ease of describing a predetermined path not characterized by such. In some embodiments, the host device or server may be configured to access a database containing scores for various locations when determining the measure of ease of describing a predetermined path. In some embodiments, the host device or the server may be configured to receive an image of the specific subject from whom the ultrasound data is being collected, and generate the predetermined path for the subject's specific anatomy based on the image.

In some embodiments, the host device or the server may be configured to access a database of predetermined paths for a given target location. For example, if the target ultrasound image is of the heart, the host device or the server may be configured to look up in the database of predetermined paths the predetermined path for collecting a target ultrasound image of the heart. In some embodiments, the operator may select (e.g., from a menu) the target ultrasound image needed, and the host device or the server may be configured to look up in the database of predetermined paths the predetermined path for collecting the selected target ultrasound image. In some embodiments, the host device may automatically select the target ultrasound image needed. In some embodiments, the retrieved predetermined path may be an image, video, and/or instructions expressed with words (e.g., audio or displayed text). In some embodiments, the host device or the server may be configured to receive an image of the specific subject from whom the ultrasound data is being collected, and superimpose an image and/or video of the predetermined path on the image of the specific subject. In some embodiments, a medical professional (e.g., a doctor, nurse, or imaging technician) or another individual may generate the predetermined path and load/cause to be loaded the predetermined path onto the host device. For example, an individual operating a remote processing device may select or generate the predetermined path and transmit the predetermined path to the host device local to the ultrasound device.

Figure 10:
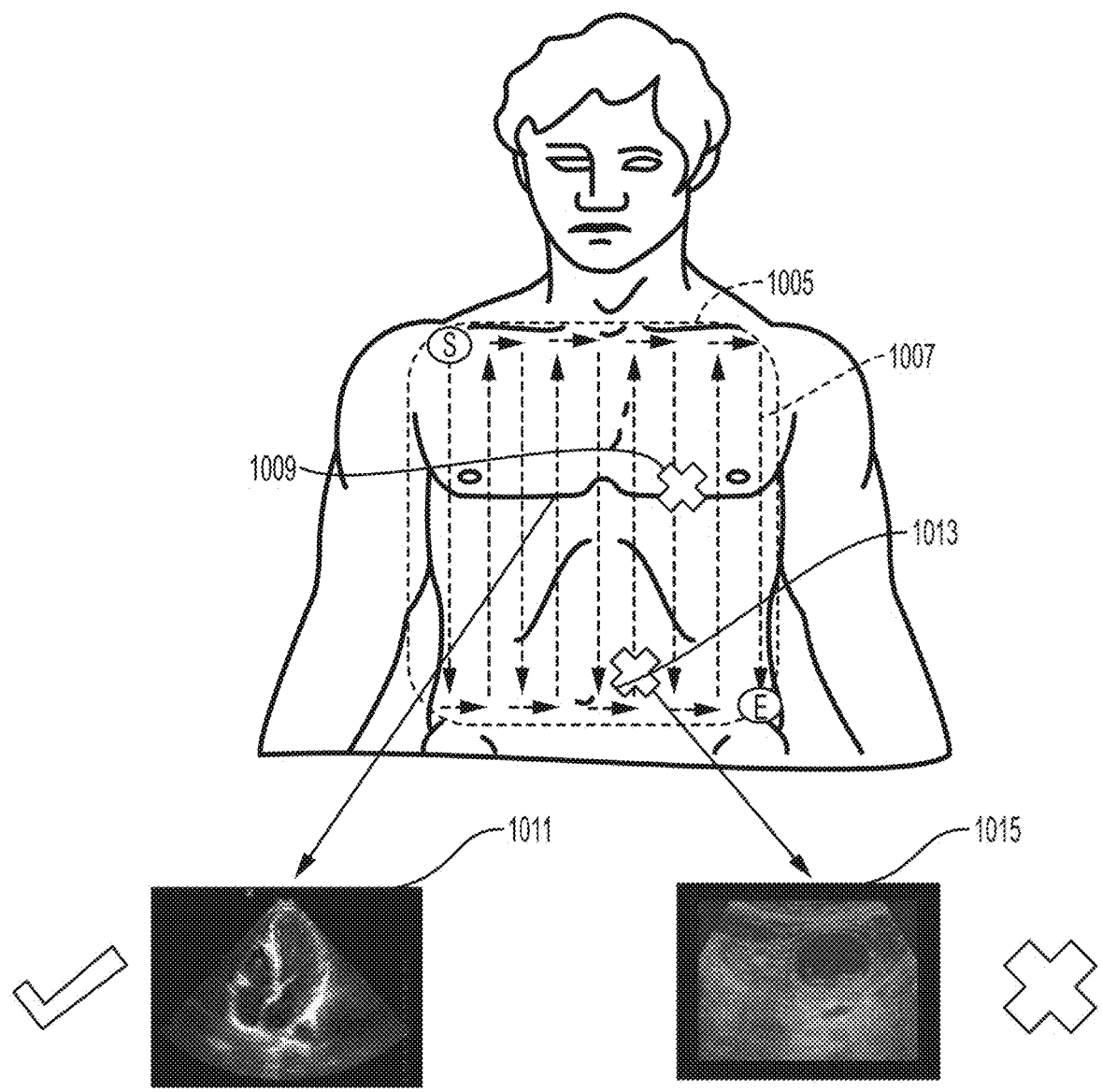
FIG. 10 shows an illustration of processing ultrasound images in accordance with certain embodiments disclosed herein.

FIG. 10 shows an illustration of processing ultrasound images in accordance with certain embodiments disclosed herein. As discussed above, in certain embodiments, a host device is configured to provide instructions to an operator to move an ultrasound device along a predetermined path relative to an anatomical area, whereby moving the ultrasound device along the predetermined path relative to the anatomical area results in collection of target ultrasound data and non-target ultrasound data. FIG. 10 shows an anatomical region 1005 and a predetermined path 1007 relative to the anatomical region 1005. FIG. 10 also shows a location 1009 along the predetermined path 1007 from which target ultrasound data capable of being transformed into an ultrasound image of a target anatomical view 1011 can be collected, and a location 1013 along the predetermined path 1007 from which non-target ultrasound data capable of being transformed into an ultrasound image 1015 of a non-target anatomical view can be collected. Accordingly, after the operator has moved move the ultrasound device along the predetermined path 1007 relative to the anatomical area 1005, thereby collecting target ultrasound data and non-target ultrasound data, it is desirable to process the collected ultrasound data to distinguish between the target ultrasound data, which should be saved, and the non-target ultrasound data, which can be discarded. In some embodiments, the non-target ultrasound data may also be saved.

In some embodiments, the host device that provides the instructions to the operator may receive the collected target and non-target ultrasound data, but not perform any processing of the data to distinguish between the target ultrasound data and the non-target ultrasound data. Instead, the host device may transmit the collected target and non-target ultrasound data to a server which is configured to distinguish between the target ultrasound data and the non-target ultrasound data. Upon identifying the target ultrasound data and the non-target ultrasound data, the server may be configured to save the target ultrasound data to memory (which may be at the server, at the host device, or at the ultrasound device) and discard the non-target ultrasound data. In some embodiments, the non-target ultrasound data may also be saved.

In some embodiments, the server may be configured to identify the target ultrasound data and non-target ultrasound data by analyzing acoustical data (e.g., digitally converted analog sound signals) collected by the ultrasound device. In some embodiments, the server may be configured to convert collected ultrasound data into a different form and identify the target ultrasound data and non-target ultrasound data by analyzing the converted ultrasound data. In some embodiments, the server may be configured to convert collected ultrasound data into ultrasound images and identify the target ultrasound data and non-target ultrasound data by analyzing the ultrasound images. In some embodiments, the server may be configured to transform the received ultrasound data into ultrasound images and analyze the ultrasound images to identify whether the images contain the target anatomical view or not. In some embodiments, the server may be configured to identify the target ultrasound data and non-target ultrasound data using deep learning, machine learning, and/or computer vision techniques. Deep learning techniques are discussed in more detail with reference to FIG. 19. The deep learning, machine learning, and computer vision techniques may be performed on collected ultrasound acoustical data, ultrasound images generated based on acoustical data, or any data generated based on collected ultrasound data. The deep learning, machine learning, and/or computer vision techniques may include use of a statistical model, which may be a convolutional neural network, a fully connected neural network, a recurrent neural network (e.g., a long short-term memory (LSTM) recurrent neural network), a random forest, a support vector machine, a linear classifier, and/or any other statistical model.

In some embodiments, the ultrasound device may be configured to transform ultrasound data into ultrasound images and transmit the ultrasound images to the host device. In such embodiments, the host device that provides the instructions to the operator may receive the ultrasound images, but not perform any processing of the images to distinguish between images containing the target anatomical view and images not containing the target anatomical view. Instead, the host device may transmit the ultrasound images and/or ultrasound data to a server which is configured to distinguish between images containing the target anatomical view and images not containing the target anatomical view. Upon identifying the images containing the target anatomical view and the images not containing the target anatomical view, the server may be configured to save the ultrasound data and/or ultrasound image(s) containing the target anatomical view to memory, and discard the ultrasound data and/or ultrasound image(s) not containing the target anatomical view. In some embodiments, the server may be configured to send the ultrasound data and/or ultrasound image(s) containing the target anatomical view to a medical professional (e.g., by email). In some embodiments, the ultrasound device may transmit the target and non-target ultrasound data and/or images produced from the ultrasound data directly to the server.

Identifying the target ultrasound data and the non-target ultrasound data may require storage of specific algorithms for analyzing the collected ultrasound data, sufficient processing speed to execute computations using these algorithms, and consumption of power while executing the computations. Because the host device can transmit the collected ultrasound data to a server without distinguishing between the target ultrasound data and the non-target ultrasound data, the host device may have lower requirements in terms of memory, processing speed, and power consumption. This may be beneficial when the host device is a personal smartphone, tablet, etc.

In some embodiments, the host device that provides the instructions to the operator may be configured to identify the target ultrasound data and non-target ultrasound data. In some embodiments, the host device may be configured to identify the target ultrasound data and non-target ultrasound data by analyzing acoustical data (e.g., digitally converted analog sound signals) collected by the ultrasound device. In some embodiments, the host device may be configured to convert collected ultrasound data into a different form and identify the target ultrasound data and non-target ultrasound data by analyzing the converted ultrasound data. In some embodiments, the host device may be configured to convert collected ultrasound data into ultrasound images and identify the target ultrasound data and non-target ultrasound data by analyzing the ultrasound images. In some embodiments, the host device may be configured to transform the received ultrasound data into ultrasound images and analyze the ultrasound images to identify whether the images contain the target anatomical view or not. In some embodiments, the server may be configured to identify the target ultrasound data and non-target ultrasound data using deep learning, machine learning, and/or computer vision techniques. Deep learning techniques are discussed in more detail with reference to FIG. 19. The deep learning, machine learning, and computer vision techniques may be performed on collected ultrasound acoustical data, ultrasound images generated based on acoustical data, or any data generated based on collected ultrasound data. Upon identifying the target ultrasound data and the non-target ultrasound data, the host device may be configured to save the target ultrasound data to memory (which may be at the server, at the host device, or at the ultrasound device) and discard the non-target ultrasound data. In some embodiments, the non-target ultrasound data may also be saved.

In some embodiments, the ultrasound device itself may be configured to identify the target ultrasound data and non-target ultrasound data. In some embodiments, the ultrasound device may be configured to identify the target ultrasound data and non-target ultrasound data by analyzing acoustical data (e.g., digitally converted analog sound signals) collected by the ultrasound device. In some embodiments, the ultrasound device may be configured to convert collected ultrasound data into a different form and identify the target ultrasound data and non-target ultrasound data by analyzing the converted ultrasound data. In some embodiments, the ultrasound device may be configured to convert collected ultrasound data into ultrasound images and identify the target ultrasound data and non-target ultrasound data by analyzing the ultrasound images. In some embodiments, the ultrasound device may be configured to transform the received ultrasound data into ultrasound images and analyze the ultrasound images to identify whether the images contain the target anatomical view or not. In some embodiments, the server may be configured to identify the target ultrasound data and non-target ultrasound data using deep learning, machine learning, and/or computer vision techniques. Deep learning techniques are discussed in more detail with reference to FIG. 19. The deep learning, machine learning, and computer vision techniques may be performed on collected ultrasound acoustical data, ultrasound images generated based on acoustical data, or any data generated based on collected ultrasound data. In some embodiments, a medical professional (e.g., a doctor, nurse, or imaging technician) or another individual, who may be remote, may receive the ultrasound data and determine which is the target ultrasound data and which is the non-target ultrasound data (e.g., by viewing ultrasound images generated from the ultrasound data).

Upon identifying the target ultrasound data and the non-target ultrasound data, the ultrasound device may be configured to save the target ultrasound data to memory (which may be at the server, at the host device, or at the ultrasound device) and discard the non-target ultrasound data. In some embodiments, the non-target ultrasound data may also be saved.

The above discussion related to FIG. 10, while discussed in the context of ultrasound data collected while moving an ultrasound device along a predetermined path, applies equally to ultrasound data collected while an operator moves an ultrasound device along a path at his or her own discretion.

Figure 11:
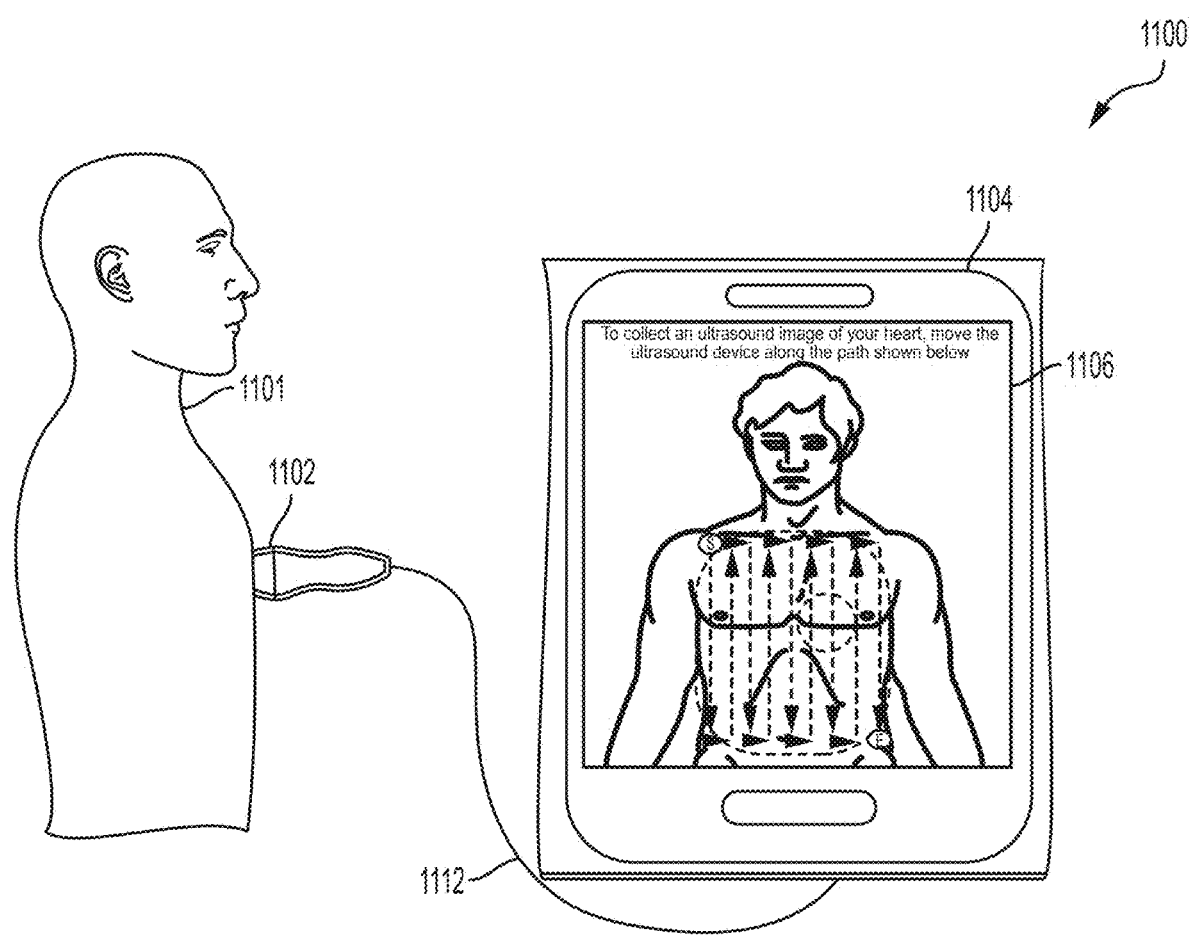
FIG. 11 shows an exemplary system for collecting ultrasound data from a subject in accordance with certain embodiments disclosed herein.

FIG. 11 shows an exemplary system 1100 for collecting ultrasound data from a subject 1101 in accordance with certain embodiments disclosed herein. The system 1100 includes an ultrasound device 1102 that is communicatively coupled to a host device 1104 by a communication link 1112. The host device 1104 includes a display 1106 and is configured to provide instructions 1114 to an operator to move the ultrasound device 1102 along a predetermined path relative to an anatomical area of the subject 1101 in order to collect both ultrasound data capable of being transformed into a target anatomical view and ultrasound data not capable of being transformed into the target anatomical view. The host device 1104 is also configured to receive ultrasound data from the ultrasound device 1102 over the communication link 1112.

The ultrasound device 1102 may be configured to generate ultrasound data. The ultrasound device 1102 may be configured to generate ultrasound data by, for example, emitting acoustic waves into the subject 1101 and detecting the reflected acoustic waves. The detected reflected acoustic wave may be analyzed to identify various properties of the tissues through which the acoustic wave traveled, such as a density of the tissue. The ultrasound device 1102 may be implemented in any of variety of ways. For example, the ultrasound device 1102 may be implemented as a handheld device or as a patch that is coupled to patient using, for example, an adhesive. Example ultrasound devices are described in detail with reference to FIGS. 14-18.

The communication link 1112 may be a wired (or wireless) communication link. In some embodiments, the communication link 1112 may be implemented as a cable such as a Universal Serial Bus (USB) cable or a Lightning cable. In these embodiments, the cable may also be used to transfer power from the host device 1104 to the ultrasound device 1102. In other embodiments, the communication link 1112 may be a wireless communication link such as a BLUETOOTH, WiFi, or ZIGBEE wireless communication link.

The host device 1104 may include one or more processing elements (such as a processor), for example, to provide instructions for moving the ultrasound device 1102 relative to the subject 1101. It should be appreciated that the host device 1104 may be implemented in any of a variety of ways. For example, the host device 1104 may be implemented as a mobile device (e.g., a mobile smartphone, a tablet, or a laptop). In other examples, the host device 1104 may be implemented as a stationary device such as a desktop computer. Additional example implementations of the host device are described with reference to FIGS. 12-13.

Figure 12:
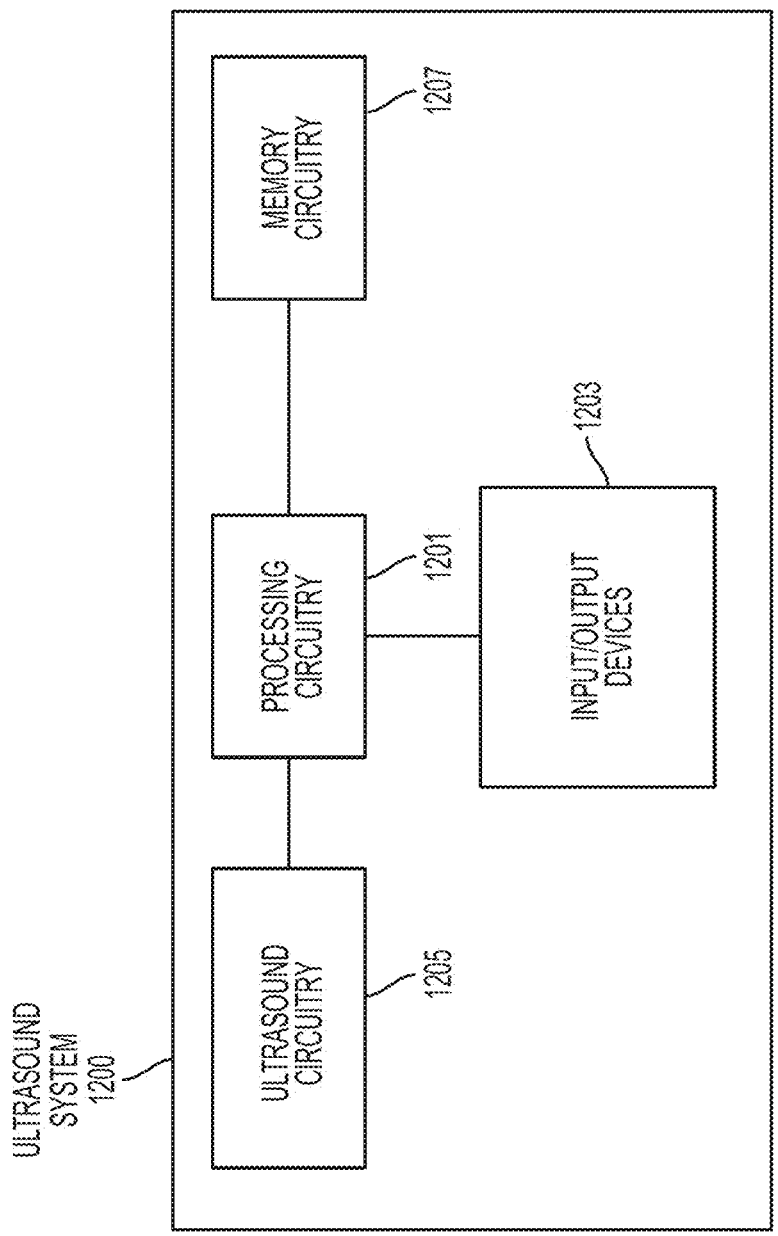
FIG. 12 shows a schematic block diagram illustrating aspects of an example ultrasound system upon which various aspects of the technology described herein may be practiced.

FIG. 12 shows a schematic block diagram illustrating aspects of an example ultrasound system 1200 upon which various aspects of the technology described herein may be practiced. For example, one or more components of the ultrasound system 1200 may perform any of the processes described herein. As shown, the ultrasound system 1200 includes processing circuitry 1201, input/output devices 1203, ultrasound circuitry 1205, and memory circuitry 1207.

The ultrasound circuitry 1205 may be configured to generate ultrasound data that may be employed to generate an ultrasound image. The ultrasound circuitry 1205 may include one or more ultrasonic transducers monolithically integrated onto a single semiconductor die. The ultrasonic transducers may include, for example, one or more capacitive micromachined ultrasonic transducers (CMUTs), one or more CMOS ultrasonic transducers (CUTs), one or more piezoelectric micromachined ultrasonic transducers (PMUTs), and/or one or more other suitable ultrasonic transducer cells. In some embodiments, the ultrasonic transducers may be formed on the same chip as other electronic components in the ultrasound circuitry 1205 (e.g., transmit circuitry, receive circuitry, control circuitry, power management circuitry, and processing circuitry) to form a monolithic ultrasound device.

The processing circuitry 1201 may be configured to perform any of the functionality described herein. The processing circuitry 1201 may include one or more processors (e.g., computer hardware processors). To perform one or more functions, the processing circuitry 1201 may execute one or more processor-executable instructions stored in the memory circuitry 1207. The memory circuitry 1207 may be used for storing programs and data during operation of the ultrasound system 1200. The memory circuitry 1207 may include one or more storage devices such as non-transitory computer-readable storage media. The processing circuitry 1201 may control writing data to and reading data from the memory circuity 1207 in any suitable manner.

In some embodiments, the processing circuitry 1201 may include specially-programmed and/or special-purpose hardware such as an application-specific integrated circuit (ASIC). For example, the processing circuitry 1201 may include one or more tensor processing units (TPUs). TPUs may be ASICs specifically designed for machine learning (e.g., deep learning). The TPUs may be employed to, for example, accelerate the inference phase of a neural network.

The input/output (I/O) devices 1203 may be configured to facilitate communication with other systems and/or an operator. Example I/O devices that may facilitate communication with an operator include: a keyboard, a mouse, a trackball, a microphone, a touch screen, a printing device, a display screen, a speaker, and a vibration device. Example I/O devices that may facilitate communication with other systems include wired and/or wireless communication circuitry such as BLUETOOTH, ZIGBEE, WiFi, and/or USB communication circuitry.

It should be appreciated that the ultrasound system 1200 may be implemented using any number of devices. For example, the components of the ultrasound system 1200 may be integrated into a single device. In another example, the ultrasound circuitry 1205 may be integrated into an ultrasound device that is communicatively coupled with a host device that includes the processing circuitry 1201, the input/output devices 1203, and the memory circuitry 1207.

Figure 13:
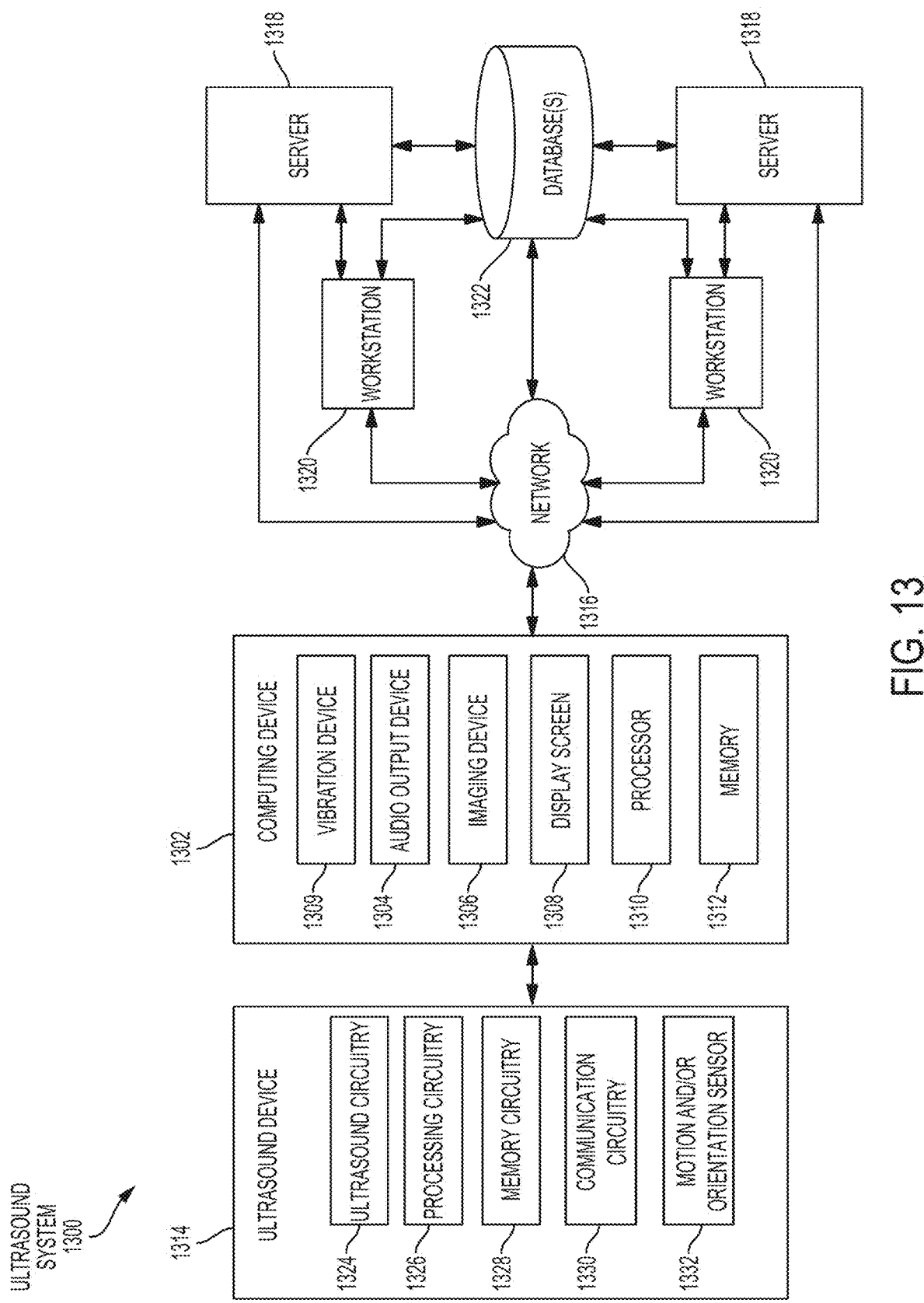
FIG. 13 shows a schematic block diagram illustrating aspects of another example ultrasound system upon which various aspects of the technology described herein may be practiced.

FIG. 13 shows a schematic block diagram illustrating aspects of another example ultrasound system 1300 upon which various aspects of the technology described herein may be practiced. For example, one or more components of the ultrasound system 1300 may perform any of the processes described herein. As shown, the ultrasound system 1300 includes an ultrasound device 1314 in wired and/or wireless communication with a host device 1302. The ultrasound device 1314 includes ultrasound circuitry 1324, processing circuitry 1326, memory circuitry 1328, communication circuitry 1330, and a motion and/or orientation sensor 1332. The host device 1302 includes an audio output device 1304, an imaging device 1306, a display screen 1308, a processor 1310, a memory 1312, and a vibration device 1309. The host device 1302 may communicate with one or more external devices over a network 1316. For example, the host device 1302 may communicate with one or more workstations 1320, servers 1318, and/or databases 1322.

The ultrasound device 1314 may be configured to generate ultrasound data that may be employed to generate an ultrasound image. The ultrasound device 1314 may be constructed in any of a variety of ways. In some embodiments, the ultrasound device 1314 includes a waveform generator that transmits a signal to a transmit beamformer which in turn drives transducer elements within a transducer array to emit pulsed ultrasonic signals into a structure, such as a patient. The pulsed ultrasonic signals may be backscattered from structures in the body, such as blood cells or muscular tissue, to produce echoes that return to the transducer elements. These echoes may then be converted into electrical signals, or ultrasound data, by the transducer elements and the electrical signals are received by a receiver. The electrical signals representing the received echoes are sent to a receive beamformer that outputs ultrasound data.

The ultrasound circuitry 1324 may be configured to generate the ultrasound data. The ultrasound circuitry 1324 may include one or more ultrasonic transducers monolithically integrated onto a single semiconductor die. The ultrasonic transducers may include, for example, one or more capacitive micromachined ultrasonic transducers (CMUTs), one or more CMOS (complementary metal-oxide-semiconductor) ultrasonic transducers (CUTs), one or more piezoelectric micromachined ultrasonic transducers (PMUTs), and/or one or more other suitable ultrasonic transducer cells. In some embodiments, the ultrasonic transducers may be formed the same chip as other electronic components in the ultrasound circuitry 1324 (e.g., transmit circuitry, receive circuitry, control circuitry, power management circuitry, and processing circuitry) to form a monolithic ultrasound device.

The processing circuitry 1326 may control operation of the ultrasound device 1314, and in particular, operation of the ultrasound circuitry 1324, the memory circuitry 1328, and the communication circuitry 1330. As one example, the processing circuitry 1326 may control collection of ultrasound data by the ultrasound device 1314. The memory circuitry 1328 may include non-transitory computer-readable storage media. The processing circuitry 1326 may control writing data to and reading data from the memory circuitry 1328 in any suitable manner. To perform any of the functionality of the ultrasound device 1314 described herein, the processing circuitry 1326 may execute one or more processor-executable instructions stored in one or more non-transitory computer-readable storage media (e.g., the memory circuitry 1328), which may serve as non-transitory computer-readable storage media storing processor-executable instructions for execution by the processing circuitry 1326. The communication circuitry 1330 may be configured to enable communication between the ultrasound device 1314 and the computing device 1302. The communication circuitry 1330 may include an antenna and circuitry capable of transmitting and receiving signals according to a certain wireless communication protocol (e.g., WiFi, BLUETOOTH, or Zigbee) and/or a data connector port for accepting a data connector of a particular type and circuitry capable of transmitting and receiving signals according to a certain protocol.

The motion and/or orientation sensor 1332 may be configured to generate motion and/or orientation data regarding the ultrasound device 1314. For example, the motion and/or orientation sensor 1332 may be configured to generate to generate data regarding acceleration of the ultrasound device 1314, data regarding angular velocity of the ultrasound device 1314, and/or data regarding magnetic force acting on the ultrasound device 1314 (which, due to the magnetic field of the earth, may be indicative of orientation relative to the earth). The motion and/or orientation sensor 1332 may include an accelerometer, a gyroscope, and/or a magnetometer. Depending on the sensors present in the motion and/or orientation sensor 1332, the motion and/or orientation data generated by the motion and/or orientation sensor 1332 may describe three degrees of freedom, six degrees of freedom, or nine degrees of freedom for the ultrasound device 1314. For example, the motion and/or orientation sensor may include an accelerometer, a gyroscope, and/or magnetometer. Each of these types of sensors may describe three degrees of freedom. If the motion and/or orientation sensor includes one of these sensors, the motion and/or orientation sensor may describe three degrees of freedom. If the motion and/or orientation sensor includes two of these sensors, the motion and/or orientation sensor may describe two degrees of freedom. If the motion and/or orientation sensor includes three of these sensors, the motion and/or orientation sensor may describe nine degrees of freedom.

The ultrasound device 1314 may be configured as a wearable ultrasound device, such as a patch. For further discussion of ultrasound devices and systems, such as more detail of components that may be included in the ultrasound device 1314, see U.S. patent application Ser. No. 15/415,434 titled "UNIVERSAL ULTRASOUND DEVICE AND RELATED APPARATUS AND METHODS," filed on Jan. 25, 2017 (and assigned to the assignee of the instant application).

The host device 1302 may be configured to process the ultrasound data from the ultrasound device 1314 to generate ultrasound images for display on the display screen 1308. The processing may be performed by, for example, the processor 1310. The processor 1310 may also be adapted to control the acquisition of ultrasound data with the ultrasound device 1314. The ultrasound data may be processed in real-time during a scanning session as the echo signals are received. In some embodiments, the displayed ultrasound image may be updated a rate of at least 5 Hz, at least 10 Hz, at least 20 Hz, at a rate between 5 and 60 Hz, at a rate of more than 60 Hz, or any suitable rate. For example, ultrasound data may be acquired even as images are being generated based on previously acquired data and while a live ultrasound image is being displayed. As additional ultrasound data is acquired, additional frames or images generated from more-recently acquired ultrasound data are sequentially displayed. Additionally, or alternatively, the ultrasound data may be stored temporarily in a buffer during a scanning session and processed in less than real-time.

Additionally (or alternatively), the host device 1302 may be configured to perform any of the processes described herein (e.g., using the processor 1310) and/or display any of the user interfaces described herein (e.g., using the display screen 1308). For example, the host device 1302 may be configured to provide instructions to an operator of the ultrasound device 1314 for moving the ultrasound device 1314 in order to collect ultrasound data. As shown, the host device 1302 may include one or more elements that may be used during the performance of such processes. For example, the host device 1302 may include one or more processors 1310 (e.g., computer hardware processors) and one or more articles of manufacture that include non-transitory computer-readable storage media such as the memory 1312. The processor 1310 may control writing data to and reading data from the memory 1312 in any suitable manner. To perform any of the functionality described herein, the processor 1310 may execute one or more processor-executable instructions stored in one or more non-transitory computer-readable storage media (e.g., the memory 1312), which may serve as non-transitory computer-readable storage media storing processor-executable instructions for execution by the processor 1310.

In some embodiments, the host device 1302 may include one or more input and/or output devices such as the audio output device 1304, the imaging device 1306, the display screen 1308, and the vibration device 1309. The audio output device 1304 may be a device that is configured to emit audible sound such as a speaker. The imaging device 1306 may be configured to detect light (e.g., visible light) to form an image such as a camera. The display screen 1308 may be configured to display images and/or videos such as a liquid crystal display (LCD), a plasma display, and/or an organic light emitting diode (OLED) display. The vibration device 1309 may be configured to vibrate one or more components of the host device 1302 to provide tactile feedback. These input and/or output devices may be communicatively coupled to the processor 1310 and/or under the control of the processor 1310. The processor 1310 may control these devices in accordance with a process being executed by the processor 1310 (such as any of the processes shown in FIGS. 20-21). For example, the processor 1310 may control the display screen 1308 to display any of the above described instructions. Similarly, the processor 1310 may control the audio output device 1304 to issue audible instructions. Additionally (or alternatively), the processor 1310 may control the imaging device 1306 to capture non-acoustic images of the ultrasound device 1314 being used on a subject to provide an operator of the ultrasound device 1314 an augmented reality interface (e.g., an augmented reality interface showing instructions for moving the ultrasound device 1314).

It should be appreciated that the host device 1302 may be implemented in any of a variety of ways. For example, the host device 1302 may be implemented as a handheld device such as a mobile smartphone or a tablet. Thereby, an operator of the ultrasound device 1314 may be able to operate the ultrasound device 1314 with one hand and hold the host device 1302 with another hand. In other examples, the host device 1302 may be implemented as a portable device that is not a handheld device such as a laptop. In yet other examples, the host device 1302 may be implemented as a stationary device such as a desktop computer.

In some embodiments, the host device 1302 may communicate with one or more external devices via the network 1316. The host device 1302 may be connected to the network 1316 over a wired connection (e.g., via an Ethernet cable) and/or a wireless connection (e.g., over a WiFi network). As shown in FIG. 13, these external devices may include servers 1318, workstations 1320, and/or databases 1322. The host device 1302 may communicate with these devices to, for example, off-load computationally intensive tasks. For example, the host device 1302 may send ultrasound data over the network 1316 to the server 1318 to be transformed into ultrasound image and analyzed (e.g., to identify whether the ultrasound images contain a target anatomical view). Additionally (or alternatively), the host device 1302 may communicate with these devices to access information that is not available locally and/or update a central information repository. For example, the host device 1302 may access the medical records of a subject being imaged with the ultrasound device 1314 from a file stored in the database 1322. In this example, the host device 1302 may also provide collected ultrasound data from the subject to the database 1322 to add to the medical record of the subject.

Figure 14:
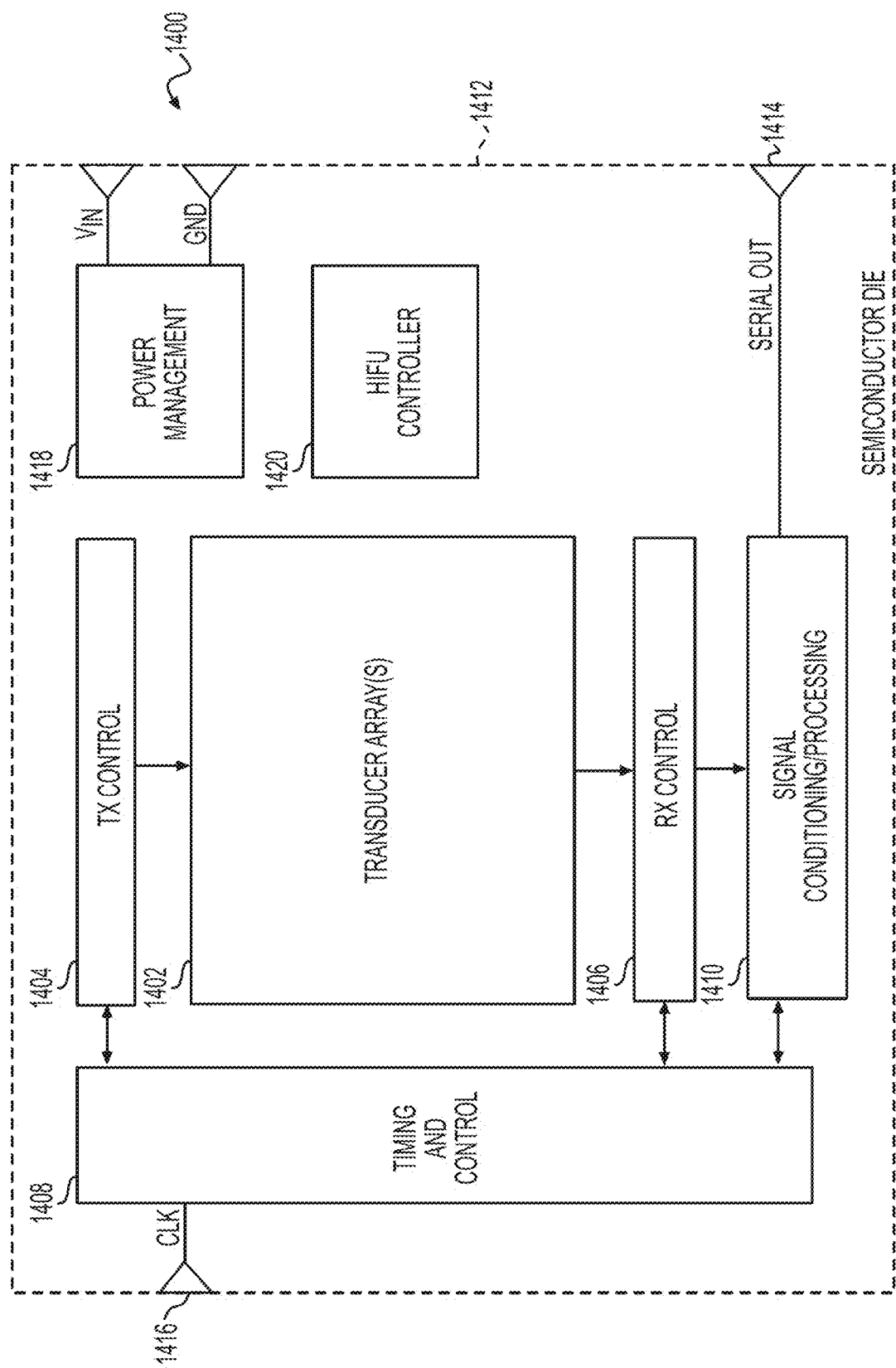
FIG. 14 shows an illustrative example of a monolithic ultrasound device that may be employed as any of the ultrasound devices described herein.

FIG. 14 shows an illustrative example of a monolithic ultrasound device 1400 that may be employed as any of the ultrasound devices described above, such as ultrasound devices 1102 and 1314 or any of the ultrasound circuitry described herein such as ultrasound circuitry 1205. As shown, the ultrasound device 1400 may include one or more transducer arrangements (e.g., arrays) 1402, transmit (TX) circuitry 1404, receive (RX) circuitry 1406, a timing and control circuit 1408, a signal conditioning/processing circuit 1410, a power management circuit 1418, and/or a high-intensity focused ultrasound (HIFU) controller 1420. In the embodiment shown, all of the illustrated elements are formed on a single semiconductor die 1412. It should be appreciated, however, that in alternative embodiments one or more of the illustrated elements may be instead located off-chip, or on multiple chips. In addition, although the illustrated example shows both TX circuitry 1404 and RX circuitry 1406, in alternative embodiments only TX circuitry or only RX circuitry may be employed. For example, such embodiments may be employed in a circumstance where one or more transmission-only devices 1400 are used to transmit acoustic signals and one or more reception-only devices 1400 are used to receive acoustic signals that have been transmitted through or reflected off of a subject being ultrasonically imaged.

It should be appreciated that communication between one or more of the illustrated components may be performed in any of numerous ways. In some embodiments, for example, one or more high-speed busses (not shown), such as that employed by a unified Northbridge, may be used to allow high-speed intra-chip communication or communication with one or more off-chip components.

The one or more transducer arrays 1402 may take on any of numerous forms, and aspects of the present technology do not necessarily require the use of any particular type or arrangement of transducer cells or transducer elements. Indeed, although the term "array" is used in this description, it should be appreciated that in some embodiments the transducer elements may not be organized in an array and may instead be arranged in some non-array fashion. In various embodiments, each of the transducer elements in the array 1402 may, for example, include one or more capacitive micromachined ultrasonic transducers (CMUTs), one or more CMOS ultrasonic transducers (CUTs), one or more piezoelectric micromachined ultrasonic transducers (PMUTs), and/or one or more other suitable ultrasonic transducer cells. In some embodiments, the transducer elements of the transducer array 1402 may be formed on the same chip as the electronics of the TX circuitry 1404 and/or RX circuitry 1406. The transducer elements 1402, TX circuitry 1404, and RX circuitry 1406 may, in some embodiments, be integrated in a single ultrasound device. In some embodiments, the single ultrasound device may be a handheld device. In other embodiments, the single ultrasound device may be embodied in a patch that may be coupled to a patient. The patch may be configured to transmit, wirelessly, data collected by the patch to one or more external devices for further processing.

A CUT may, for example, include a cavity formed in a CMOS wafer, with a membrane overlying the cavity, and in some embodiments sealing the cavity. Electrodes may be provided to create a transducer cell from the covered cavity structure. The CMOS wafer may include integrated circuitry to which the transducer cell may be connected. The transducer cell and CMOS wafer may be monolithically integrated, thus forming an integrated ultrasonic transducer cell and integrated circuit on a single substrate (the CMOS wafer).

The TX circuitry 1404 (if included) may, for example, generate pulses that drive the individual elements of, or one or more groups of elements within, the transducer array(s) 1402 so as to generate acoustic signals to be used for imaging. The RX circuitry 1406, on the other hand, may receive and process electronic signals generated by the individual elements of the transducer array(s) 1402 when acoustic signals impinge upon such elements.

In some embodiments, the timing and control circuit 1408 may, for example, be responsible for generating all timing and control signals that are used to synchronize and coordinate the operation of the other elements in the device 1400. In the example shown, the timing and control circuit 1408 is driven by a single clock signal CLK supplied to an input port 1416. The clock signal CLK may, for example, be a high-frequency clock used to drive one or more of the on-chip circuit components. In some embodiments, the clock signal CLK may, for example, be a 1.5625 GHz or 2.5 GHz clock used to drive a high-speed serial output device (not shown in FIG. 14) in the signal conditioning/processing circuit 1410, or a 20 MHz or 40 MHz clock used to drive other digital components on the semiconductor die 1412, and the timing and control circuit 1408 may divide or multiply the clock CLK, as necessary, to drive other components on the die 1412. In other embodiments, two or more clocks of different frequencies (such as those referenced above) may be separately supplied to the timing and control circuit 1408 from an off-chip source.

The power management circuit 1418 may, for example, be responsible for converting one or more input voltages VIN from an off-chip source into voltages needed to carry out operation of the chip, and for otherwise managing power consumption within the device 1400. In some embodiments, for example, a single voltage (e.g., 12V, 80V, 100V, 120V, etc.) may be supplied to the chip and the power management circuit 1418 may step that voltage up or down, as necessary, using a charge pump circuit or via some other DC-to-DC voltage conversion mechanism. In other embodiments, multiple different voltages may be supplied separately to the power management circuit 1418 for processing and/or distribution to the other on-chip components.

As shown in FIG. 14, in some embodiments, a HIFU controller 1420 may be integrated on the semiconductor die 1412 so as to enable the generation of HIFU signals via one or more elements of the transducer array(s) 1402. In other embodiments, a HIFU controller for driving the transducer array(s) 1402 may be located off-chip, or even within a device separate from the device 1400. That is, aspects of the present disclosure relate to provision of ultrasound-on-a-chip HIFU systems, with and without ultrasound imaging capability. It should be appreciated, however, that some embodiments may not have any HIFU capabilities and thus may not include a HIFU controller 1420.

Moreover, it should be appreciated that the HIFU controller 1420 may not represent distinct circuitry in those embodiments providing HIFU functionality. For example, in some embodiments, the remaining circuitry of FIG. 14 (other than the HIFU controller 1420) may be suitable to provide ultrasound imaging functionality and/or HIFU, i.e., in some embodiments the same shared circuitry may be operated as an imaging system and/or for HIFU. Whether or not imaging or HIFU functionality is exhibited may depend on the power provided to the system. HIFU typically operates at higher powers than ultrasound imaging. Thus, providing the system a first power level (or voltage level) appropriate for imaging applications may cause the system to operate as an imaging system, whereas providing a higher power level (or voltage level) may cause the system to operate for HIFU. Such power management may be provided by off-chip control circuitry in some embodiments.

In addition to using different power levels, imaging and HIFU applications may utilize different waveforms. Thus, waveform generation circuitry may be used to provide suitable waveforms for operating the system as either an imaging system or a HIFU system.

In some embodiments, the system may operate as both an imaging system and a HIFU system (e.g., capable of providing image-guided HIFU). In some such embodiments, the same on-chip circuitry may be utilized to provide both functions, with suitable timing sequences used to control the operation between the two modalities.

In the example shown, one or more output ports 1414 may output a high-speed serial data stream generated by one or more components of the signal conditioning/processing circuit 1410. Such data streams may, for example, be generated by one or more USB 3.0 modules, and/or one or more 10 GB, 40 GB, or 100 GB Ethernet modules, integrated on the semiconductor die 1412. In some embodiments, the signal stream produced on output port 1614 can be fed to a computer, tablet, or smartphone for the generation and/or display of 2-dimensional, 3-dimensional, and/or tomographic images. In embodiments in which image formation capabilities are incorporated in the signal conditioning/processing circuit 1410, even relatively low-power devices, such as smartphones or tablets which have only a limited amount of processing power and memory available for application execution, can display images using only a serial data stream from the output port 1414. As noted above, the use of on-chip analog-to-digital conversion and a high-speed serial data link to offload a digital data stream is one of the features that helps facilitate an "ultrasound on a chip" solution according to some embodiments of the technology described herein.

Devices 1400 such as that shown in FIG. 14 may be used in any of a number of imaging and/or treatment (e.g., HIFU) applications, and the particular examples discussed herein should not be viewed as limiting. In one illustrative implementation, for example, an imaging device including an N×M planar or substantially planar array of CMUT elements may itself be used to acquire an ultrasonic image of a subject, e.g., a person's abdomen, by energizing some or all of the elements in the array(s) 1402 (either together or individually) during one or more transmit phases, and receiving and processing signals generated by some or all of the elements in the array(s) 1402 during one or more receive phases, such that during each receive phase the CMUT elements sense acoustic signals reflected by the subject. In other implementations, some of the elements in the array(s) 1402 may be used only to transmit acoustic signals and other elements in the same array(s) 1402 may be simultaneously used only to receive acoustic signals. Moreover, in some implementations, a single imaging device may include a P×Q array of individual devices, or a P×Q array of individual N×M planar arrays of CMUT elements, which components can be operated in parallel, sequentially, or according to some other timing scheme so as to allow data to be accumulated from a larger number of CMUT elements than can be embodied in a single device 1400 or on a single die 1412.

In yet other implementations, a pair of imaging devices can be positioned so as to straddle a subject, such that one or more CMUT elements in the device(s) 1400 of the imaging device on one side of the subject can sense acoustic signals generated by one or more CMUT elements in the device(s) 1400 of the imaging device on the other side of the subject, to the extent that such pulses were not substantially attenuated by the subject. Moreover, in some implementations, the same device 1400 can be used to measure both the scattering of acoustic signals from one or more of its own CMUT elements as well as the transmission of acoustic signals from one or more of the CMUT elements disposed in an imaging device on the opposite side of the subject.

Figure 15:
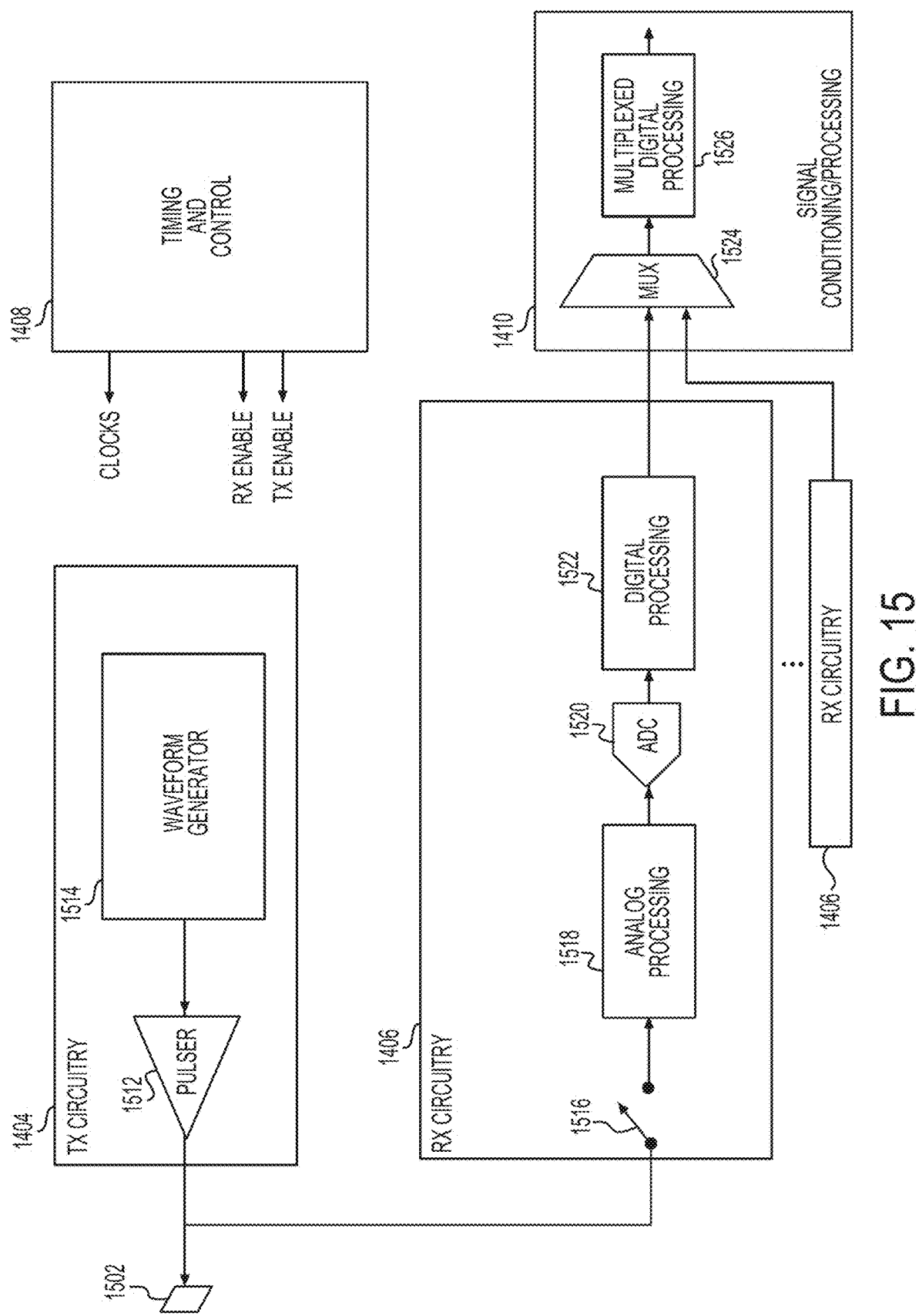
FIG. 15 shows a block diagram illustrating transmit circuitry and receive circuitry in accordance with certain embodiments disclosed herein.

FIG. 15 shows a block diagram illustrating transmit (TX) circuitry 1404 and receive (RX) circuitry 1406 in accordance with certain embodiments disclosed herein. In particular, FIG. 15 shows a block diagram illustrating how, in some embodiments, the TX circuitry 1404 and the RX circuitry 1406 for a given transducer element 1502 may be used either to energize the transducer element 1502 to emit an ultrasonic pulse, or to receive and process a signal from the transducer element 1502 representing an ultrasonic pulse sensed by it, in accordance with certain embodiments disclosed herein. In some implementations, the TX circuitry 1404 may be used during a "transmission" phase, and the RX circuitry may be used during a "reception" phase that is non-overlapping with the transmission phase. In other implementations, one of the TX circuitry 1404 and the RX circuitry 1406 may simply not be used in a given device (e.g., ultrasound device 1400), such as when a pair of ultrasound units is used for only transmissive imaging. As noted above, in some embodiments, an ultrasound device may alternatively employ only TX circuitry 1404 or only RX circuitry 1406, and aspects of the present technology do not necessarily require the presence of both such types of circuitry. In various embodiments, TX circuitry 1404 and/or RX circuitry 1406 may include a TX circuit and/or an RX circuit associated with a single transducer cell (e.g., a CUT or CMUT), a group of two or more transducer cells within a single transducer element 1502, a single transducer element 1502 comprising a group of transducer cells, a group of two or more transducer elements 1502 within an array 1502, or an entire array 1502 of transducer elements 1502.

In the example shown in FIG. 15, the TX circuitry 1404/RX circuitry 1406 includes a separate TX circuit and a separate RX circuit for each transducer element 1502 in the array(s) 1502, but there is only one instance of each of the timing & control circuit 1408 and the signal conditioning/processing circuit 1410. Accordingly, in such an implementation, the timing & control circuit 1408 may be responsible for synchronizing and coordinating the operation of all of the TX circuitry 1404/RX circuitry 1406 combinations on the die (e.g., semiconductor die 1412), and the signal conditioning/processing circuit 1410 may be responsible for handling inputs from all of the RX circuitry 1406 on the die. In other embodiments, the timing and control circuit 1408 may be replicated for each transducer element 1502 or for a group of transducer elements 1502.

As shown in FIG. 15, in addition to generating and/or distributing clock signals to drive the various digital components in the device, the timing & control circuit 1408 may output either an "TX enable" signal to enable the operation of each TX circuit of the TX circuitry 1404, or an "RX enable" signal to enable operation of each RX circuit of the RX circuitry 1406. In the example shown, a switch 1516 in the RX circuitry 1406 may always be opened before the TX circuitry 1404 is enabled, so as to prevent an output of the TX circuitry 1404 from driving the RX circuitry 1406. The switch 1516 may be closed when operation of the RX circuitry 1406 is enabled, so as to allow the RX circuitry 1406 to receive and process a signal generated by the transducer element 1502.

As shown, the TX circuitry 1404 for a respective transducer element 1502 may include both a waveform generator 1514 and a pulser 1512. The waveform generator 1514 may, for example, be responsible for generating a waveform that is to be applied to the pulser 1512, so as to cause the pulser 1512 to output a driving signal to the transducer element 1502 corresponding to the generated waveform.

In the example shown in FIG. 15, the RX circuitry 1406 for a respective transducer element 1502 includes an analog processing block 1518, an analog-to-digital converter (ADC) 1520, and a digital processing block 1522. The ADC 1520 may, for example, include a 10-bit or 12-bit, 20 Msps, 25 Msps, 40 Msps, 50 Msps, or 80 Msps ADC.

After undergoing processing in the digital processing block 1522, the outputs of all of the RX circuits on the semiconductor die (the number of which, in this example, is equal to the number of transducer elements 1502 on the chip) are fed to a multiplexer (MUX) 1524 in the signal conditioning/processing circuit 1410. In other embodiments, the number of transducer elements is larger than the number of RX circuits, and several transducer elements provide signals to a single RX circuit. The MUX 1524 multiplexes the digital data from the RX circuits, and the output of the MUX 1524 is fed to a multiplexed digital processing block 1526 in the signal conditioning/processing circuit 1410, for final processing before the data is output from the semiconductor die, e.g., via one or more high-speed serial output ports 1514. The MUX 1524 is optional, and in some embodiments parallel signal processing is performed. A high-speed serial data port may be provided at any interface between or within blocks, any interface between chips and/or any interface to a host. Various components in the analog processing block 1518 and/or the digital processing block 1522 may reduce the amount of data that needs to be output from the semiconductor die via a high-speed serial data link or otherwise. In some embodiments, for example, one or more components in the analog processing block 1518 and/or the digital processing block 1522 may thus serve to allow the RX circuitry 1406 to receive transmitted and/or scattered ultrasound pressure waves with an improved signal-to-noise ratio (SNR) and in a manner compatible with a diversity of waveforms. The inclusion of such elements may thus further facilitate and/or enhance the disclosed "ultrasound-on-a-chip" solution in some embodiments.

The ultrasound devices described herein may be implemented in any of a variety of physical configurations including as part of a handheld device a (which may include a screen to display obtained images) or as part of a patch configured to be affixed to the subject.

Figure 16A:
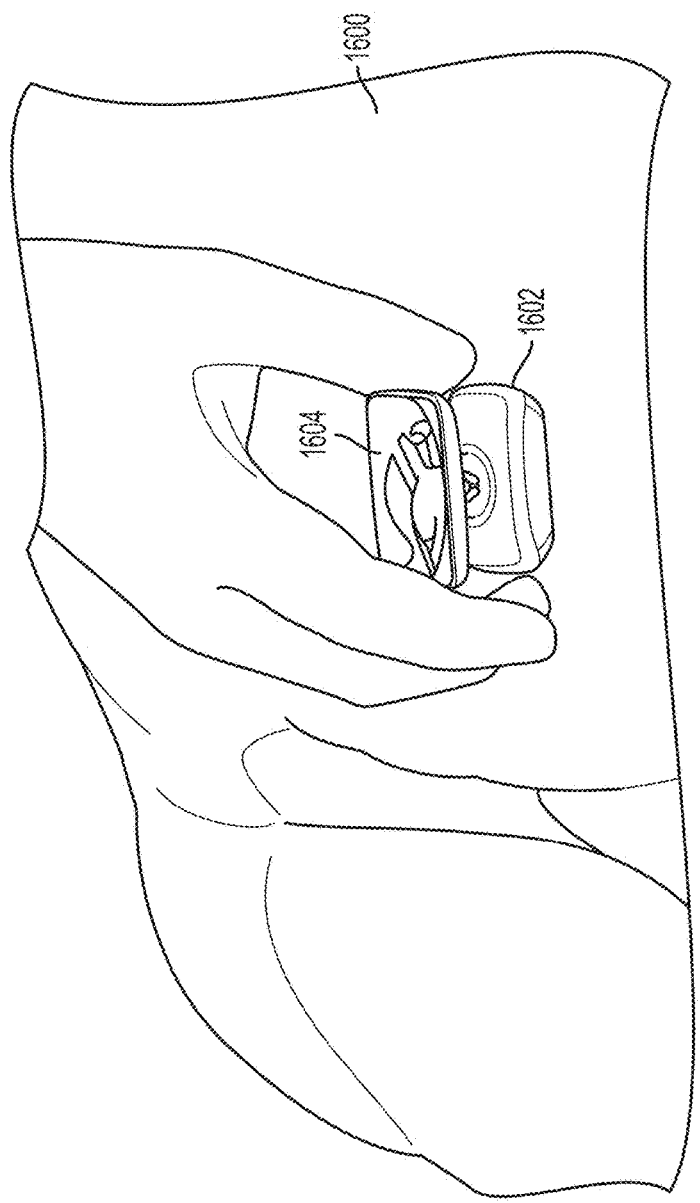
FIGS. 16A and 16B show how an ultrasound device may be embodied in a handheld device in accordance with certain embodiments disclosed herein.
Figure 16B:
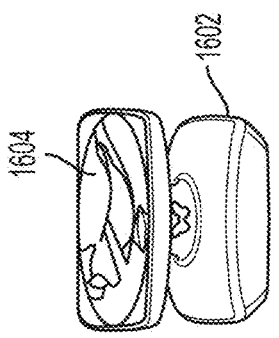

In some embodiments, an ultrasound device may be embodied in a handheld device. FIGS. 16A and 16B show how an ultrasound device may be embodied in a handheld device 1602 in accordance with certain embodiments disclosed herein. The handheld device 1602 may be held against (or near) a subject 1600 and used to image the subject. The handheld device 1602 may include an ultrasound device and a display 1604, which in some embodiments, may be a touchscreen. The display 1604 may be configured to display images of the subject (e.g., ultrasound images) generated within the handheld device 1602 using ultrasound data gathered by the ultrasound device within the device 1602.

In some embodiments, the handheld device 1602 may be used in a manner analogous to a stethoscope. A medical professional may place the handheld device 1602 at various positions along a patient's body. The ultrasound device within the handheld device 1602 may image the patient. The data obtained by the ultrasound device may be processed and used to generate image(s) of the patient, which image(s) may be displayed to the medical professional via the display 1604. As such, a medical professional could carry the handheld device 1602 (e.g., around their neck or in their pocket) rather than carrying around multiple conventional devices, which is burdensome and impractical.

Figure 17A:
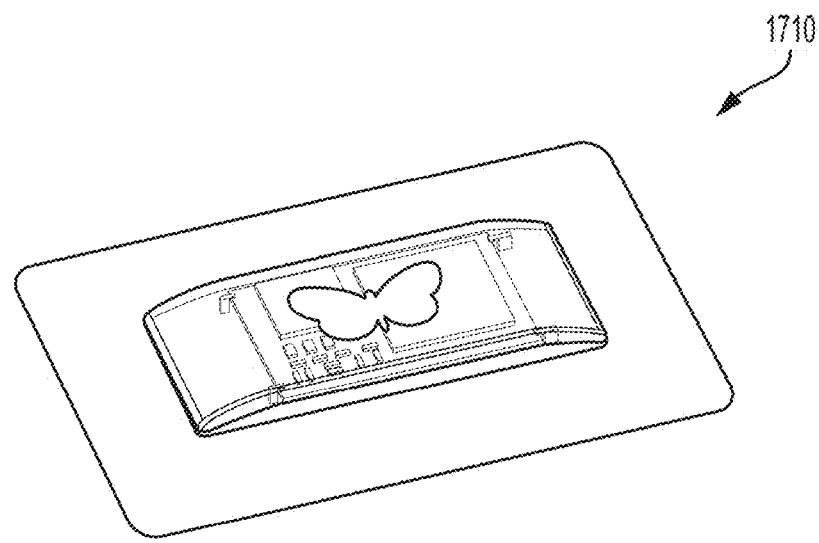
FIGS. 17A and 17B shows how an ultrasound device may be embodied in a patch that may be coupled to a patient in accordance with certain embodiments disclosed herein.
Figure 17B:
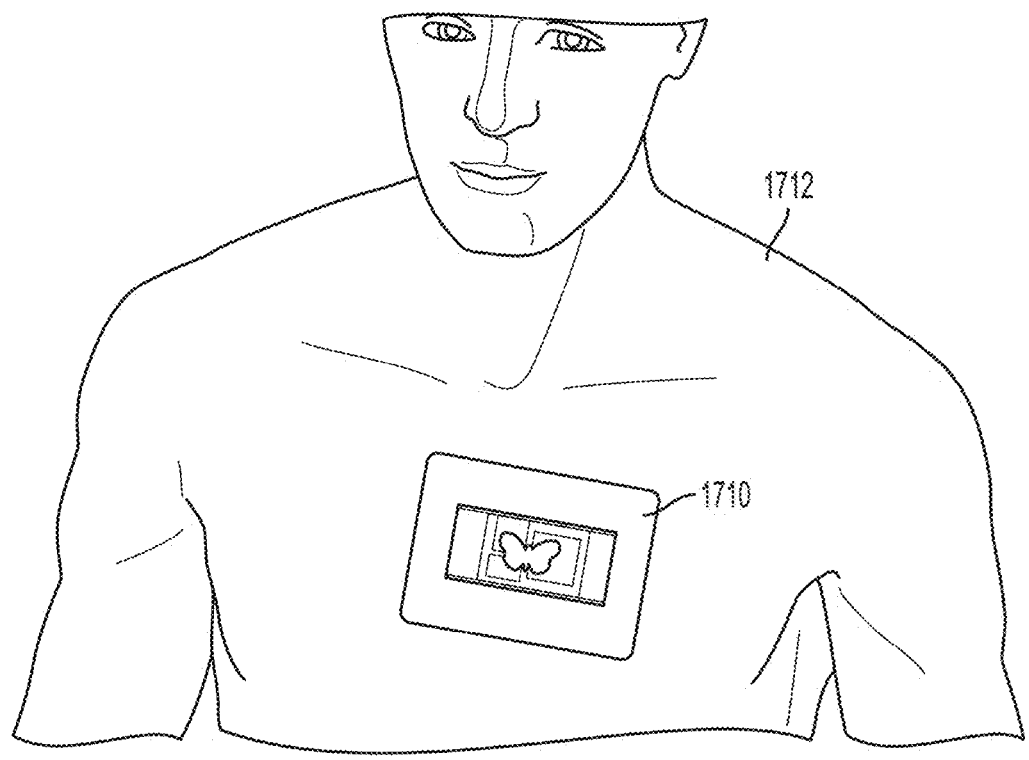
Figure 17C:
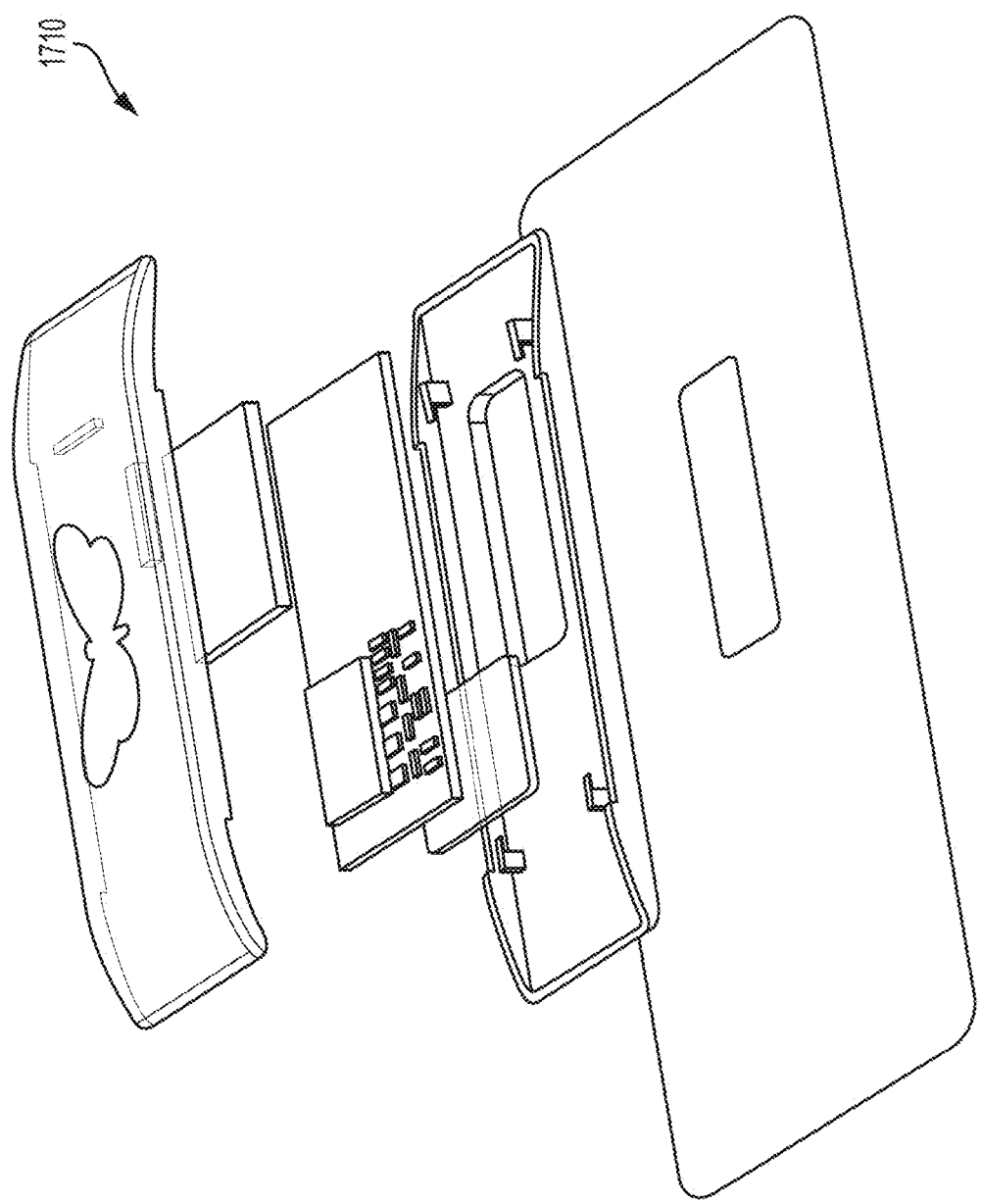
FIG. 17C shows an exploded view of the patch of FIGS. 17A and 17B.

In some embodiments, an ultrasound device may be embodied in a patch that may be coupled to a patient. FIGS. 17A and 17B shows how an ultrasound device may be embodied in a patch 1710 that may be coupled to a patient 1712 in accordance with certain embodiments disclosed herein. The patch 1710 may be configured to transmit, wirelessly, data collected by the patch 1710 to one or more external devices for further processing. FIG. 17C shows an exploded view of the patch 1710.

Figure 18:
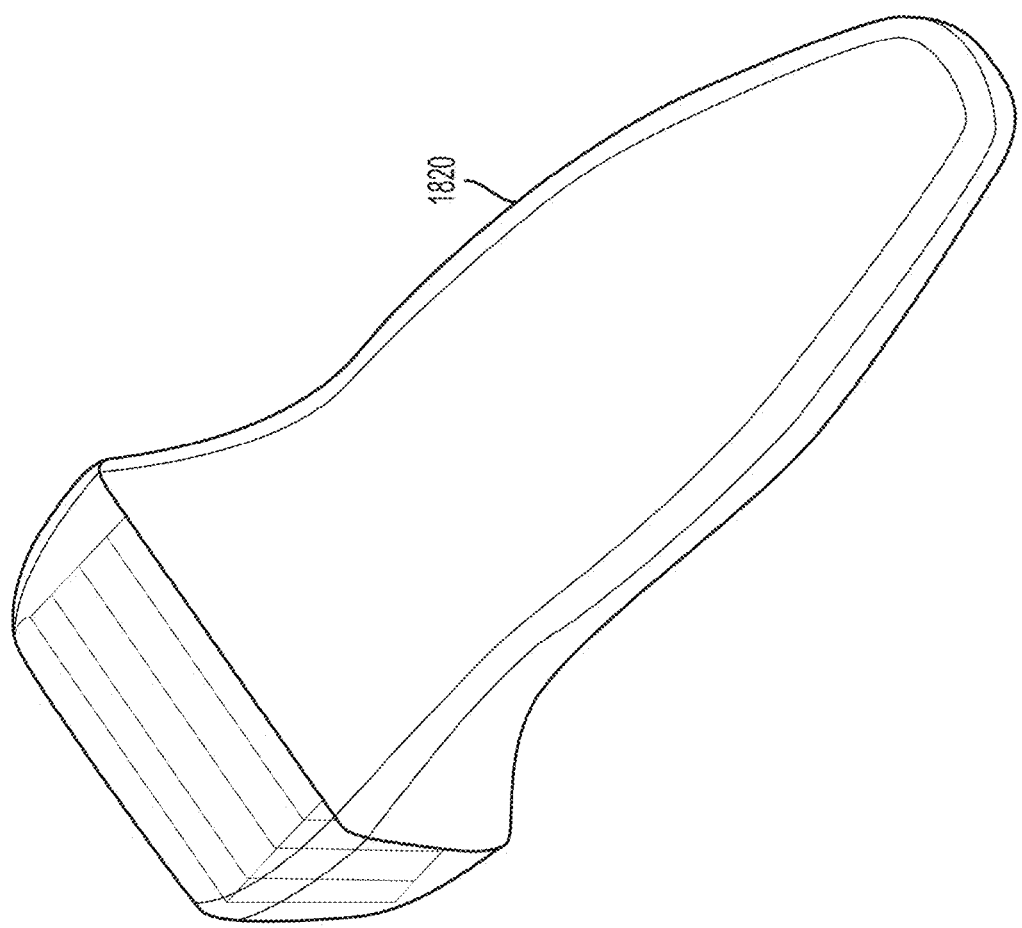
FIG. 18 shows how an ultrasound device may be embodied in a handheld device in accordance with certain embodiments disclosed herein.

FIG. 18 shows how an ultrasound device may be embodied in a handheld device 1820 in accordance with certain embodiments disclosed herein. The handheld device 1820 may be configured to transmit data collected by the device 1820 wirelessly to one or more external device for further processing. In other embodiments, the handheld device 1820 may be configured transmit data collected by the device 1820 to one or more external devices using one or more wired connections, as aspects of the technology described herein are not limited in this respect.

Aspects of the technology described herein relate to the application of automated image processing techniques to analyze images, such as ultrasound images. In some embodiments, an image may be analyzed to identify it as showing a target anatomical view or not. In some embodiments, the automated image processing techniques may include machine learning techniques such as deep learning techniques. Machine learning techniques may include techniques that seek to identify patterns in a set of data points and use the identified patterns to make predictions for new data points. These machine learning techniques may involve training (and/or building) a model using a training data set to make such predictions. The trained model may be used as, for example, a classifier that is configured to receive a data point as an input and provide an indication of a class to which the data point likely belongs as an output.

Deep learning techniques may include those machine learning techniques that employ neural networks to make predictions. Neural networks typically include a collection of neural units (referred to as neurons) that each may be configured to receive one or more inputs and provide an output that is a function of the input. For example, the neuron may sum the inputs and apply a transfer function (sometimes referred to as an "activation function") to the summed inputs to generate the output. The neuron may apply a weight to each input to, for example, weight some inputs higher than others. Example transfer functions that may be employed include step functions, piecewise linear functions, and sigmoid functions. These neurons may be organized into a plurality of sequential layers that each include one or more neurons. The plurality of sequential layers may include an input layer that receives the input data for the neural network, an output layer that provides the output data for the neural network, and one or more hidden layers connected between the input and output layers. Each neuron in a hidden layer may receive inputs from one or more neurons in a previous layer (such as the input layer) and provide an output to one or more neurons in a subsequent layer (such as an output layer).

A neural network may be trained using, for example, labeled training data. The labeled training data may include a set of example inputs and an answer associated with each input. For example, the training data may include a plurality of ultrasound images that are each labeled with an anatomical view that is contained in the respective ultrasound image. In this example, the ultrasound images may be provided to the neural network to obtain outputs that may be compared with the labels associated with each of the ultrasound images. One or more characteristics of the neural network (such as the interconnections between neurons (referred to as edges) in different layers and/or the weights associated with the edges) may be adjusted until the neural network correctly classifies most (or all) of the input images.

Once the training data has been created, the training data may be loaded to a database (e.g., an image database) and used to train a neural network using deep learning techniques. Once the neural network has been trained, the trained neural network may be deployed to one or more host devices. It should be appreciated that the neural network may be trained with any number of sample patient images. For example, a neural network may be trained with as few as 7 or so sample patient images, although it will be appreciated that the more sample images used, the more robust the trained model data may be.

Figure 19:
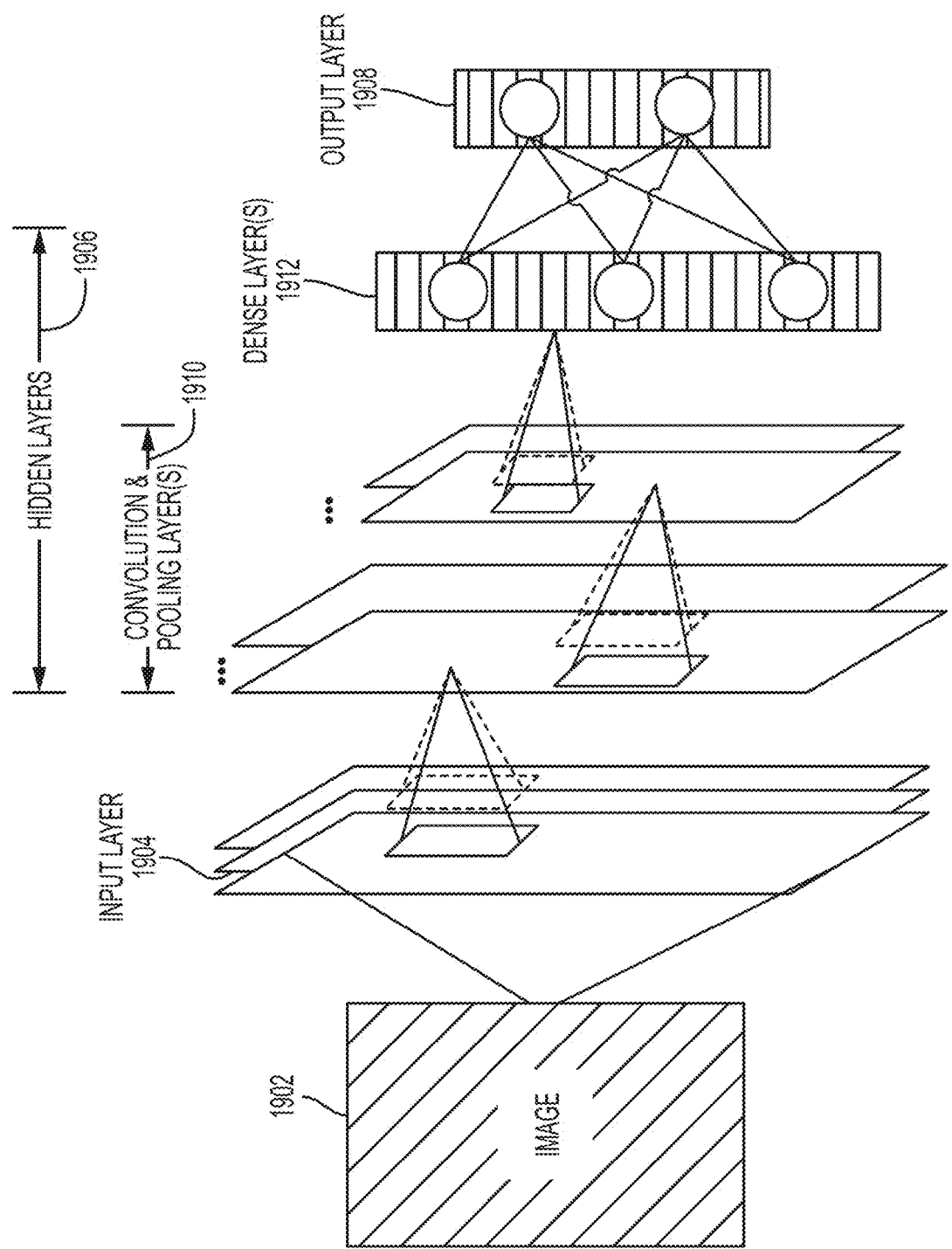
FIG. 19 shows an example convolutional neural network that is configured to analyze an image in accordance with certain embodiments disclosed herein.

In some applications, a neural network may be implemented using one or more convolution layers to form a convolutional neural network. FIG. 19 shows an example convolutional neural network that is configured to analyze an image 1902 in accordance with certain embodiments disclosed herein. As shown, the convolutional neural network includes an input layer 1904 to receive the image 1902, an output layer 1908 to provide the output, and a plurality of hidden layers 1906 connected between the input layer 1904 and the output layer 1908. The plurality of hidden layers 1906 includes convolution and pooling layers 1910 and dense layers 1912.

The input layer 1904 may receive the input to the convolutional neural network. As shown in FIG. 19, the input the convolutional neural network may be the image 1902. The image 1902 may be, for example, an ultrasound image.

The input layer 1904 may be followed by one or more convolution and pooling layers 1910. A convolutional layer may include a set of filters that are spatially smaller (e.g., have a smaller width and/or height) than the input to the convolutional layer (e.g., the image 1902). Each of the filters may be convolved with the input to the convolutional layer to produce an activation map (e.g., a 2-dimensional activation map) indicative of the responses of that filter at every spatial position. The convolutional layer may be followed by a pooling layer that down-samples the output of a convolutional layer to reduce its dimensions. The pooling layer may use any of a variety of pooling techniques such as max pooling and/or global average pooling. In some embodiments, the down-sampling may be performed by the convolution layer itself (e.g., without a pooling layer) using striding.

The convolution and pooling layers 1910 may be followed by dense layers 1912. The dense layers 1912 may include one or more layers each with one or more neurons that receives an input from a previous layer (e.g., a convolutional or pooling layer) and provides an output to a subsequent layer (e.g., the output layer 1908). The dense layers 1912 may be described as "dense" because each of the neurons in a given layer may receive an input from each neuron in a previous layer and provide an output to each neuron in a subsequent layer. The dense layers 1912 may be followed by an output layer 1908 that provides the output of the convolutional neural network. The output may be, for example, an indication of which class, from a set of classes, the image 1902 (or any portion of the image 1902) belongs to.

It should be appreciated that the convolutional neural network shown in FIG. 19 is only one example implementation and that other implementations may be employed. For example, one or more layers may be added to or removed from the convolutional neural network shown in FIG. 19. Additional example layers that may be added to the convolutional neural network include: a rectified linear units (ReLU) layer, a pad layer, a concatenate layer, and an upscale layer. An upscale layer may be configured to upsample the input to the layer. An ReLU layer may be configured to apply a rectifier (sometimes referred to as a ramp function) as a transfer function to the input. A pad layer may be configured to change the size of the input to the layer by padding one or more dimensions of the input. A concatenate layer may be configured to combine multiple inputs (e.g., combine inputs from multiple layers) into a single output.

Convolutional neural networks may be employed to perform any of a variety of functions described herein. For example, a convolutional neural network may be employed to identify an anatomical view contained in an ultrasound image. It should be appreciated that more than a single convolutional neural network may be employed to perform a function.

An example implementation of a convolutional network is shown below in Table 1. The convolutional neural network shown in Table 1 may be employed to classify an input image (e.g., an ultrasound image). For example, the convolutional network shown in Table 1 may be configured to receive an input ultrasound image and provide an output that is indicative of the anatomical view contained in the image. In Table 1, the sequence of the layer is denoted by the "Layer Number" column, the type of the layer is denoted by the "Layer Type" column, and the input to the layer is denoted by the "Input to Layer" column.

TABLE 1

Example Layer Configuration for Convolutional neural network

| Layer Number | Layer Type | Input to Layer |
|---|---|---|
| 1 | Input Layer | Input Image |
| 2 | Convolution Layer | Output of Layer 1 |
| 3 | Convolution Layer | Output of Layer 2 |

TABLE 1-continued

Example Layer Configuration for Convolutional neural network

| Layer Number | Layer Type | Input to Layer |
|---|---|---|
| 4 | Pooling Layer | Output of Layer 3 |
| 5 | Convolution Layer | Output of Layer 4 |
| 6 | Convolution Layer | Output of Layer 5 |
| 7 | Pooling Layer | Output of Layer 6 |
| 8 | Convolution Layer | Output of Layer 7 |
| 9 | Convolution Layer | Output of Layer 8 |
| 10 | Pooling Layer | Output of Layer 9 |
| 11 | Convolution Layer | Output of Layer 10 |
| 12 | Convolution Layer | Output of Layer 11 |
| 13 | Pooling Layer | Output of Layer 12 |
| 14 | Fully Connected Layer | Output of Layer 13 |
| 15 | Fully Connected Layer | Output of Layer 14 |
| 16 | Fully Connected Layer | Output of Layer 15 |

Another example implementation of a convolutional neural network is shown below in Table 2. The convolutional neural network in Table 2 may be employed to identify two points on the basal segments of the left ventricle in an ultrasound image. In Table 2, the sequence of the layer is denoted by the "Layer Number" column, the type of the layer is denoted by the "Layer Type" column, and the input to the layer is denoted by the "Input to Layer" column.

TABLE 2

Example Layer Configuration for Convolutional neural network

| Layer Number | Layer Type | Input to Layer |
|---|---|---|
| 1 | Input Layer | Input Image |
| 2 | Convolution Layer | Output of Layer 1 |
| 3 | Convolution Layer | Output of Layer 2 |
| 4 | Pooling Layer | Output of Layer 3 |
| 5 | Convolution Layer | Output of Layer 4 |
| 6 | Convolution Layer | Output of Layer 5 |
| 7 | Pooling Layer | Output of Layer 6 |
| 8 | Convolution Layer | Output of Layer 7 |
| 9 | Convolution Layer | Output of Layer 8 |
| 10 | Pooling Layer | Output of Layer 9 |
| 11 | Convolution Layer | Output of Layer 10 |
| 12 | Convolution Layer | Output of Layer 11 |
| 13 | Convolution Layer | Output of Layer 12 |
| 14 | Fully Connected Layer | Output of Layer 13 |
| 15 | Fully Connected Layer | Output of Layer 14 |
| 16 | Fully Connected Layer | Output of Layer 15 |

Yet another example implementation of convolutional neural network is shown below in Table 3. The convolutional neural network shown in Table 3 may be configured to receive an ultrasound image and classify each pixel in the input image as belonging to the foreground (anatomical structure, e.g., left ventricle) or to the background. Relative to the convolutional neural networks shown in Tables 1 and 2, upsampling layers have been introduced to increase the resolution of the classification output. The output of the upsampled layers is combined with the output of other layers to provide accurate classification of individual pixels. In Table 3, the sequence of the layer is denoted by the "Layer Number" column, the type of the layer is denoted by the "Layer Type" column, and the input to the layer is denoted by the "Input to Layer" column.

TABLE 3

Example Layer Configuration for Convolutional neural network

| Layer Number | Layer Type | Input to Layer |
|---|---|---|
| 1 | Input Layer | Input Image |
| 2 | Convolution Layer | Output of Layer 1 |
| 3 | Convolution Layer | Output of Layer 2 |
| 4 | Pooling Layer | Output of Layer 3 |
| 5 | Convolution Layer | Output of Layer 4 |
| 6 | Convolution Layer | Output of Layer 5 |
| 7 | Pooling Layer | Output of Layer 6 |
| 8 | Convolution Layer | Output of Layer 7 |
| 9 | Convolution Layer | Output of Layer 8 |
| 10 | Pooling Layer | Output of Layer 9 |
| 11 | Convolution Layer | Output of Layer 10 |
| 12 | Convolution Layer | Output of Layer 11 |
| 13 | Convolution Layer | Output of Layer 12 |
| 14 | Upscale Layer | Output of Layer 13 |
| 15 | Convolution Layer | Output of Layer 14 |
| 16 | Pad Layer | Output of Layer 15 |
| 17 | Concatenate Layer | Output of Layers 9 and 16 |
| 18 | Convolution Layer | Output of Layer 17 |
| 19 | Convolution Layer | Output of Layer 18 |
| 20 | Upscale Layer | Output of Layer 19 |
| 21 | Convolution Layer | Output of Layer 20 |
| 22 | Pad Layer | Output of Layer 21 |
| 23 | Concatenate Layer | Output of Layers 6 and 22 |
| 24 | Convolution Layer | Output of Layer 23 |
| 25 | Convolution Layer | Output of Layer 24 |
| 26 | Upscale Layer | Output of Layer 25 |
| 27 | Convolution Layer | Output of Layer 26 |
| 28 | Pad Layer | Output of Layer 27 |
| 29 | Concatenate Layer | Output of Layers 3 and 28 |
| 30 | Convolution Layer | Output of Layer 29 |
| 31 | Convolution Layer | Output of Layer 30 |
| 32 | Convolution Layer | Output of Layer 31 |

In some embodiments, statistical prior knowledge may be integrated into a convolutional neural network. For example, prior statistical knowledge, obtained through principal components analysis (PCA), may be integrated into a convolutional neural network in order to obtain robust predictions even when dealing with corrupted or noisy data. In these embodiments, the network architecture may be trained end-to-end and include a specially designed layer which incorporates the dataset modes of variation discovered via PCA and produces predictions by linearly combining them. Further, a mechanism may be included to focus the attention of the convolutional neural network on specific regions of interest of an input image in order to obtain refined predictions.

The complexity of anatomical structures along with the presence of noise, artifacts, visual clutter, and poorly defined image areas often cause ambiguities and errors in image analysis. In the medical domain, many of these errors can be resolved by relying on statistical prior knowledge. For example, in segmentation it is useful to incorporate prior knowledge about the segmentation contour. Landmark localization tasks can benefit from the semantic relationships between different landmarks and how their positions are allowed to change with respect to each other. Finally, statistical models capturing the appearance of selected regions have been shown to improve results in a number of cases.

Shape models have also been used to constrain segmentation algorithms that are based on machine learning. This has been done by learning a posterior distribution of PCA coefficients and by re-projecting portions of ground truth contours onto unseen examples. These models rely on shallow architectures, manually engineered or learned features and shape constraints being imposed as part of a regularization or post-processing step.

Deep learning approaches and convolutional neural networks in particular, have shown astonishing capabilities to learn a hierarchy of features directly from raw data. Deep learning models are organized in multiple layers, where features are extracted in a cascaded fashion. As the depth of the network increases, the extracted features refer to bigger image regions and therefore recognize higher level concepts compared to the ones extracted in earlier layers.

Unfortunately, the applicability of deep learning approaches in medical image analysis is often limited by the requirement to train with large annotated datasets. Supplying more annotated data during the learning process allows a larger amount of challenging, real-world situations to be captured and therefore partly overcomes the difficulty to integrate prior statistical knowledge in the learning process. In the medical domain, it is often difficult to obtain large annotated datasets due to limitations on data usage and circulation and the tediousness of the annotation process. Moreover, medical images typically exhibit large variability in the quality and appearance of the structures across different scans, which further hampers the performances of machine vision algorithms. Ultrasound images, in particular, are often corrupted by noise, shadows, signal drop regions, and other artifacts that make their interpretation challenging even to human observers. Additionally, ultrasound scans exhibit high intra- and inter-operator acquisition variability, even when scanned by experts.

In some embodiments, PCA may be employed to advantageously discover the principal modes of variation of training data. Such discovered principle modes of variation may be integrated into a convolutional neural network. The robustness of the results is increased by constraining the network predictions with prior knowledge extracted by statistically analyzing the training data. This approach makes it possible to process cases where the anatomy of interest appears only partially, its appearance is not clear, or it visually differs from the observed training examples.

A convolutional network architecture may be employed that includes a new PCA layer that incorporates the dataset modes of variation and produces predictions as a linear combination of the modes. This process is used in procedure that focuses the attention of the subsequent convolutional neural network layers on the specific region of interest to obtain refined predictions. Importantly, the network is trained end-to-end with the shape encoded in a PCA layer and the loss imposed on the final location of the points. The end-to-end training makes it possible to start from a random configuration of network parameters and find the optimal set of filters and biases according to the estimation task and training data. This method may be applied to, for example, the landmark localization in 2D echocardiography images acquired from the parasternal long axis view and to the left ventricle segmentation of the heart in scans acquired from the apical four chamber view.

Incorporating statistical prior knowledge obtained through PCA into a convolutional neural network may advantageously overcome the limitations of previous deep learning approaches which lack strong shape priors and the limitations of active shape models which lack advanced pattern recognition capabilities. This approach may be fully automatic and therefore differs from most previous methods based on ASM which required human interaction. The neural network outputs the prediction in a single step without requiring any optimization loop.

In some embodiments, a training set containing N images and the associated ground truth annotations consisting of coordinates referring to P key-points which describe the position of landmarks may be employed. The training set may be used to first obtain the principal modes of variation of the coordinates in Y and then train a convolutional neural network that leverages it. The information used to formulate our predictions is obtained after multiple convolution and pooling operations and therefore fine-grained, high-resolution details might be lost across the layers. For this reason, a mechanism may be employed that focuses the attention of the network on full-resolution details by cropping portions of the image in order to refine the predictions. The architecture may be trained end-to-end, and all the parameters of the network may be updated at every iteration.

Much of the variability of naturally occurring structures, such as organs and anatomical details of the body, is not arbitrary. By simple observation of a dataset of shapes representative of a population, for example, one can notice the presence of symmetries and correlations between different shape parts. In the same way, it is often possible to observe correlations in the position of different landmarks of the body since they are tightly entangled with each other. PCA can be used to discover the principal modes of variation of the dataset at hand. When shapes are described as aligned point sets across the entire dataset, PCA reveals what correlations exist between different points and defines a new coordinates frame where the principal modes of variation correspond to the axes. Having a matrix Y containing the dataset, where each observation $y_i$ constitutes one of its columns, its principal components may be obtained by first de-meaning Y through equation (3):

$$\tilde{Y} = Y - \mu, \text{ with } \mu = \frac{1}{N}\sum_i y_i \quad (3)$$

and then by computing the eigenvectors of the covariance matrix $\tilde{Y}\tilde{Y}^T$. This corresponds to U in equation (4):

$$\tilde{Y} = U\Sigma V^T \quad (4)$$

Which is obtained via singular value decomposition (SVD). The matrix $\tilde{Y} = U\Sigma V^T$ is diagonal and contains the eigenvalues of the covariance matrix and represent the variance associated with each principle component in the eigenbase.

Any example in the dataset can be synthesized as a linear combination of the principle components as shown in Equation (5):

$$y_i = Uw + \mu \quad (5)$$

Each coefficient of the linear combination governs not only the position of one, but multiple correlated points that may describe the shape at hand. Imposing constraints on the coefficients weighting the effect of each principal component, or reducing their number until the correct balance between percent-age of retained variance and number of principal components is reached, it is possible to synthesize shapes that respect the concept of "legal shape" introduced before.

The convolutional neural network may not be trained to perform regression on the weights w in Equation 5. Instead, an end-to-end architecture may be used where the network directly uses the PCA eigenbase to make predictions from an image in the form of key-points locations. This has direct consequences on the training process. The network learns, by minimizing the loss, to steer the coefficients while being "aware" of their effect on the results. Each of the weights controls the location of multiple correlated key-points simultaneously. Since the predictions are obtained as a linear combination of the principal components, they obey the concept of "legal shape" and therefore are more robust to missing data, noise, and artifacts.

The network may include two branches. The first branch employs convolutional, pooling, and dense layers, and produces a coarse estimate of the key-point locations via PCA. The second branch operates on full resolution patches cropped from the input image around the coarse key-point locations. The output of the second network refines the predictions made by the first by using more fine-grained visual information. Both the branches are trained simultaneously and are fully differentiable. The convolutions are all applied without padding and they use kernels of size 3×3 in the first convolutional neural network branch and 5×5 in the second, shallower, branch. The nonlinearities used throughout the network are rectified linear functions. All the inputs of the PCA layer, are not processed through nonlinearities.

The PCA layer implements a slightly modified of the synthesis equation in 5. In addition to the weights w, which are supplied by a dense layer of the network, a global shift s that is applied to all the predicted points is also supplied. Through the bi-dimensional vector s, translations of the anatomy of interest are able to be handled. With a slight abuse of notation, Equation 5 may be re-written as shown in Equation (6):

$$y_i = Uw + \mu + s. \quad (6)$$

The layer performing cropping follows an implementation inspired to spatial transformers which ensures differentiability. A regular sampling pattern is translated to the coarse key-point locations and the intensity values of the surrounding area are sampled using bilinear interpolation. Having P key-points, P patches may be obtained for each of the K images in the mini-batch. The resulting KP patches are then processed through a 3-layers deep convolutional neural network using 8 filters applied without padding, which reduces their size by a total of 12 pixels. After the convolution layers, the patches are again arranged into a batch of K elements having P×8 channels, and further processed through three dense layers, which ultimately compute $w_A$ having the same dimensionality of w. The refined weights $w_F$ which are employed in the PCA layer to obtain a more accurate key-point prediction, are obtained as $w_F = w_A + w$.

This approach has been tested on two different ultrasound dataset depicting the human heart with the aim to solve two different tasks with good results. The first task is segmentation of the left ventricle (LV) of the heart form scans acquired from the apical view, while the second task is a landmark localization problem where the aim is to localize 14 points of interest in images acquired from the parasternal long axis view. In the first case, the model leverages prior statistical knowledge relative to the shape of the structures of interest, while in the second case the model captures the spatiotemporal relationships between landmarks across cardiac cycles of different patients. For the segmentation task a total of 1100 annotated images, 953 for training and 147 for testing, were employed.

The inventors have appreciated that accurate landmark localization in ultrasound video sequences is challenging due to noise, shadows, anatomical differences, and scan plane variation. Accordingly, the inventors have conceived and developed a fully convolutional neural network trained to regress the landmark locations that may address such challenges. In this convolutional neural network, a series of convolution and pooling layers is followed by a collection of upsampling and convolution layers with feature forwarding from the earlier layers. The final location estimates are produced by computing a center of mass of the regression maps in the last layer. In addition, uncertainty of the estimates are computed as the standard deviations of the predictions. The temporal consistency of the estimates is achieved by a Long Short-Term memory cells which processes several previous frames in order to refine the estimate in the current frame. The results on automatic measurement of left ventricle in parasternal long axis views and subsequent ejection fraction computation show accuracy on par with inter-user variability.

Regression modeling is an approach for describing relationship between an independent variable and one or more dependent variables. In machine learning, this relationship is described by a function whose parameters are learned from training examples. In deep learning models, this function is a composition of logistic (sigmoid), hyperbolic tangent, or more recently rectified linear functions at each layer of the network. In many applications, the function learns a mapping between input image patches and a continuous prediction variable.

Regression modeling has been used to detect organ or landmark locations in images, visually track objects and features, and estimate body poses. The deep learning approaches have outperformed previous techniques especially when a large annotated training data set is available. The proposed architectures used cascade of regressors, refinement localization stages, and combining cues from multiple landmarks to localize landmarks. In medical images, the requirements on accurate localization are high since the landmarks are used as measurement points to help in diagnosis. When tracking the measurements in video sequences, the points must be accurately detected in each frame while ensuring temporal consistency of the detections.

A fully convolutional network architecture for accurate localization of anatomical landmark points in video sequences has been devised. The advantage of the fully convolutional network is that the responses from multiple windows covering the input image can be computed in a single step. The network is trained end-to-end and outputs the locations of the landmarks. The aggregation of the regressed locations at the last convolution layer is ensured by a new center-of-mass layer which computes mean position of the predictions. The layer makes it possible to use new regularization technique based on variance of the predicted candidates and to define new loss based on relative locations of landmarks. The evaluation is fast to process each frame of a video sequence at near frame rate speeds. The temporal consistency of the measurements is improved by Convolutional Long Short-term Memory (CLSTM) cells which process the feature maps from several previous frames and produce updated features for the current frame in order to refine the estimate.

Denote an input image of width w and height h as I (independent variable) and the position of k landmarks stacked columnwise into p (dependent variable). The goal of the regression is to learn a function $f(I; \theta)=p$ parametrized by $\theta$. f may be approximated by a convolutional neural network and train the parameters params using a database of images and their corresponding annotations. Typically, a Euclidean loss is employed to train f using each annotated image.

Previously, regression estimates were obtained directly from the last layer of the network, which was fully connected to previous layer. This is a highly non-linear mapping, where the estimate is computed from the fully connected layers after convolutional blocks. Instead of fully connected network, we propose to regress landmark locations using a fully convolutional architecture (FCNN). Their advantage is that the estimates can be computed in a single evaluation step. In the proposed architecture, landmark coordinate estimates may be obtained at each image location.

The aggregated landmark coordinate estimates are computed in a new center of mass layer from input at each predicting location $l_{ij}$:

$$\hat{p} = \frac{1}{w \times h} \sum_{i=1}^{h} \sum_{j=1}^{w} l_{ij} \quad (7)$$

Recurrent neural networks (RNN) can learn sequential context dependencies by accepting input $x_t$ and updating a hidden vector $h_t$ at every time step t. The RNN network can be composed of Long-short Term Memory (LSTM) units, each controlled by a gating mechanism with three types of updates, $i_t, f_t, o_t$, that range between 0 and 1. The value $i_t$ controls the update of each memory cell, $f_t$ controls the forgetting of each memory cell, and $o_t$ controls the influence of the memory state on the hidden vector. In Convolutional LSTMs (CLSTMs), the input weights and hidden vector weights are convolved instead of multiplied to model spatial constraints. The function introduces a non-linearity, which may be chosen to be tanh. Denoting the convolutional operator as * for equations 8-10, the values at the gates are computed as follows:

$$\text{forgetgate: } f_t = \text{sigm}(W_f * [h_{t-1}, x_t] + b_f) \quad (8)$$

$$\text{inputgate: } i_t = \text{sigm}(W_i * [h_{t-1}, x_t] + b_i) \quad (9)$$

$$\text{outputgate: } o_t = \text{sigm}(W_o * [h_{t-1}, x_t] + b_o) \quad (10)$$

The parameters of the weights W and biases b are learned from training sequences. In addition to the gate values, each CLSTM unit computes state candidate values:

$$g_t = \tanh(W_g * [h_{t-1}, x_t] + b_g) \quad (11)$$

where $g_t$ ranges between −1 and 1 and influences memory contents. The memory cell is updated by $$c_t = f_t \odot c_{t-1} + i_t \odot g_t \quad (12)$$

which additively modifies each memory cell. The update process results in the gradients being distributed during backpropagation. The symbol $c_t = f_t \odot c_{t-1} + i_t \odot g_t$ denotes the Hadamard product. Finally, the hidden state is updated as:

$$h_t = o_t \odot \tanh(c_t) \quad (13)$$

In sequential processing of image sequences, the inputs into the LSTM consist of the feature maps computed from a convolutional neural network. In this work, two architectures are proposed to compute the feature maps. The first architecture is a neural network with convolution and pooling layers. After sequential processing the feature maps in CLSTM, the output is fed into fully connected layers to compute the landmark location estimate. In the second architecture, the CLSTM inputs is the final layer of a convolutional path of the fully convolutional architecture (FCN). The landmark location estimates are computed from the CLSTM output processed through the transposed convolutional part of the FCN network.

Figure 20:
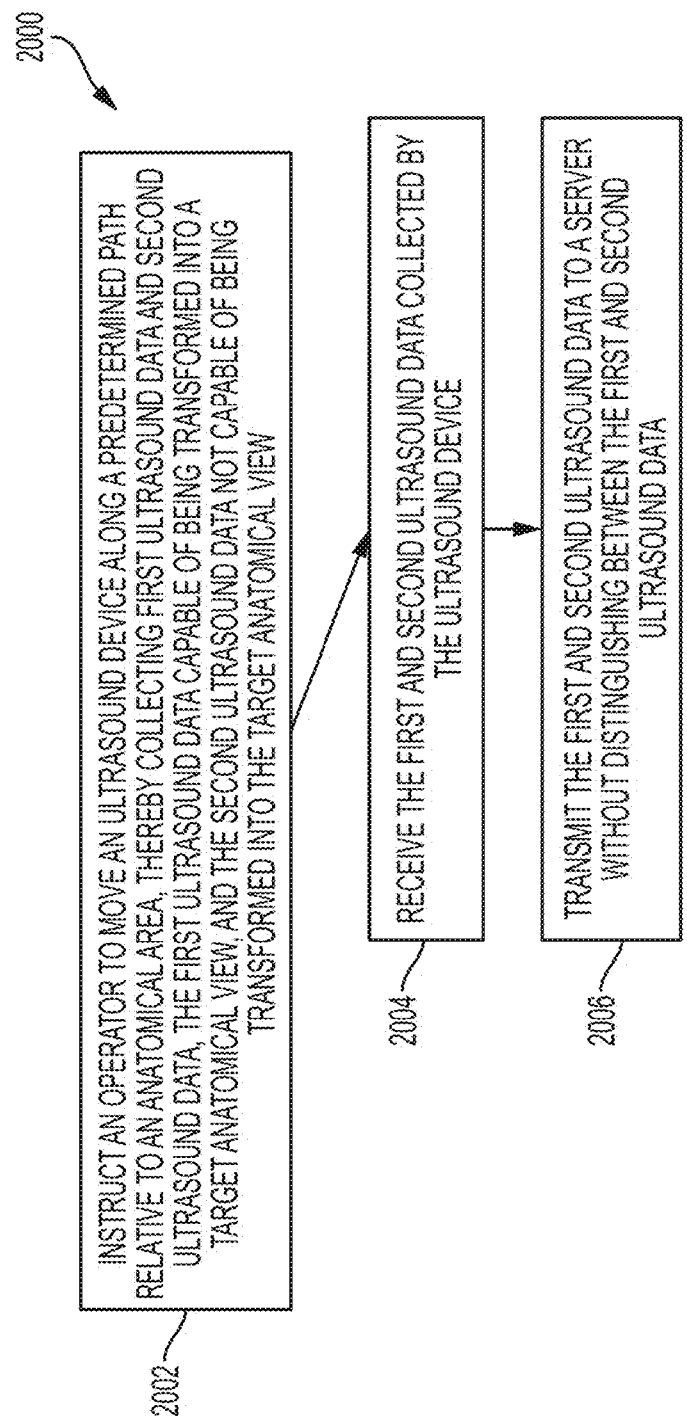
FIG. 20 shows an example process for capturing ultrasound data capable of being transformed into an ultrasound image of a target anatomical view, in accordance with certain embodiments disclosed herein.

FIG. 20 shows an example process 2000 for capturing ultrasound data capable of being transformed into an ultrasound image of a target anatomical view, in accordance with certain embodiments disclosed herein. The process 2000 may be performed by, for example, a host device (e.g., host device 101, 201, 301, 401, 501, 601, 701, 801, 901, 1104, or 1302) in an ultrasound system. As shown, the process 2000 includes an act 2002 of instructing an operator, an act 2004 of receiving ultrasound data, and an act 2006 of transmitting the ultrasound data.

In act 2002, a host device may instruct an operator to move an ultrasound device (e.g., ultrasound device 1102 or 1314) along a predetermined path (e.g., predetermined path 107, 207, 307, 407, 507, 607, 707, or 807) relative to an anatomical area (e.g., anatomical area 105, 205, 305, 405, 505, 605, 705, or 805) in order to collect first ultrasound data and second ultrasound data, the first ultrasound data capable of being transformed into a target anatomical view, and the second ultrasound data not capable of being transformed into the target anatomical view. In some embodiments, the instructions may be displayed on a display (e.g., display 103, 203, 303, 403, 503, 703, 803, 903, or 1308) of the host device and may include a predetermined image and/or a predetermined video and/or predetermined text. In some embodiments, the instructions may be played as audio by a speaker (e.g., speaker 603 or audio output device 1304) of the host device. In some embodiments, the predetermined path may substantially cover (e.g., as a serpentine path, a spiral path, or a path including parallel legs proceeding in the same direction) all of the anatomical area. In some embodiments, the predetermined path may substantially cover an anatomical area greater in area than 1 $cm^2$, 5 $cm^2$, 10 $cm^2$, 25 $cm^2$, 50 $cm^2$, 100 $cm^2$, 500 $cm^2$, 1000 $cm^2$, 5000 $cm^2$, 1 $m^2$, or any other suitable area. In some embodiments, the predetermined path may substantially cover all of a surface of the abdomen, arm, breast, chest, foot, genitalia, hand, head, leg, neck, pelvis, thorax, and/or torso. In some embodiments, the predetermined path may substantially cover a portion of the abdomen, arm, breast, chest, foot, genitalia, hand, head, leg, neck, pelvis, thorax, and/or torso. In some embodiments, the host device may be a mobile smartphone, a tablet, a laptop, a smart watch, a virtual reality (VR) headset, an augmented reality (AR) headset, or a smart wearable device. In some embodiments, instead of or in addition to providing instructions to move the ultrasound device along a predetermined path, the host device may provide instructions to move the ultrasound device through a predetermined rotation at a specific location within the anatomical area. In some embodiments, the host device may provide instructions to move an ultrasound device along a predetermined path while moving the ultrasound device through a predetermined rotation. In some embodiments, the host device may generate or retrieve the predetermined path from a database. In some embodiments, an individual (e.g., a remote expert operating a remote processing device) may generate or select the predetermined path and transmit the path (or an indication thereof) to the host device. In some embodiments, the host device does not provide feedback to the operator regarding collection of the first ultrasound data while the operator moves the ultrasound device along the path.

As discussed above, it can be beneficial to instruct the operator to move the ultrasound device along a path whereby the ultrasound device collects target and non-target ultrasound data, as such an instruction may be easier to describe and follow than a specific description of the target location. In other words, purposefully instructing the operator to collect non-target ultrasound data may help the operator to collect the target ultrasound data.

In act 2004, the host device may receive the first and second ultrasound data collected by the ultrasound device.

In some embodiments, the host device may receive the first and second ultrasound data collected by the ultrasound device over a cable such as a Universal Serial Bus (USB) cable or a Lightning cable. In some embodiments, the host device may receive the first and second ultrasound data over a wireless communication link such as a BLUETOOTH, WiFi, or ZIGBEE wireless communication link.

In act 2006, the host device may transmit the first and second ultrasound data to a server (e.g., server 1318) without distinguishing between the first and second ultrasound data. For example, the host device may transmit the first and second ultrasound data to the server without identifying whether the first ultrasound data is capable of being transformed in an ultrasound image of the target anatomical view and/or whether the second ultrasound data is capable of being transformed in an ultrasound image of the target anatomical view. In some embodiments, the host device may transmit the first and second ultrasound data to the server over a wired connection (e.g., via an Ethernet cable). In some embodiments, the host device may transmit the first and second ultrasound data to the server over a wireless connection (e.g., over a WiFi network). In some embodiments, instead of the host device receiving the first and second ultrasound data and transmitting it to the server, the ultrasound device may directly transmit the first and second ultrasound data to the server. In some embodiments, acts 2004 and/or 2006 may be optional.

Identifying the target ultrasound data and the non-target ultrasound data may require storage of specific algorithms for analyzing the collected ultrasound data, sufficient processing speed to execute computations using these algorithms, and consumption of power while executing the computations. Because the host device can transmit the collected ultrasound data to a server without distinguishing between the target ultrasound data and the non-target ultrasound data, the host device may have lower requirements in terms of memory, processing speed, and power consumption. This may be beneficial when the host device is a personal smartphone, tablet, etc.

FIG. 21 shows an example process 2100 for processing ultrasound data in accordance with certain embodiments disclosed herein. The process 2100 may be performed by, for example, a server (e.g., server 1318) in an ultrasound system. As shown, the process 2100 includes an act 2102 of receiving ultrasound data, an act 2104 of identifying ultrasound data capable of being transformed into an ultrasound image of a target anatomical view, an act 2106 of saving ultrasound data, an act 2108 of identifying ultrasound data not capable of being transformed into an ultrasound image of the target anatomical view, and an act 2110 of discarding ultrasound data.

In act 2102, a server may receive first and second ultrasound data, the first ultrasound data capable of being transformed into a target anatomical view, and the second ultrasound data not capable of being transformed into the target anatomical view. In some embodiments, the server may receive the first and second ultrasound data from a host device (e.g., host device 101, 201, 301, 401, 501, 601, 701, 801, 901, 1104, or 1302) over a wired connection (e.g., via an Ethernet cable). In some embodiments, the server may receive the first and second ultrasound data from the host device over a wireless connection (e.g., over a WiFi network). In some embodiments, the server may receive the first and second ultrasound data from the ultrasound device over a wireless connection (e.g., over a WiFi network). In some embodiments, the server may be configured to transform the received ultrasound data into ultrasound images. In some embodiments, the ultrasound device may be configured to transform ultrasound data into ultrasound images and transmit the ultrasound images to the host device. In such embodiments, the host device that provides the instructions to the operator may receive the ultrasound images and transmit the ultrasound images to the server.

In act 2104, the server may identify that the first ultrasound data is capable of being transformed into the target anatomical view. In some embodiments, the server may use deep learning techniques (e.g., techniques described with reference to FIG. 19) to perform the identification.

In act 2106, the server may, based on identifying that the first ultrasound data is capable of being transformed into the target anatomical view, save the first ultrasound data to memory (e.g., memory 1312 or memory circuitry 1207). In some embodiments, the server may be configured to send the ultrasound data and/or ultrasound image(s) representing the target anatomical view to a medical professional (e.g., by email).

In act 2108, the server may identify that the second ultrasound data is not capable of being transformed into the target anatomical view. In some embodiments, the server may use deep learning techniques (e.g., techniques described with reference to FIG. 19) to perform the identification.

In act 2110, the server may, based on identifying that the second ultrasound data is not capable of being transformed into the target anatomical view, discard the second ultrasound data. In some embodiments, instead of discarding the second ultrasound data, the server may save the second ultrasound data to memory as well.

Identifying the target ultrasound data and the non-target ultrasound data may require storage of specific algorithms for analyzing the collected ultrasound data, sufficient processing speed to execute computations using these algorithms, and consumption of power while executing the computations. Because a host device can transmit the collected ultrasound data to the server without distinguishing between the target ultrasound data and the non-target ultrasound data, and offload responsibility for identifying the target ultrasound data and the non-target ultrasound data to the server, the host device may have lower requirements in terms of memory, processing speed, and power consumption. This may be beneficial when the host device is a personal smartphone, tablet, etc.

Various inventive concepts may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments. Further, one or more of the processes may be combined. Further, one or more acts of each process may be omitted.

The terms "program," "application," or "software" are used herein in a generic sense to refer to any type of computer code or set of processor-executable instructions that may be employed to program a computer or other processor to implement various aspects of embodiments as discussed above. Additionally, according to one aspect, one or more computer programs that when executed perform methods of the disclosure provided herein need not reside on a single computer or processor, but may be distributed in a modular fashion among different computers or processors to implement various aspects of the disclosure provided herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Further, some actions are described as taken by a "operator" or "subject." It should be appreciated that a "operator" or "subject" need not be a single individual, and that in some embodiments, actions attributable to an "operator" or "subject" may be performed by a team of individuals and/or an individual in combination with computer-assisted tools or other mechanisms. Further, it should be appreciated that, in some instances, a "subject" may be the same person as the "operator." For example, an individual may be imaging themselves with an ultrasound device and, thereby, act as both the "subject" being imaged and the "operator" of the ultrasound device.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. A method, comprising:
   instructing, by a host device, an operator to move an ultrasound device along a predetermined path relative to an anatomical area, the predetermined path including a point from which a first anatomical view that is a target anatomical view is available and a point from which a second anatomical view that is different than the target anatomical view is available, and wherein the predetermined path is determined prior to collecting ultrasound imagery; and
   receiving, at the host device, a first ultrasound image depicting the first anatomical view and a second ultrasound image depicting the second anatomical view as collected by the ultrasound device while moving along the predetermined path; and
   transmitting, by the host device, the first and second ultrasound images to a server,
   wherein, after movement of the ultrasound device along the predetermined path is complete, the server is configured to:
      identify that the second ultrasound image depicts the second anatomical view that is different than the target anatomical view; and
      based on identifying that the second ultrasound image depicts the second anatomical view that is different than the target anatomical view, discard the second ultrasound image.

2. The method of claim 1, wherein the server is configured to:
   identify that the first ultrasound image depicts the target anatomical view; and
   based on identifying that the first ultrasound image depicts the target anatomical view, save the first ultrasound image to memory.

3. The method of claim 2, wherein the server is configured to use a machine learning technique to identify that the first ultrasound image depicts the target anatomical view.

4. The method of claim 1, wherein instructing the operator comprises providing at least one of a predetermined video and a predetermined image displaying the predetermined path.

5. The method of claim 1, wherein instructing the operator comprises providing instructions expressed in words for moving the ultrasound device along the predetermined path relative to the anatomical area.

6. The method of claim 1, wherein the predetermined path comprises points across substantially all of a surface of at least one of an abdomen, arm, breast, chest, foot, genitalia, hand, head, leg, neck, pelvis, thorax, and torso.

7. The method of claim 1, wherein the predetermined path comprises a serpentine path across substantially all of the anatomical area.

8. The method of claim 1, wherein:
   the predetermined path comprises a path across substantially all of the anatomical area; and
   the anatomical area is greater than 25 cm$^2$ in area.

9. The method of claim 1, wherein the predetermined path comprises a pivot of the ultrasound device.

10. The method of claim 1, wherein the predetermined path comprises a rotation of the ultrasound device about its longitudinal axis.

11. The method of claim 1, wherein the first anatomical view is of a first anatomical structure and wherein the second anatomical view is of a second anatomical structure different than the first anatomical structure.

12. The method of claim 1, wherein the first anatomical view is a parasternal long axis view.

13. The method of claim 1, wherein the first anatomical view is an apical four chamber view.

14. A method, comprising:
   instructing, by a host device, an operator to move an ultrasound device along a predetermined path relative to an anatomical area, the predetermined path including a point from which a first anatomical view that is a target anatomical view is available and a point from which a second anatomical view that is different than the target anatomical view is available, and wherein the predetermined path is determined prior to collecting ultrasound imagery; and
   receiving, at the host device, a first ultrasound image depicting the first anatomical view and a second ultrasound image depicting the second anatomical view as collected by the ultrasound device while moving along the predetermined path;
   transmitting, by the host device, the first and second ultrasound images to a server, wherein
   after movement of the ultrasound device along the predetermined path is complete, the server is configured to:
      identify that the second ultrasound image depicts the second anatomical view that is different than the target anatomical view; and
      based on identifying that the second ultrasound image depicts the second anatomical view that is different than the target anatomical view, discard the second ultrasound image, and
   the host device does not provide feedback to the operator regarding collection of a first ultrasound image depicting the first anatomical view while the operator moves the ultrasound device along the predetermined path.

15. The method of claim 14, wherein the server is configured to:
   identify that the first ultrasound image depicts the target anatomical view; and
   based on identifying that the first ultrasound image depicts the target anatomical view, save the first ultrasound image to memory.

16. The method of claim 15, wherein the server is configured to use a machine learning technique to identify that the first ultrasound image depicts the target anatomical view.

17. The method of claim 14, wherein the server is configured to use a machine learning technique to identify that the second ultrasound image depicts the second anatomical view that is different than the target anatomical view.

18. The method of claim 14, wherein the predetermined path comprises points across substantially all of a surface of at least one of an abdomen, arm, breast, chest, foot, genitalia, hand, head, leg, neck, pelvis, thorax, and torso.

19. The method of claim 14, wherein:
   the predetermined path comprises a path across substantially all of the anatomical area; and
   the anatomical area is greater than 25 cm$^2$ in area.

20. The method of claim 14, wherein the predetermined path comprises a pivot of the ultrasound device.

21. The method of claim 14, wherein the predetermined path comprises a rotation of the ultrasound device about its longitudinal axis.

22. The method of claim 14, wherein the first anatomical view is of a first anatomical structure and wherein the second anatomical view is of a second anatomical structure different than the first anatomical structure.

23. The method of claim 14, wherein the first anatomical view is a parasternal long axis view.

24. The method of claim 14, wherein the first anatomical view is an apical four chamber view.

25. The method of claim 14, wherein instructing the operator comprises providing at least one of a predetermined video and a predetermined image displaying the predetermined path.

* * * * *